(12) United States Patent
Osaka et al.

(10) Patent No.: US 11,980,087 B2
(45) Date of Patent: May 7, 2024

(54) TRIARYLAMINE DERIVATIVE, LIGHT-EMITTING SUBSTANCE, LIGHT-EMITTING ELEMENT, LIGHT-EMITTING DEVICE, AND ELECTRONIC DEVICE

(71) Applicant: Semiconductor Energy Laboratory Co., Ltd., Kanagawa-ken (JP)

(72) Inventors: Harue Osaka, Kanagawa (JP); Takahiro Ushikubo, Kanagawa (JP); Nobuharu Ohsawa, Kanagawa (JP); Satoshi Seo, Kanagawa (JP); Tsunenori Suzuki, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 18/200,370

(22) Filed: May 22, 2023

(65) Prior Publication Data

US 2023/0301178 A1    Sep. 21, 2023

Related U.S. Application Data

(60) Continuation of application No. 17/065,762, filed on Oct. 8, 2020, now Pat. No. 11,678,568, which is a (Continued)

(30) Foreign Application Priority Data

| May 16, 2008 | (JP) | 2008-129991 |
| Nov. 26, 2008 | (JP) | 2008-300827 |
| Sep. 2, 2009 | (JP) | 2009-022314 |

(51) Int. Cl.
*H01L 51/50* (2006.01)
*C07C 211/54* (2006.01)
(Continued)

(52) U.S. Cl.
CPC .......... *H10K 85/633* (2023.02); *C07C 211/54* (2013.01); *C09K 11/025* (2013.01);
(Continued)

(58) Field of Classification Search
None
See application file for complete search history.

(56) References Cited

U.S. PATENT DOCUMENTS

| 5,061,569 A | 10/1991 | VanSlyke et al. |
| 5,415,962 A | 5/1995 | Kanemaru et al. |

(Continued)

FOREIGN PATENT DOCUMENTS

| CN | 101296895 A | 10/2008 |
| EP | 0 567 396 A1 | 10/1993 |

(Continued)

OTHER PUBLICATIONS

Goldsmith.C et al., "C—H Bond Activation by a Ferric Methoxide Complex: Modeling the Rate-Determining Step in the Mechanism of Lipoxygenase", J. Am. Chem. Soc. (Journal of the American Chemical Society), 2002, vol. 124, No. 1, pp. 83-96.

(Continued)

*Primary Examiner* — Gregory D Clark
(74) *Attorney, Agent, or Firm* — Husch Blackwell LLP

(57) ABSTRACT

A triarylamine derivative represented by a general formula (G1) given below is provided. Note that in the formula, Ar represents either a substituted or unsubstituted phenyl group or a substituted or unsubstituted biphenyl group; α represents a substituted or unsubstituted naphthyl group; β represents either hydrogen or a substituted or unsubstituted naphthyl group; n and m each independently represent 1 or 2; and $R^1$ to $R^8$ each independently represent any of hydrogen, an alkyl group having 1 to 6 carbon atoms, or a phenyl group.

(Continued)

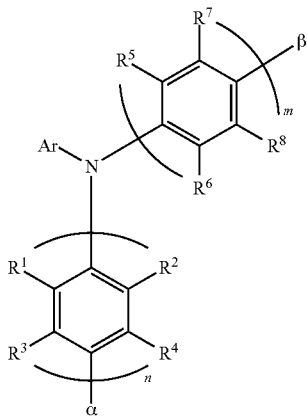

(G1)

20 Claims, 22 Drawing Sheets

Related U.S. Application Data continuation of application No. 15/399,408, filed on Jan. 5, 2017, now Pat. No. 10,804,471, which is a continuation of application No. 14/605,286, filed on Jan. 26, 2015, now Pat. No. 9,540,315, which is a division of application No. 13/474,104, filed on May 17, 2012, now Pat. No. 8,940,416, which is a continuation of application No. 12/464,506, filed on May 12, 2009, now Pat. No. 8,182,933.

(51) Int. Cl.
C09K 11/02 (2006.01)
C09K 11/06 (2006.01)
H05B 33/14 (2006.01)
H10K 85/30 (2023.01)
H10K 85/60 (2023.01)
H10K 50/11 (2023.01)
H10K 50/14 (2023.01)
H10K 50/15 (2023.01)
H10K 50/16 (2023.01)
H10K 50/19 (2023.01)
H10K 59/32 (2023.01)
H10K 101/10 (2023.01)

(52) U.S. Cl.
CPC ............ *C09K 11/06* (2013.01); *H05B 33/14* (2013.01); *H10K 85/342* (2023.02); *H10K 85/626* (2023.02); *H10K 85/631* (2023.02); *H10K 85/636* (2023.02); *C07C 2601/14* (2017.05); *C09K 2211/1007* (2013.01); *C09K 2211/1011* (2013.01); *C09K 2211/1014* (2013.01); *C09K 2211/1029* (2013.01); *C09K 2211/185* (2013.01); *H10K 50/11* (2023.02); *H10K 50/14* (2023.02); *H10K 50/15* (2023.02); *H10K 50/16* (2023.02); *H10K 50/19* (2023.02); *H10K 59/32* (2023.02); *H10K 85/615* (2023.02); *H10K 85/6572* (2023.02); *H10K 2101/10* (2023.02); *Y10S 428/917* (2013.01)

(56) References Cited

U.S. PATENT DOCUMENTS

| | | | |
|---|---|---|---|
| 6,656,608 | B1 | 12/2003 | Kita et al. |
| 6,723,455 | B2 | 4/2004 | Ueda et al. |
| 6,743,948 | B1 | 6/2004 | Hosokawa et al. |
| 6,949,878 | B2 | 9/2005 | Suzuri et al. |
| 7,264,890 | B2 | 9/2007 | Kita et al. |
| 7,271,406 | B2 | 9/2007 | Bentsen et al. |
| 7,316,851 | B2 | 1/2008 | Kita et al. |
| 7,871,713 | B2 | 1/2011 | Kita et al. |
| 8,101,857 | B2 | 1/2012 | Kido et al. |
| 8,129,038 | B2 | 3/2012 | Yabunouchi et al. |
| 8,182,933 | B2 | 5/2012 | Osaka et al. |
| 8,247,805 | B2 | 8/2012 | Yu et al. |
| 8,623,522 | B2 | 1/2014 | Yabunouchi et al. |
| 8,629,613 | B2 | 1/2014 | Yabunouchi et al. |
| 8,723,025 | B2 | 5/2014 | Kido et al. |
| 8,883,324 | B2 | 11/2014 | Yabunouchi et al. |
| 8,889,268 | B2 | 11/2014 | Takada et al. |
| 8,940,416 | B2 | 1/2015 | Osaka et al. |
| 9,112,170 | B2 | 8/2015 | Ohsawa et al. |
| 9,159,931 | B2 | 10/2015 | Yabunouchi et al. |
| 9,306,173 | B2 | 4/2016 | Yabunouchi et al. |
| 9,444,053 | B2 | 9/2016 | Yabunouchi et al. |
| 9,540,315 | B2 | 1/2017 | Osaka et al. |
| 10,804,471 | B2 | 10/2020 | Osaka et al. |
| 2004/0033387 | A1 | 2/2004 | Wang et al. |
| 2004/0062951 | A1 | 4/2004 | Kita et al. |
| 2004/0072019 | A1 | 4/2004 | Kita et al. |
| 2004/0151943 | A1 | 8/2004 | Lee et al. |
| 2006/0091359 | A1 | 5/2006 | Lai et al. |
| 2007/0145888 | A1 | 6/2007 | Yabunouchi et al. |
| 2008/0076942 | A1 | 3/2008 | Kawamura |
| 2008/0303417 | A1 | 12/2008 | Yabunouchi et al. |
| 2009/0160323 | A1 | 6/2009 | Nomura et al. |
| 2010/0155706 | A1 | 6/2010 | Yu et al. |
| 2012/0184776 | A1 | 7/2012 | Yabunouchi et al. |
| 2012/0228594 | A1 | 9/2012 | Yabunouchi et al. |
| 2012/0280221 | A1 | 11/2012 | Yu et al. |
| 2012/0302793 | A1 | 11/2012 | Yabunouchi et al. |
| 2014/0246071 | A1 | 9/2014 | Kido et al. |
| 2014/0346479 | A1 | 11/2014 | Kido et al. |
| 2015/0325806 | A1 | 11/2015 | Ohsawa et al. |

FOREIGN PATENT DOCUMENTS

| | | |
|---|---|---|
| EP | 1 013 740 A2 | 6/2000 |
| EP | 1 191 821 A1 | 3/2002 |
| EP | 1 289 015 A2 | 3/2003 |
| EP | 1 617 493 A2 | 1/2006 |
| EP | 1 731 585 A2 | 12/2006 |
| EP | 1 731 586 A2 | 12/2006 |
| EP | 1 764 401 A1 | 3/2007 |
| EP | 1 834 945 A1 | 9/2007 |
| EP | 1 834 946 A1 | 9/2007 |
| EP | 1 950 194 A1 | 7/2008 |
| EP | 2 011 790 A1 | 1/2009 |
| EP | 2 371 810 A1 | 10/2011 |
| EP | 2 639 231 A1 | 9/2013 |
| EP | 2 713 416 A1 | 4/2014 |
| JP | 04-319958 A | 11/1992 |
| JP | 07-053955 A | 2/1995 |
| JP | 10-226785 A | 8/1998 |
| JP | 11-184108 A | 7/1999 |
| JP | 2001-143869 A | 5/2001 |
| JP | 2001-271061 A | 10/2001 |
| JP | 2002-175883 A | 6/2002 |
| JP | 2002-241352 A | 8/2002 |
| JP | 2002-249765 A | 9/2002 |
| JP | 2002-329577 A | 11/2002 |
| JP | 2003-055320 A | 2/2003 |
| JP | 2003-089682 A | 3/2003 |
| JP | 2003-109758 A | 4/2003 |
| JP | 2003-151769 A | 5/2003 |
| JP | 2004-047443 A | 2/2004 |
| JP | 2006-024791 A | 1/2006 |
| JP | 2006-310351 A | 11/2006 |

(56) References Cited

FOREIGN PATENT DOCUMENTS

| | | |
|---|---|---|
| JP | 2007-015933 A | 1/2007 |
| JP | 2007-269738 A | 10/2007 |
| JP | 2008-120769 A | 5/2008 |
| JP | 2008-280386 A | 11/2008 |
| JP | 2010-523648 | 7/2010 |
| JP | 2010-186983 A | 8/2010 |
| JP | 5420310 B2 | 2/2014 |
| JP | 6179265 B2 | 8/2017 |
| JP | 6858210 B2 | 4/2021 |
| KR | 2007-0095817 A | 10/2007 |
| KR | 2008-0068860 A | 7/2008 |
| KR | 10-1453383 | 10/2014 |
| WO | WO 2006/073054 A1 | 7/2006 |
| WO | WO 2006/073059 A1 | 7/2006 |
| WO | WO 2007/058127 A1 | 5/2007 |
| WO | WO 2007/125714 A1 | 11/2007 |
| WO | WO 2008/035517 A1 | 3/2008 |
| WO | WO 2008/127057 A1 | 10/2008 |
| WO | WO 2009/139358 A1 | 11/2009 |

OTHER PUBLICATIONS

Onishi.T et al., "A Method of Measuring an Energy Level", High Molecular EL Materials—Development of Light-Emitting High Molecular Compounds, Dec. 25, 2004, pp. 64-67, Kyoritsu Shuppan.

International Search Report (Application No. PCT/JP2009/058787) dated Aug. 11, 2009.

Written Opinion (Application No. PCT/JP2009/058787) dated Aug. 11, 2009.

Liu.J, "Synthesis and properties of starburst intermediate N,N-diphenyl-4-iodophenylamine", Huaxue Shiji, 2006, vol. 28, No. 6, pp. 329-330 and 335.

Du.L, "Synthesis of two strong electro-donor triphenylaminostilbene-like derivations and investigation of photo-electrical properties", Journal of Functional Materials, 2006, vol. 37, No. 11, pp. 1700-1702.

Chinese Office Action (Application No. 201210279619.1) dated Sep. 30, 2013.

Taiwanese Office Action (Application No. 98116217) dated Dec. 24, 2013.

Taiwanese Office Action (Application No. 98116217) dated Apr. 3, 2014.

Temma.T et al., "Synthesis of Hyperbranched Polymer Having Binaphthol Units via Oxidative Cross-Coupling Polymerization", Journal of Polymer Science Part A: Polymer Chemistry, 2008, vol. 46, pp. 1034-1041.

Korean Office Action (Application No. 2010-7028253) dated Oct. 19, 2015.

Korean Office Action (Application No. 2010-7028253) dated Sep. 22, 2016.

Korean Office Action (Application No. 2017-7014222) dated Aug. 23, 2017.

Indian Office Action (Application No. 201718023134) dated Feb. 18, 2021.

TRIARYLAMINE DERIVATIVE, LIGHT-EMITTING SUBSTANCE, LIGHT-EMITTING ELEMENT, LIGHT-EMITTING DEVICE, AND ELECTRONIC DEVICE

This application is a continuation of pending application Ser. No. 17/065,762 filed on Oct. 8, 2020 which is a continuation of pending application Ser. No. 15/399,408 filed on Jan. 5, 2017 (now U.S. Pat. No. 10,804,471 issued Oct. 13, 2020) which is a continuation of application Ser. No. 14/605,286 filed on Jan. 26, 2015 (now U.S. Pat. No. 9,540,315 issued Jan. 10, 2017) which is a divisional of application Ser. No. 13/474,104 filed on May 17, 2012 (now U.S. Pat. No. 8,940,416 issued Jan. 27, 2015) which is a continuation of application Ser. No. 12/464,506 filed on May 12, 2009 (now U.S. Pat. No. 8,182,933 issued May 22, 2012), which are all incorporated herein by reference.

TECHNICAL FIELD

The present invention relates to a triarylamine derivative. In addition, the present invention relates to a light-emitting substance, a light-emitting element, and an electronic device using the triarylamine derivative.

BACKGROUND ART

A display device using a light-emitting element in which an organic compound is used as a light-emitting substance (an organic EL element) has been developed rapidly as a next generation display device because it has advantages such as thinness, lightness in weight, high response speed, and low power consumption. Although there have been various obstacles, technique has been improved such that organic EL televisions have become commercially available recently.

In an organic EL element, when voltage is applied between a pair of electrodes which interpose a light-emitting layer therebetween, electrons and holes injected from the electrodes are recombined to form an excited state, and when the excited state returns to a ground state, light is emitted. A wavelength of light emitted from a light-emitting substance is peculiar to the light-emitting substance; thus, by using different types of organic compounds as light-emitting substances, light-emitting elements which exhibit various wavelengths, i.e., various colors can be obtained.

In the case of a display device which is expected to display images, such as a display, at least three colors of light, i.e., red, green, and blue are required to be obtained in order to reproduce full-color images. To achieve this, for example, there are following methods: a method in which a color filter is combined with a light-emitting element emitting light with a light-emitting spectrum in a wide wavelength, a method in which a color conversion layer is combined with a light-emitting element emitting light with a wavelength shorter than a wavelength of an objective color, and a method in which a light-emitting element emitting light with a desired wavelength is used. Among these three methods, the final one, i.e., a method in which an objective color is obtained directly is preferable because loss in energy is small in this method.

This method is employed for the above organic EL televisions which have become commercially available; however, actually, in addition to that method, a color filter is used, and a micro cavity structure is employed for a light-emitting element in order to improve color purity. Organic EL televisions having got many advantages are naturally expected to provide high quality images as a next generation television, and light-emitting elements exhibiting appropriate emission colors are required to meet the expectation.

A light emitted from a light-emitting substance is peculiar to the substance as described above. There are many measures to improve the color purity of an organic EL television, which means that it is very difficult to obtain a light-emitting element which exhibits light emission of a favorable color and also satisfies another important property such as a lifetime or power consumption. In addition, an important property of a light-emitting element, such as a lifetime or power consumption, does not necessarily depend only on a substance exhibiting light emission. The property is greatly affected also by layers other than a light-emitting layer, an element structure, an affinity between a light-emitting substance and a host, or the like. Therefore, it is true that many kinds of materials are necessary for light-emitting elements in order to show the growth of this field. As a result thereof, materials for light-emitting elements which have a variety of molecular structures have been disclosed (for example, see Reference 1).

REFERENCES

Patent Document

[Reference 1] PCT International Publication Ser. No. 07/058,127

DISCLOSURE OF INVENTION

Among light-emitting elements that are developed until now, however, light-emitting elements that emit blue light are inferior in characteristics to light-emitting elements that emit red light to green light, which is a problem. In order to emit blue light, a light-emitting substance having a large energy gap is necessary and a substance used for a host in which the light-emitting substance is dispersed or a substance used for a transporting layer adjacent to a light-emitting region in a light-emitting layer needs to have a larger energy gap, which is one cause of the above problem.

When a material whose energy gap is not large enough is used as a host material or a material for a layer that is adjacent to a light-emitting region, exciton energy transfers to the material; thus, there are problems such as reduction in color purity and luminous efficiency of the light-emitting element. Thus, according to one embodiment of the present invention, it is an object thereof to provide a novel triarylamine derivative which has large energy gap and can be used for a transporting layer or a host material of a light-emitting element.

The inventors of the present invention was able to synthesize a triarylamine derivative whose energy gap is large and carrier transporting property is appropriate, in which one or two naphthyl groups are bonded to central nitrogen through a phenylene group or a biphenylene group as a substance that can be used preferably as a material of a light-emitting element.

In other words, a triarylamine derivative according to one embodiment of the present invention is a triarylamine derivative represented by a general formula (G1) given below.

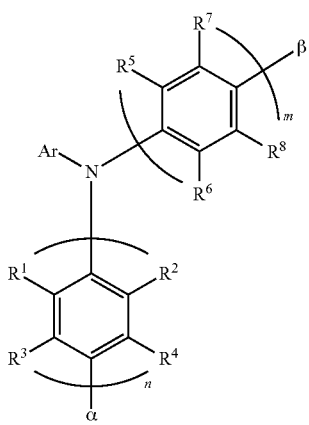
(G1)

In the formula, Ar represents either a substituted or unsubstituted phenyl group or a substituted or unsubstituted biphenyl group; α represents a substituted or unsubstituted naphthyl group; and β represents either hydrogen or a substituted or unsubstituted naphthyl group. In addition, n and m each independently represent 1 or 2; and $R^1$ to $R^8$ each independently represent any of hydrogen, an alkyl group having 1 to 6 carbon atoms, or a phenyl group.

Specifically, as Ar in the formula, groups represented by structural formulae (Ar-1) to (Ar-4) below are given.

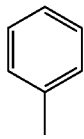
(Ar-1)

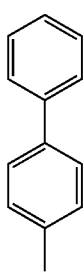
(Ar-2)

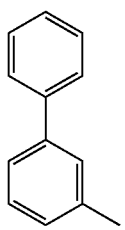
(Ar-3)

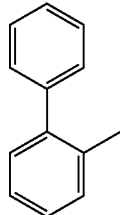
(Ar-4)

Specifically, as α in the formula, groups represented by structural formulae (α-1) and (α-2) below are given.

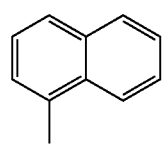
(α-1)

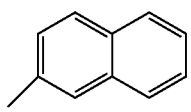
(α-2)

Specifically, as β in the formula, groups represented by structural formulae (β-1) to (β-3) below are given.

H (β-1)

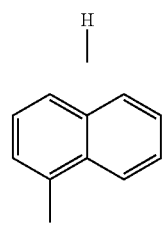
(β-2)

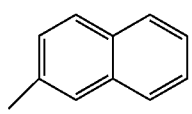
(β-3)

The triarylamine derivative according to one embodiment of the present invention having any of the above structural formulae is a novel triarylamine derivative which has large energy gap and can be used for a transporting layer or a host material of a light-emitting element. In other words, the triarylamine derivative according to one embodiment of the present invention, which has large energy gap or in which there is an energy difference (hereinafter also referred to as triplet energy) between a ground state and a triplet excited state, can be very preferably used as a host material or a carrier transporting material (especially as a hole transporting material) of a light-emitting element providing blue fluorescence or a light-emitting element providing green phosphoresce. Therefore, the triarylamine derivative according to one embodiment of the present invention can be used as a host material or a carrier transporting material of a light-emitting substance having emission wavelengths in a wide visible region (from blue light to red light), whereby light can be emitted efficiently. In addition, in the case of a light-emitting device including a plurality of red, green, and blue pixels, a host material or a carrier transporting material can have the same kind also in a process of forming a light-emitting element; therefore, the process can be simplified and the use efficiency of the material is also high, which are preferable.

BRIEF DESCRIPTION OF DRAWINGS

In the accompanying drawings.

BEST MODE FOR CARRYING OUT THE INVENTION

Figure 1A:
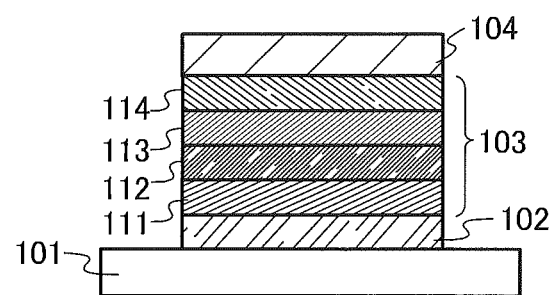
FIGS. 1A and 1B are conceptual views of light-emitting elements (Embodiments 3 to 5)

Embodiments of the present invention will be described hereinafter. However, the present invention can be implemented in various modes, and it is easily understood by those skilled in the art that modes and details thereof can be modified in various ways without departing from the spirit and the scope of the present invention. Therefore, the present invention should not be interpreted as being limited to the description of the embodiments below.

Embodiment 1

A triarylamine derivative in this embodiment is the triarylamine derivative in which the naphthyl group represented by a, which is described above, is bonded to central nitrogen through a phenylene group or a biphenylene group. The triarylamine derivative has one or two structures in which the above naphthyl group is bonded to central nitrogen through a phenylene group or a biphenylene group. When there are two naphthyl groups, the second naphthyl group corresponds to β in the above general formula (G1). Note that the substitution position where the second naphthyl group is bonded to a phenylene group or a biphenylene group may be a 1-position or a 2-position. In addition, the naphthyl group may further have a substituent.

In addition, in the triarylamine derivative in this embodiment, as for one or two bonds among three bonds of the central nitrogen atom, a phenylene group or a biphenylene group, with which a naphthyl group is bonded, is bonded to one or two bonds; and the rest of two or one bond is bonded to a phenyl group or a biphenyl group. In addition, the phenylene group or biphenylene group may further have a substituent.

The triarylamine derivative of this embodiment having such a structure has an adequate hole transporting property and a wide energy gap at the same time, and the triarylamine derivative is a substance that can be very preferably used as a material for a light-emitting element emitting blue light.

The triarylamine derivative of this embodiment as described above can also be represented by a general formula (G1) given below.

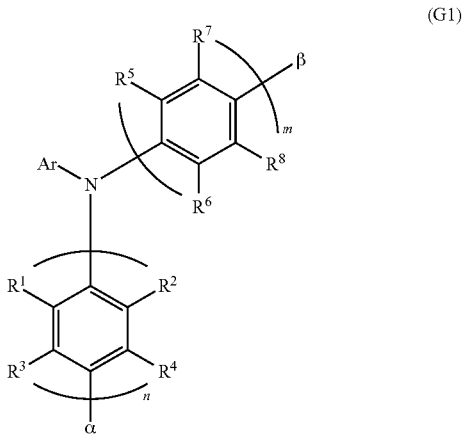

In the formula, Ar represents either a phenyl group or a biphenyl group; α represents a naphthyl group; and β represents either hydrogen or a naphthyl group. Alternatively, the Ar, α, and β each may have another one or a plurality of substituents. As the substituent, an alkyl group having 1 to 6 carbon atoms and a phenyl group can be given. Note that when the substituent is an alkyl group having 1 to 6 carbon atoms, not only a non-cyclic alkyl group but also a cyclic alkyl group may be used.

In addition, n and m each independently represent 1 or 2. In other words, when n and m each represent 1, they each represent a phenylene group, and when n and m each represent 2, they each represent a biphenylene group. Further, $R^1$ to $R^8$ each independently represent any of hydrogen, an alkyl group having 1 to 6 carbon atoms, or a phenyl group. When $R^1$ to $R^8$ are each an alkyl group having 1 to 6 carbon atoms, not only non-cyclic alkyl group but also a cyclic alkyl group may be used.

Note that when n or m represents 2, $R^1$ to $R^8$ may be different between a phenylene group bonded to amine and a phenylene group bonded to the phenylene group. In other words, when n or m represents 2, although the group in the parenthesis of the above general formula (G1) is a biphenylene group in which two phenylene groups are bonded, the case where the bonded two phenylene groups have different substituents is also included.

Specifically, as Ar in the formula, groups represented by structural formulae (Ar-1) to (Ar-4) below are given.

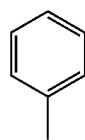
(Ar-1)

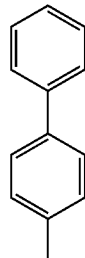
(Ar-2)

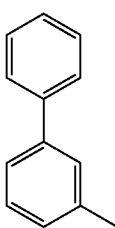
(Ar-3)

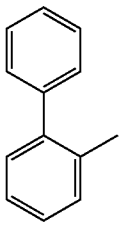
(Ar-4)

Specifically, as α in the formula, groups represented by structural formulae (α-1) and (α-2) below are given.

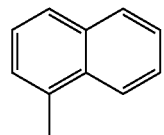
(α-1)

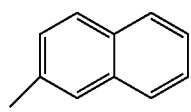
(α-2)

Specifically, as β in the formula, groups represented by structural formulae (β-1) to (β-3) below are given.

(β-1)
H

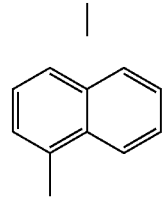
(β-2)

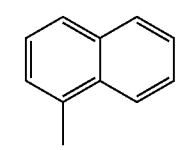
(β-3)

Specifically, as $R^1$ to $R^8$ in the formula, groups represented by structural form (β-1) to (β-9) below are given.

—CH₃ (R-1)

$\begin{array}{c}CH_3\\ \diagup\\ —CH_2\end{array}$ (R-2)

$\begin{array}{c}CH_3\\ |\\ —C—CH_3\\ |\\ H_3C\end{array}$ (R-3)

$\begin{array}{c}H_3C\\ \diagdown\\ CH—CH_3\\ \diagup\\ —CH_2\end{array}$ (R-4)

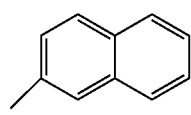
(R-5)

$\begin{array}{c}CH_3\\ |\\ H_2C\diagdown CH_2\\ |\quad\quad |\\ H_2C\diagdown CH_2\\ \diagup\\ —CH_2\end{array}$ (R-6)

(R-7)
(R-8)
—H (R-9)
As specific examples of the triarylamine derivative represented by the general formula (G1), there are triarylamine derivatives represented by structural formulae (1) to (87) given below. However, the present invention is not limited to these examples.
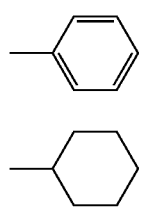
(1)
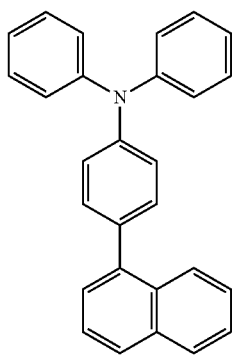
(2)
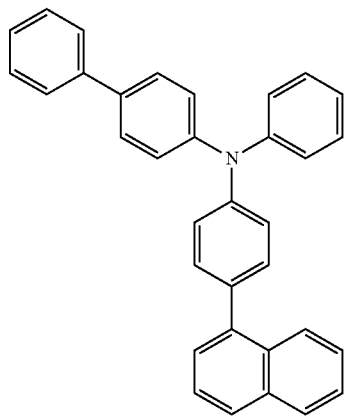
(3)
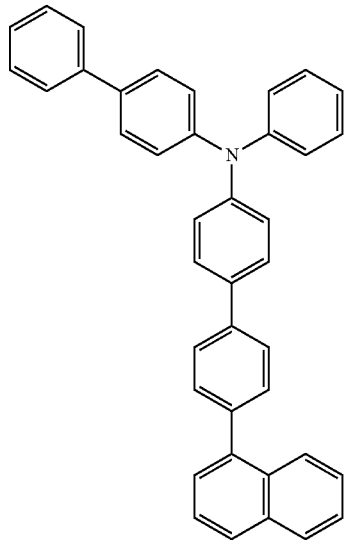
(4)
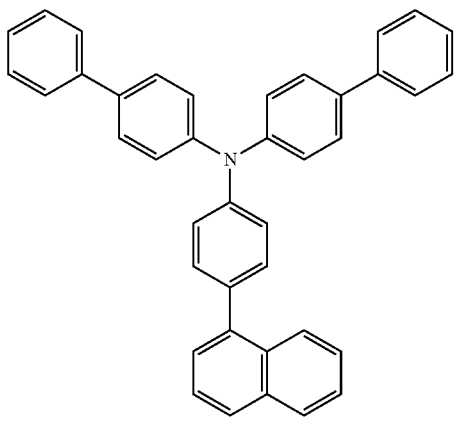
(5)

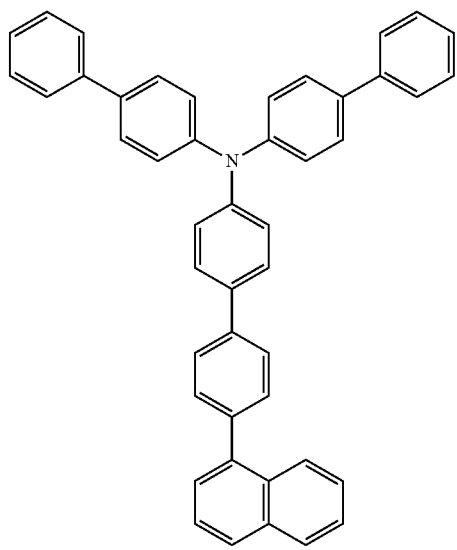
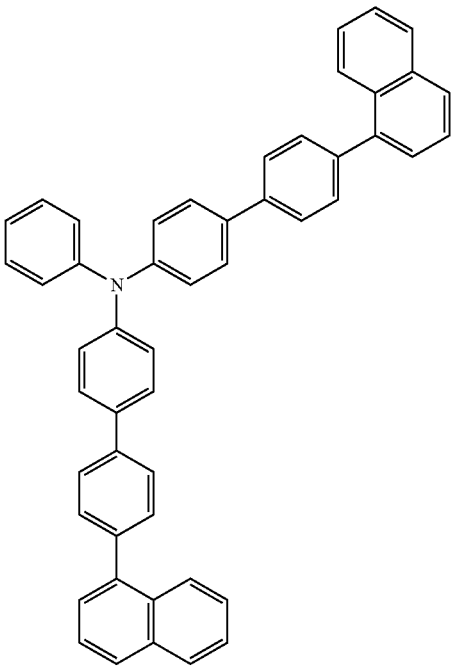
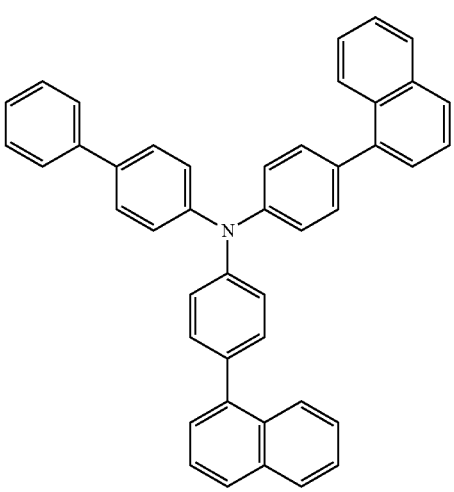

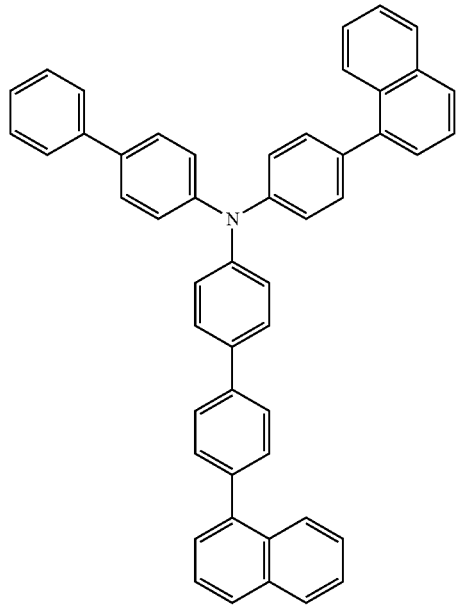
(11)
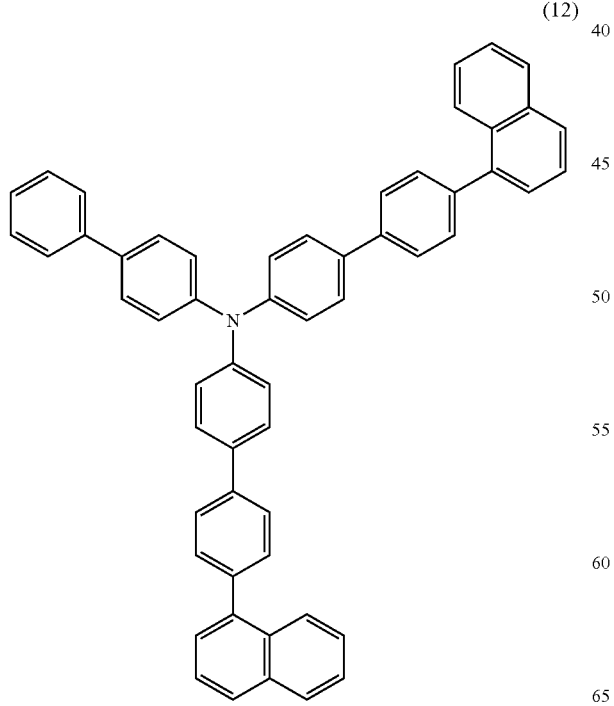
(12)
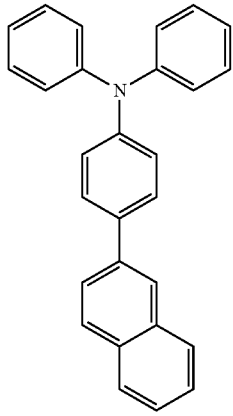
(13)
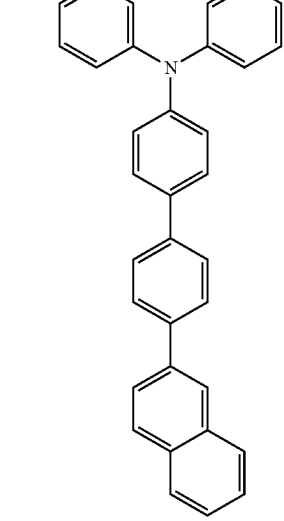
(14)
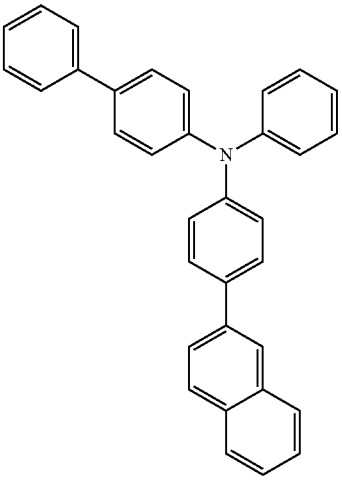
(15)

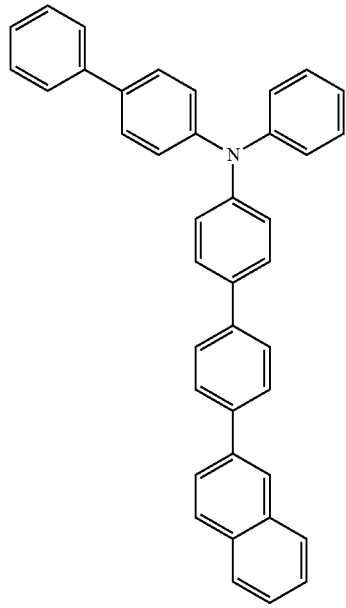
(16)
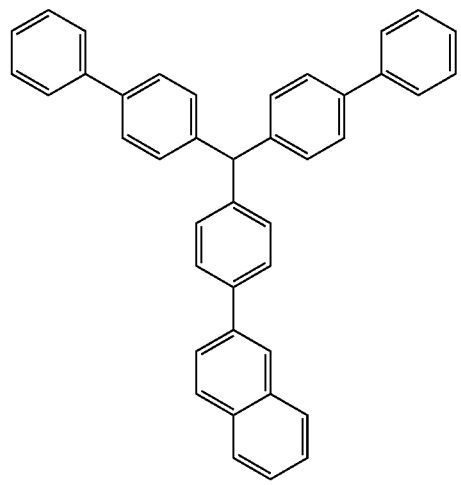
(18)
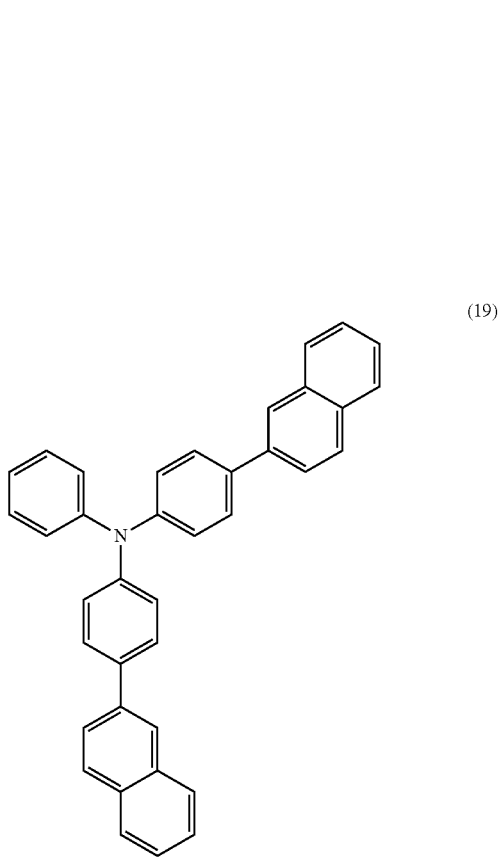 [SMILES: c1ccc(N(c2ccc(-c3ccc4ccccc4c3)cc2)c2ccc(-c3ccc4ccccc4c3)cc2)cc1]
(17)
(19)

(20)
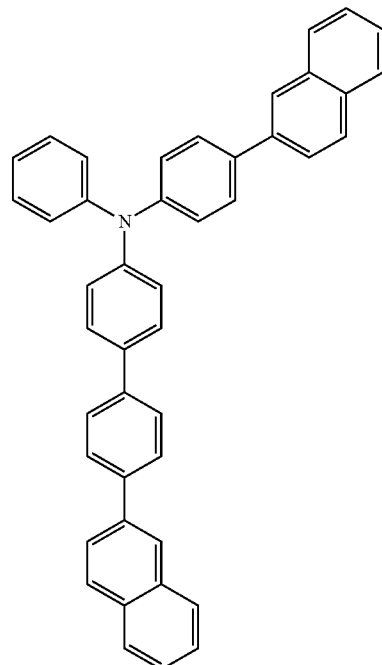
(21)
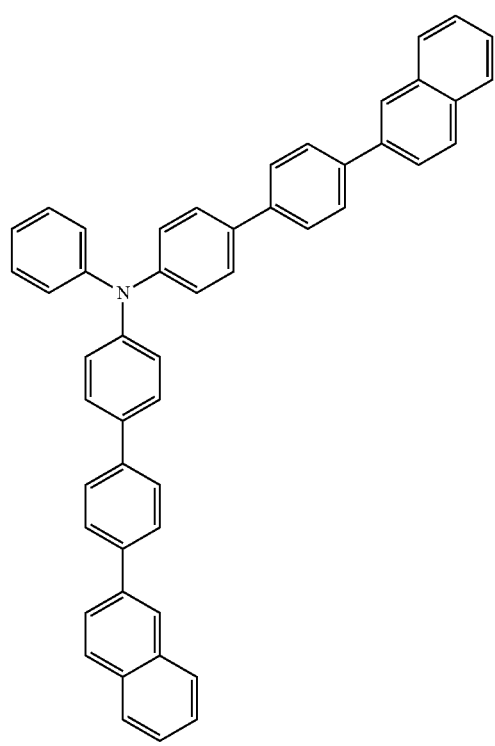
(22)
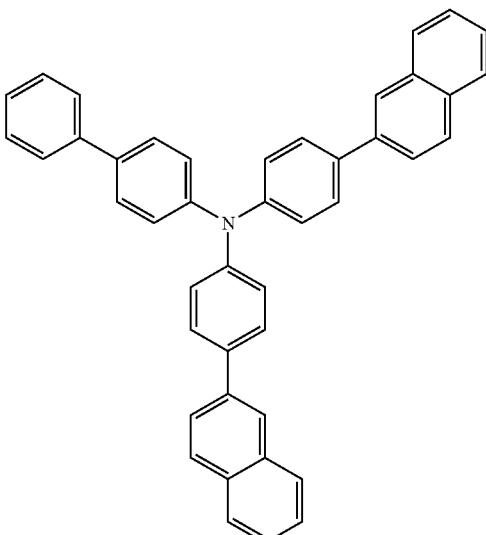
(23)
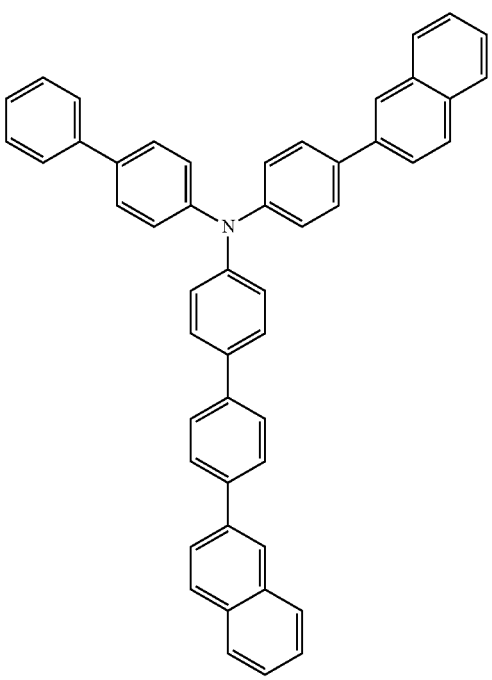

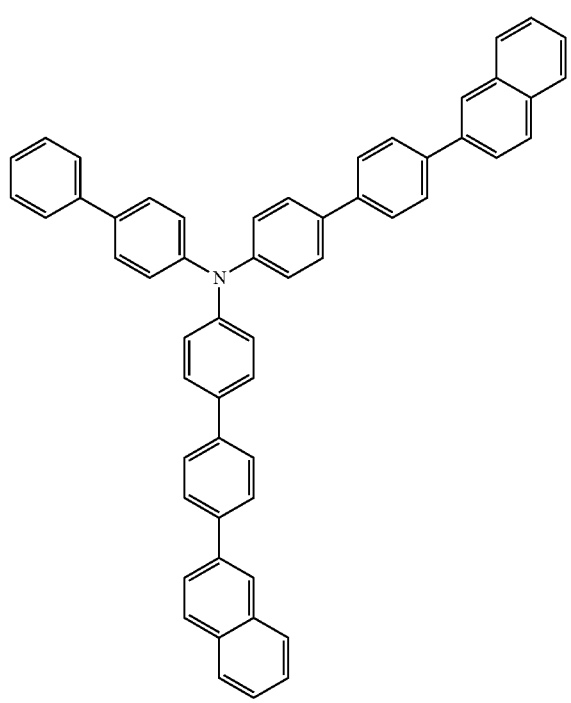
(24)
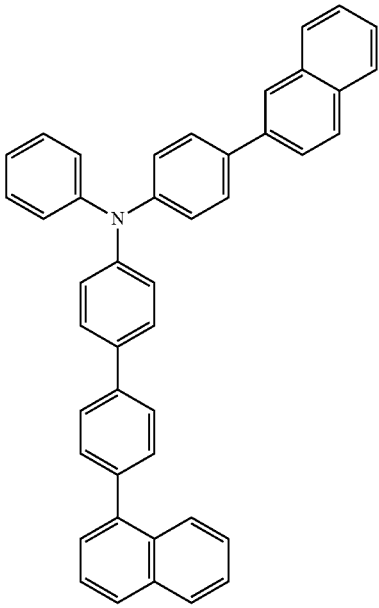
(26)
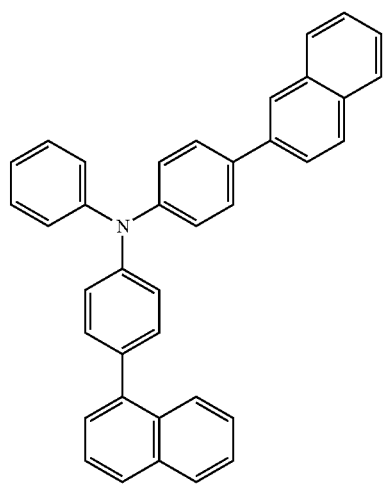
(25)
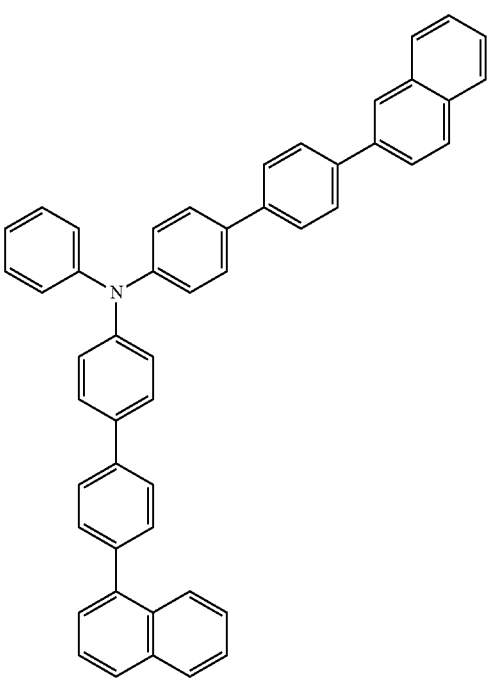
(27)

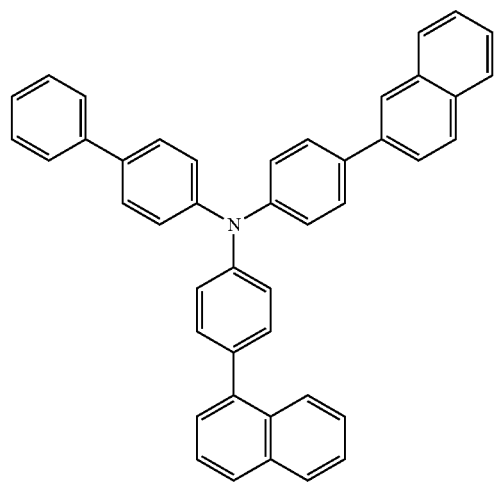
(28)
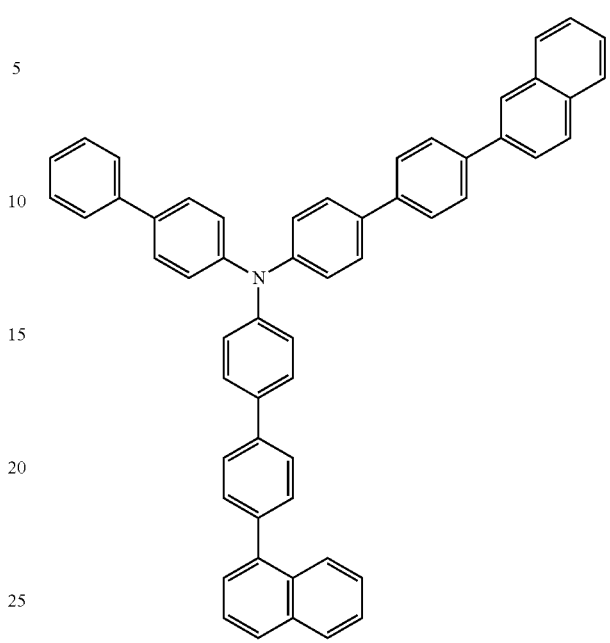
(30)
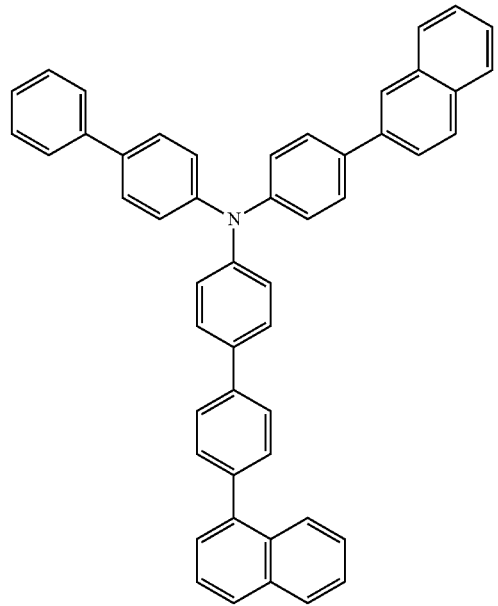
(29)
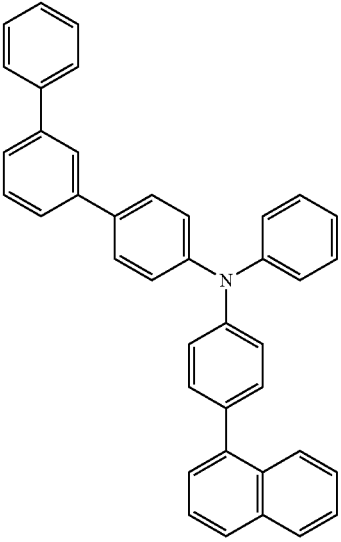
(31)

(32)
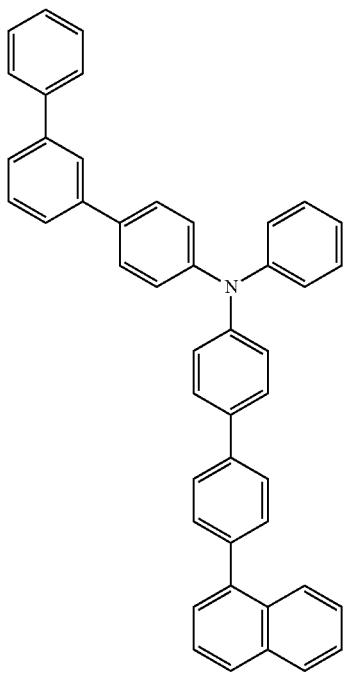
(34)
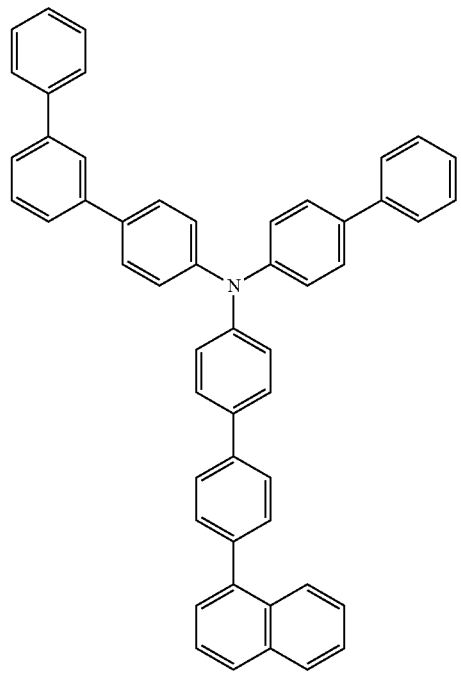
(33)
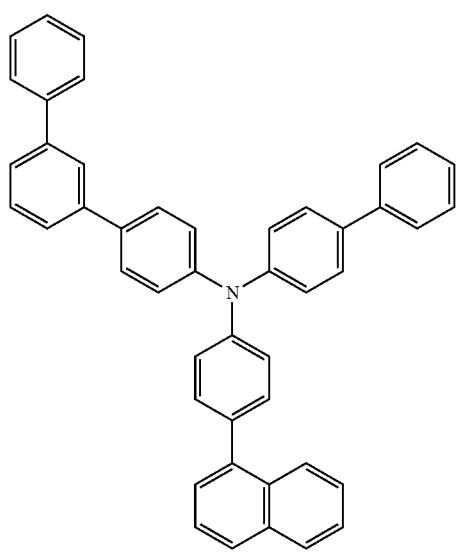
(35)
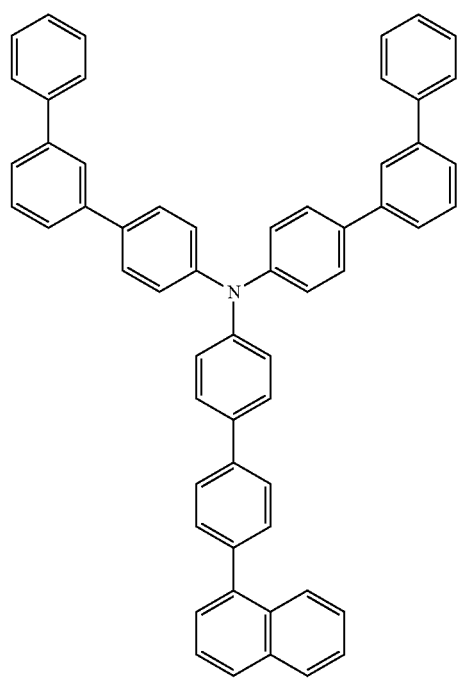

(36)
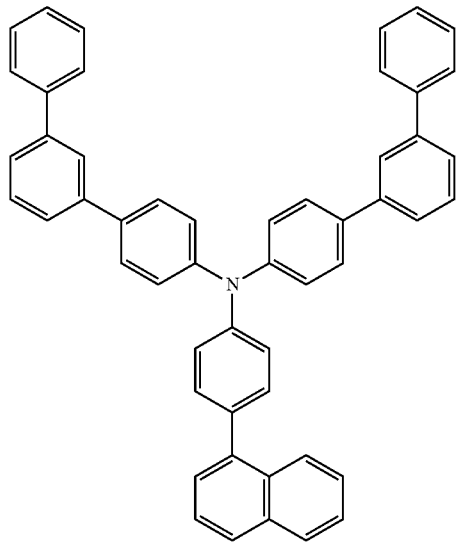
(37)
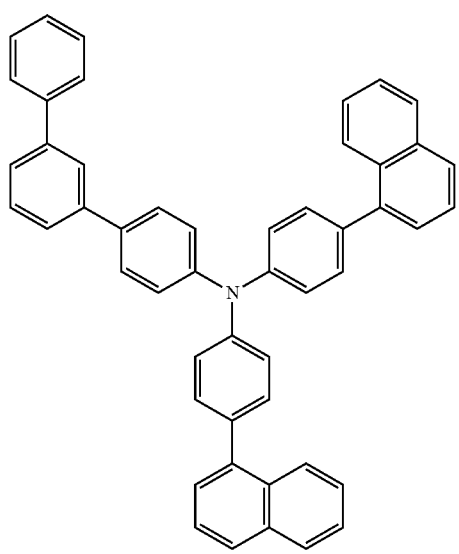
(38)
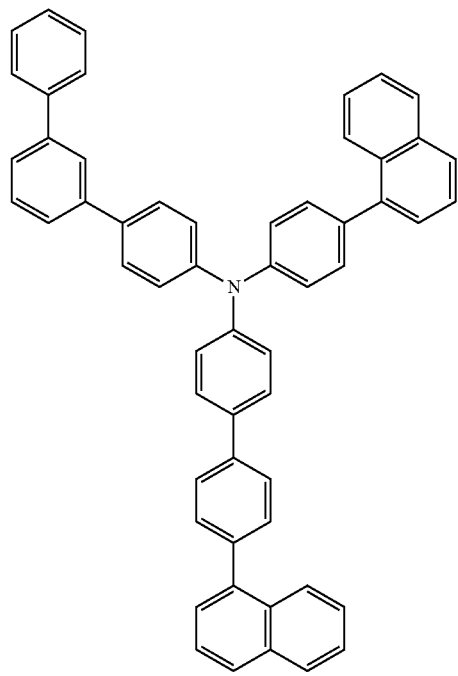
(39)
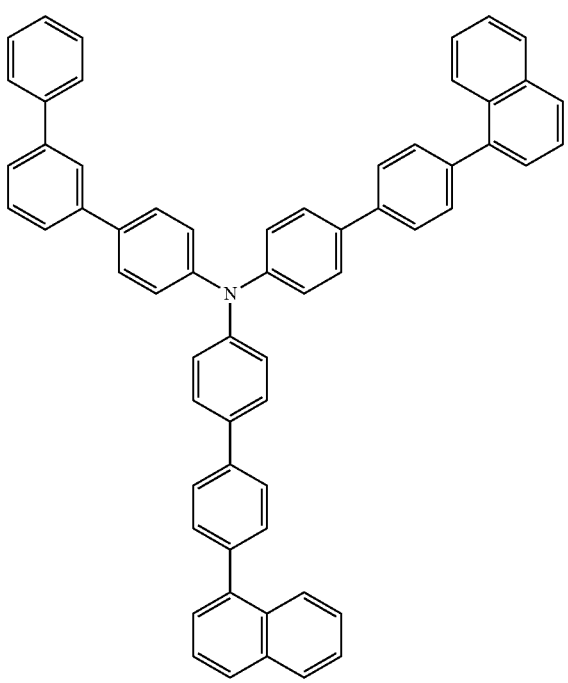

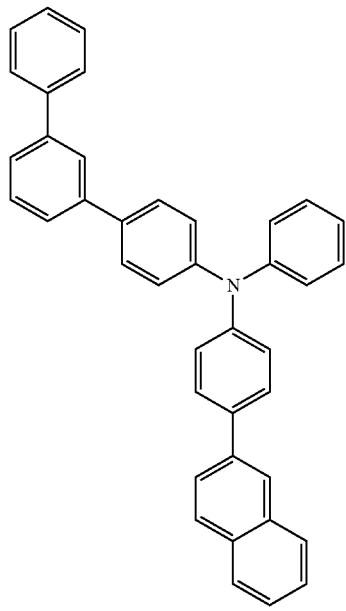
(40)
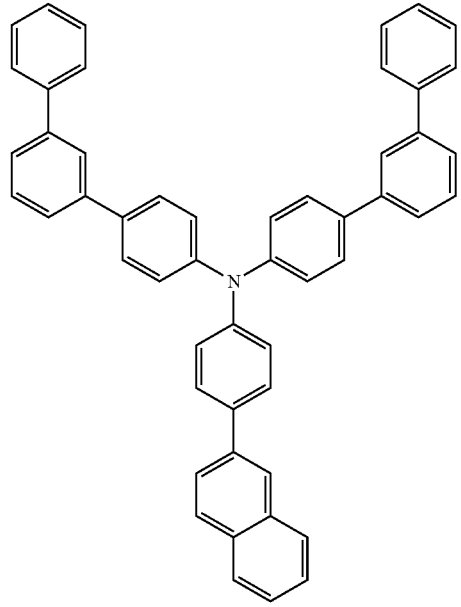
(42)
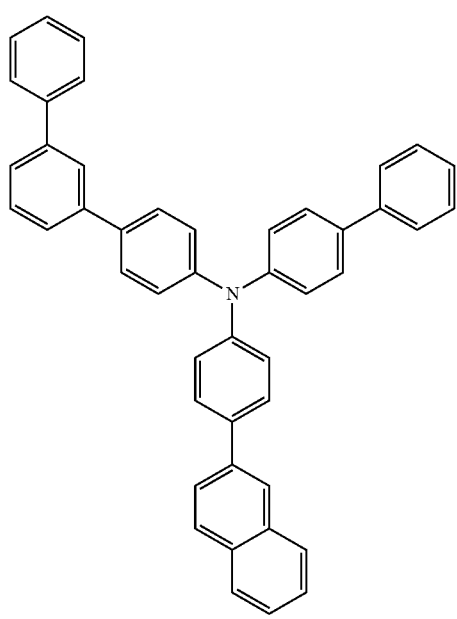
(41)
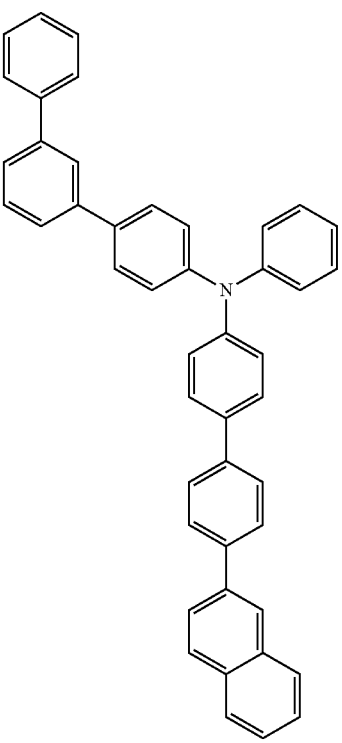
(43)

(44)
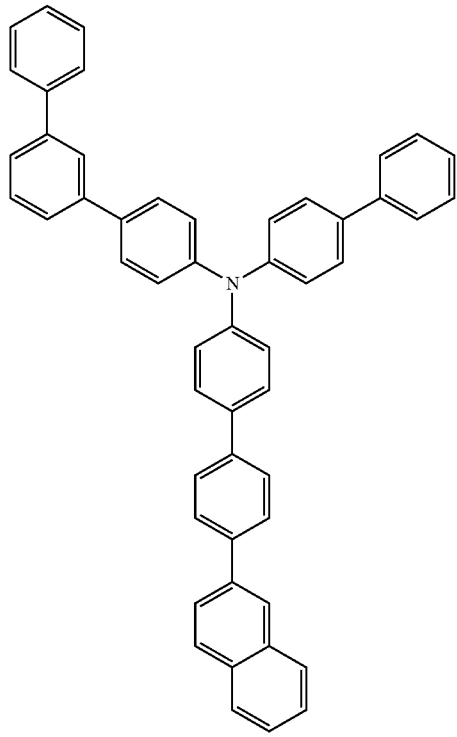
(45)
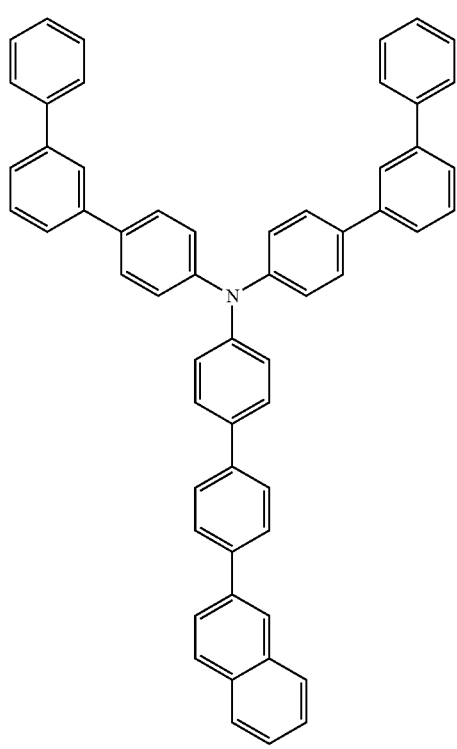
(46)
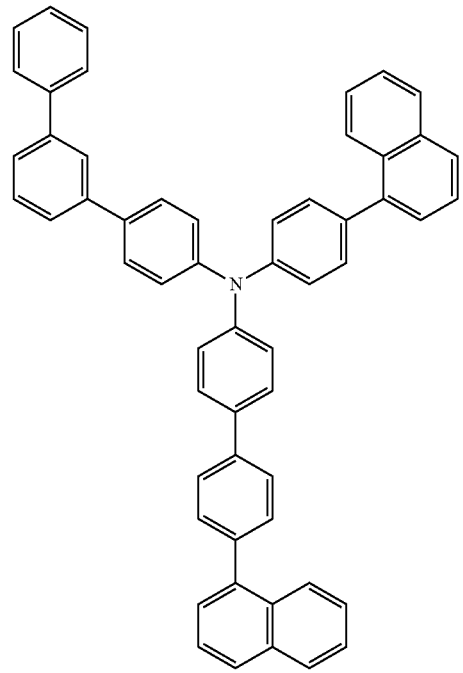
(47)
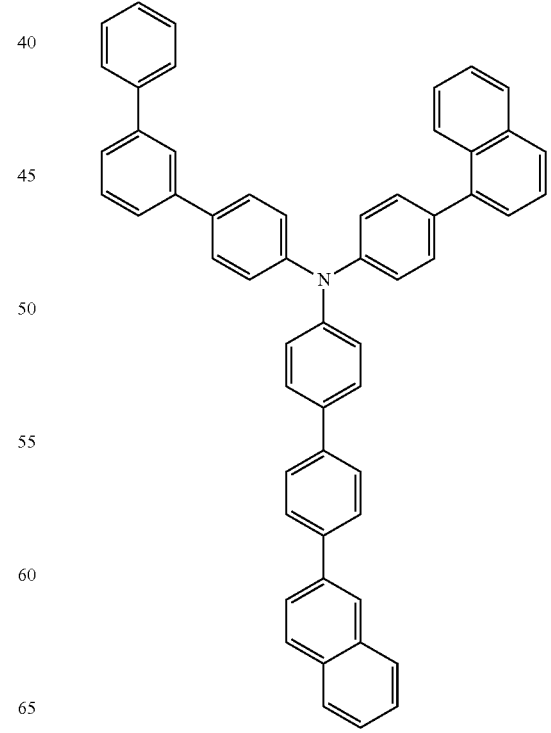

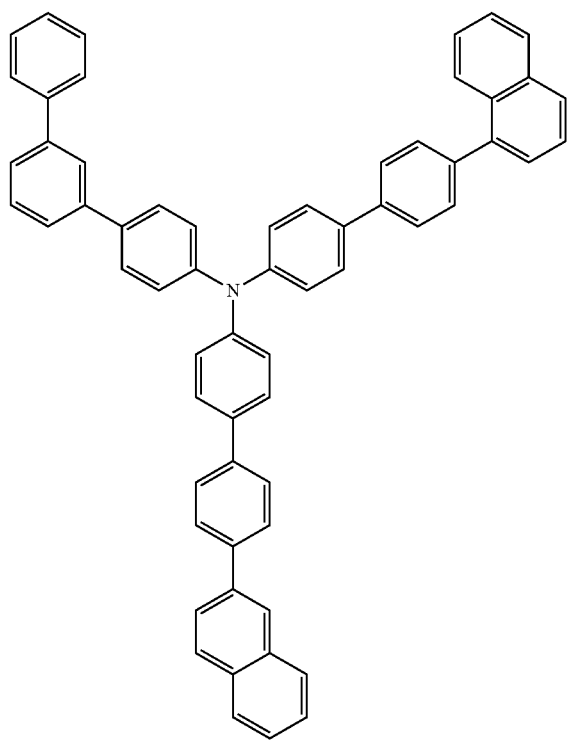
(48)
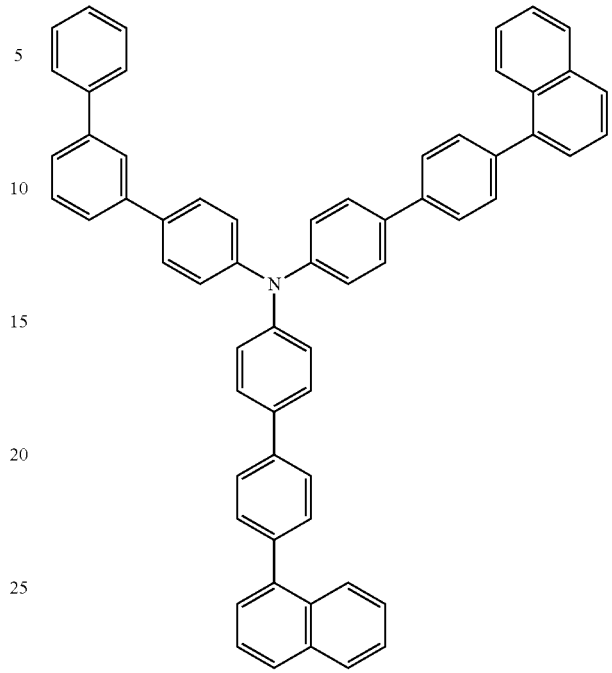
(50)
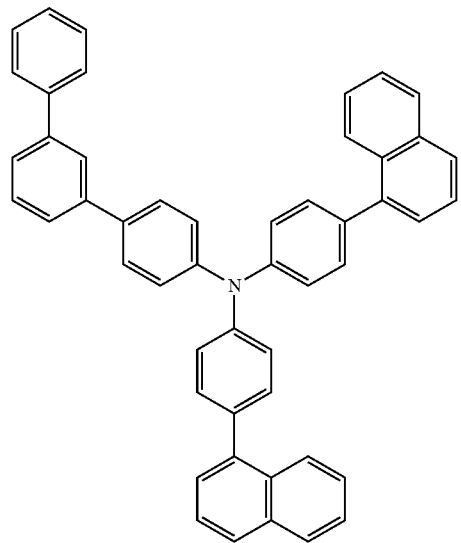
(49)
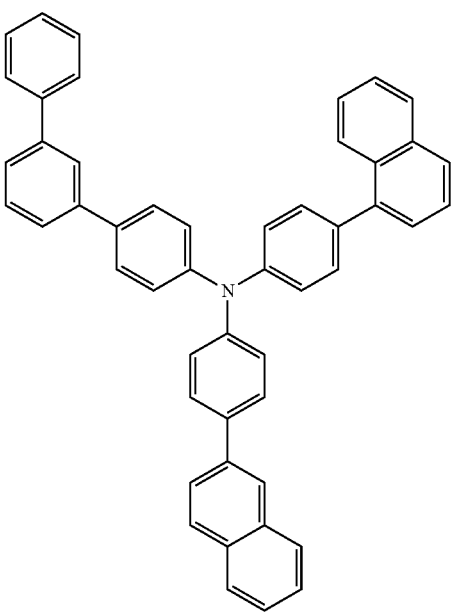
(51)

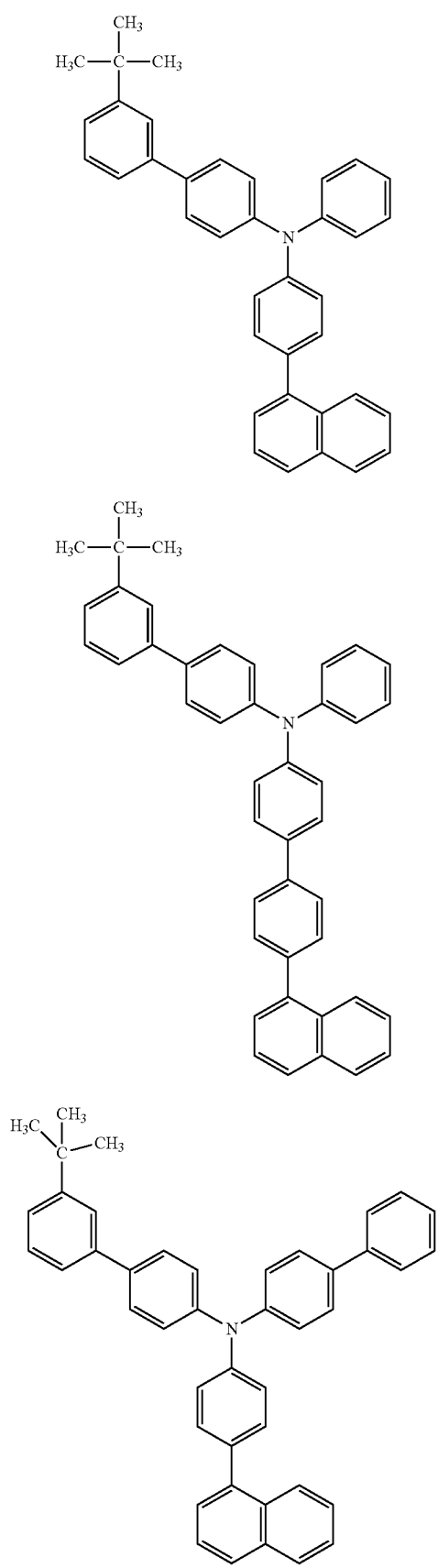
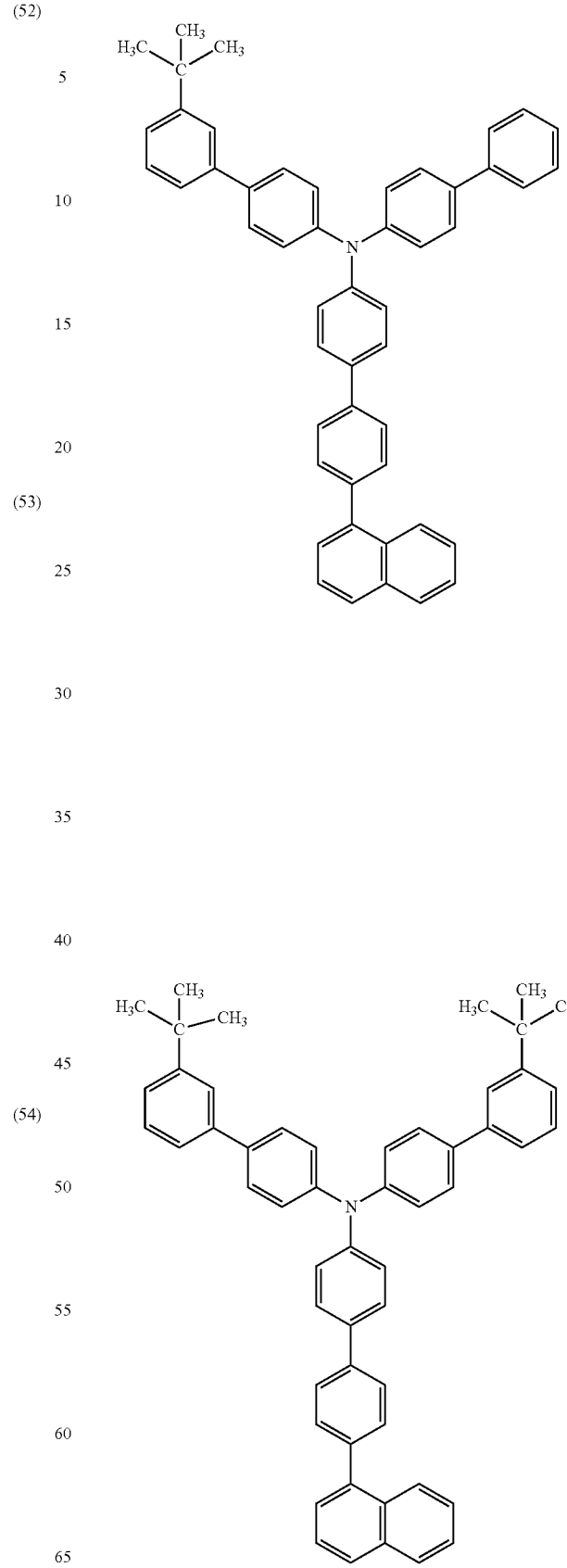

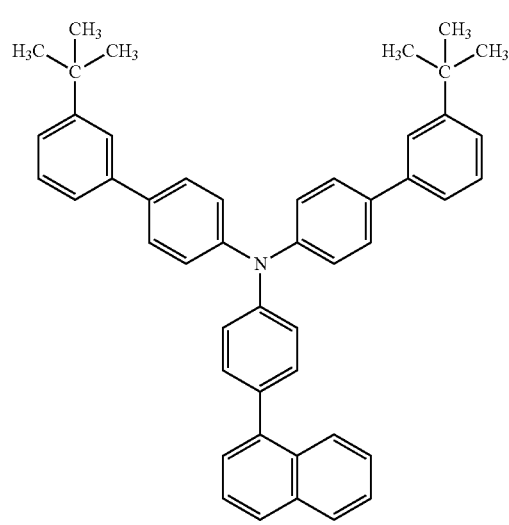
(57)
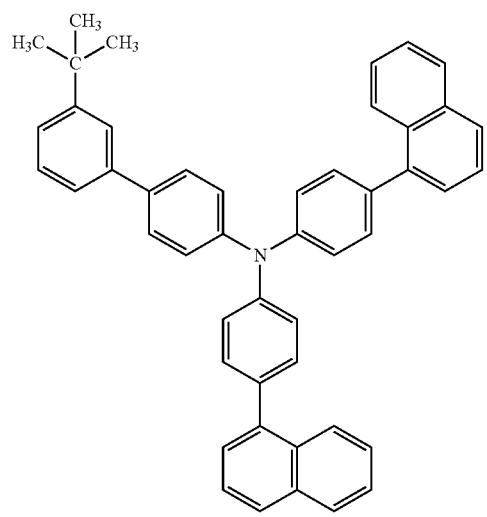
(58)
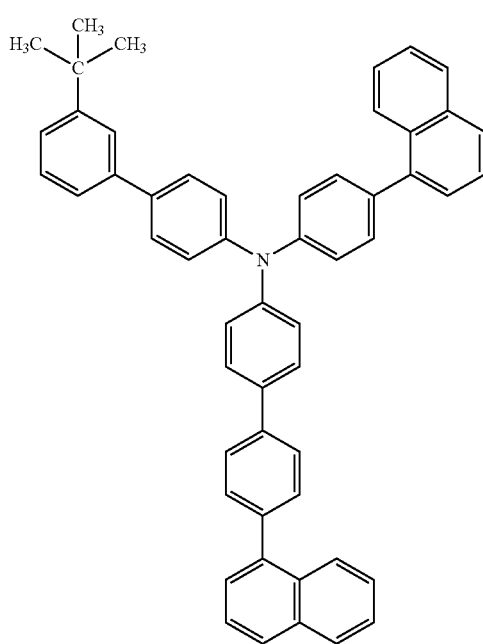
(59)
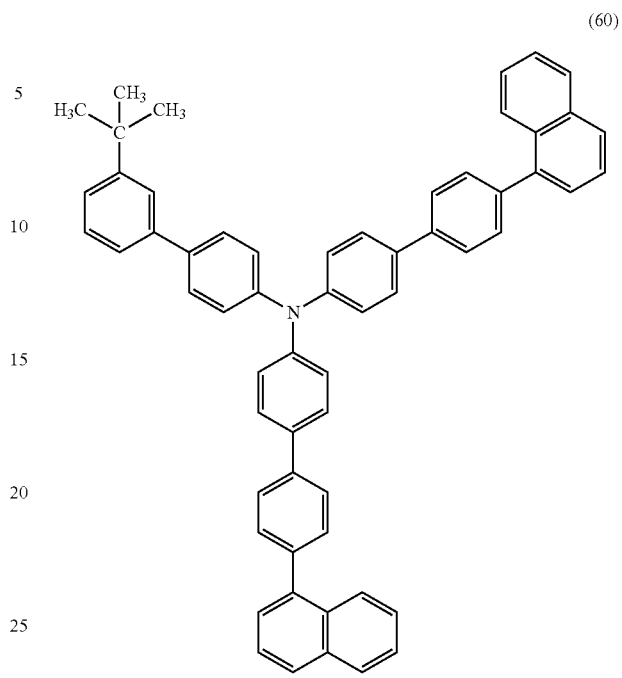
(60)
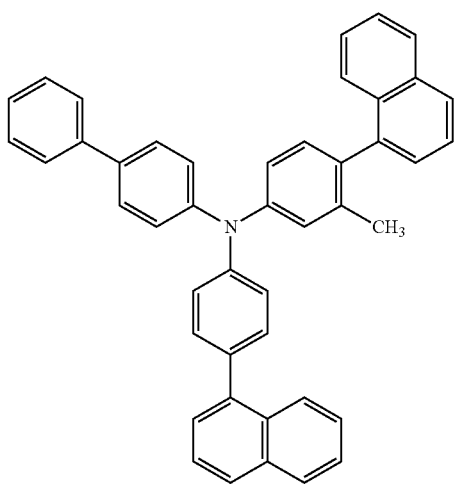
(61)

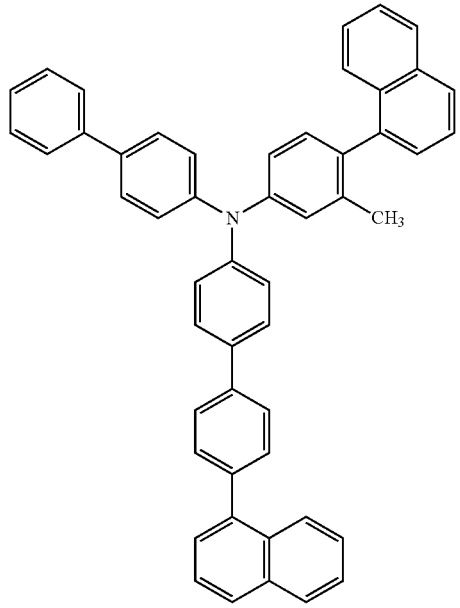
(62)
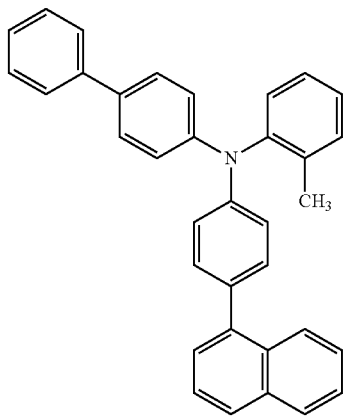
(64)
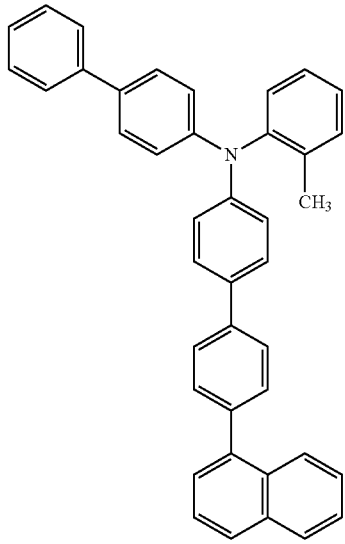
(65)
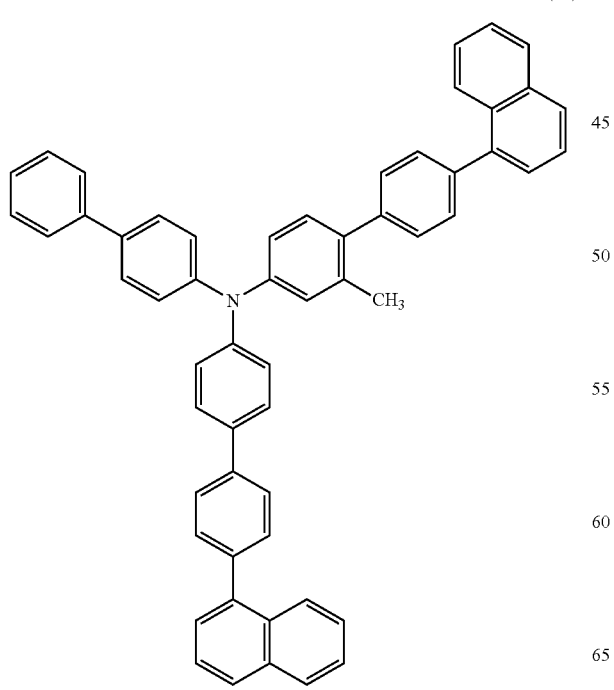
(63)
(66)

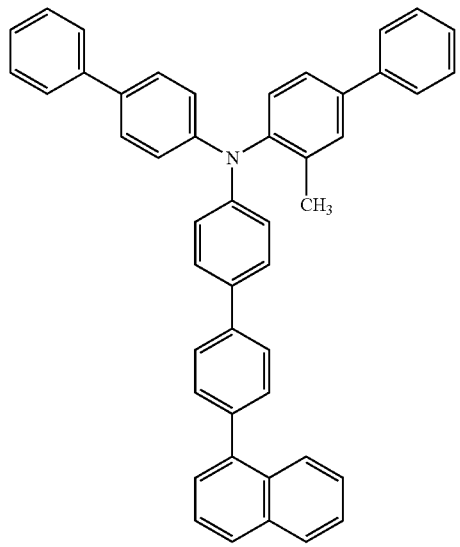
(67)
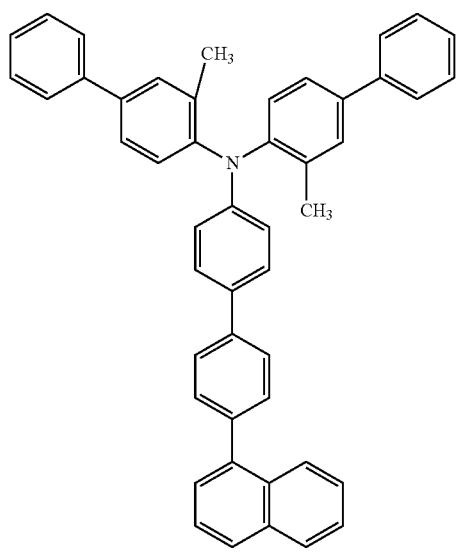
(68)
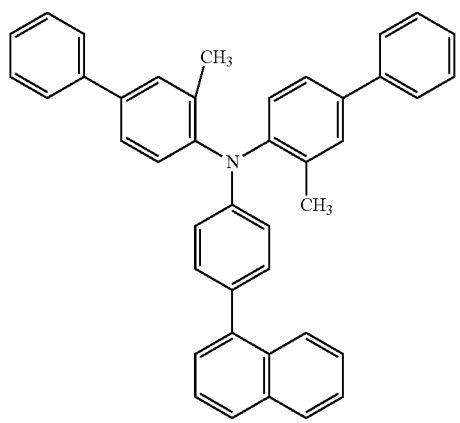
(69)
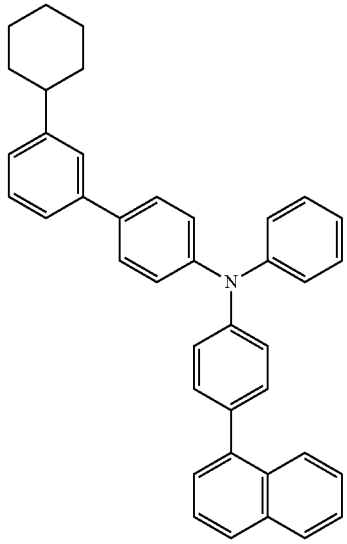
(70)
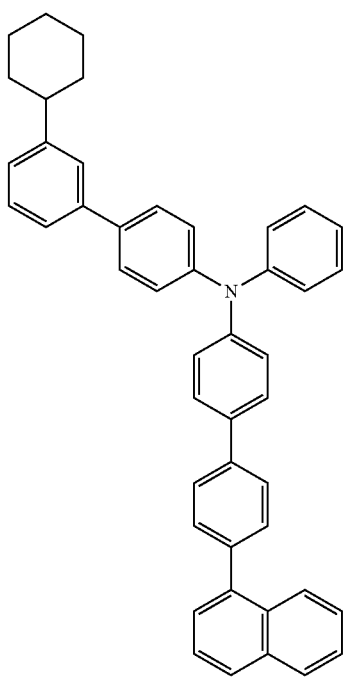
(71)

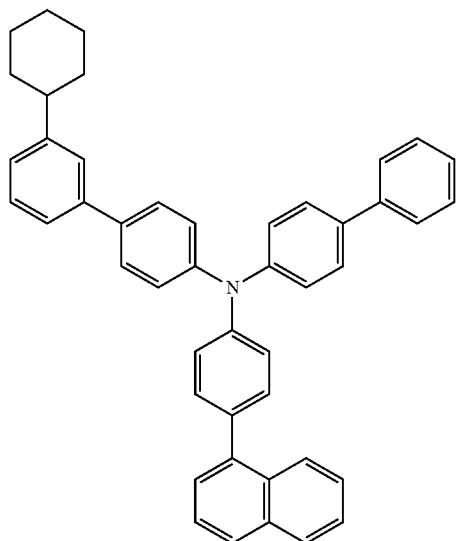 (72)
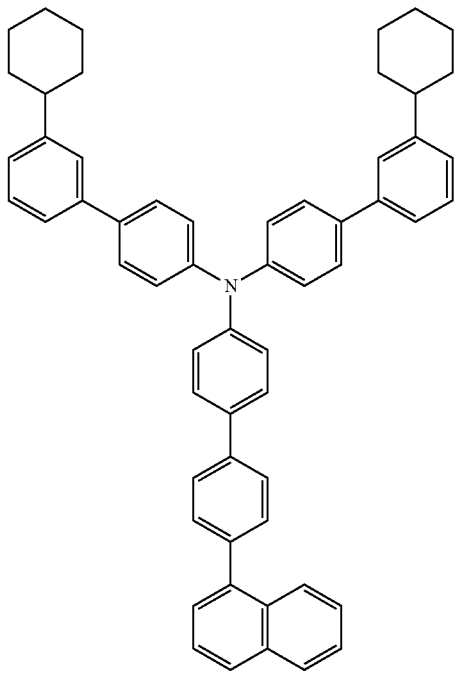 (74)
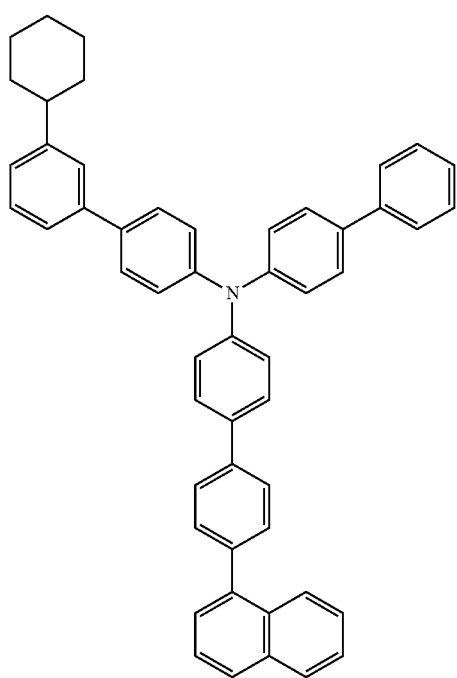 (73)
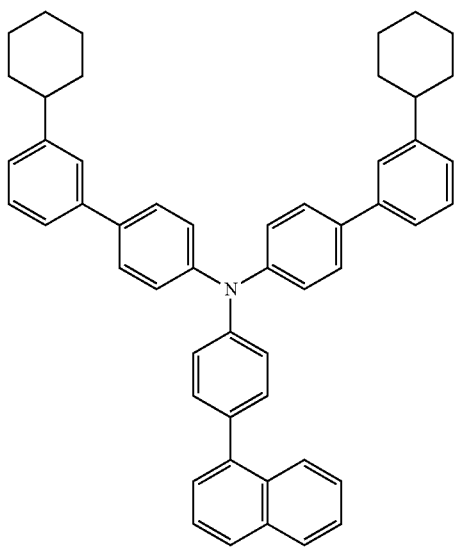 (75)

(76)
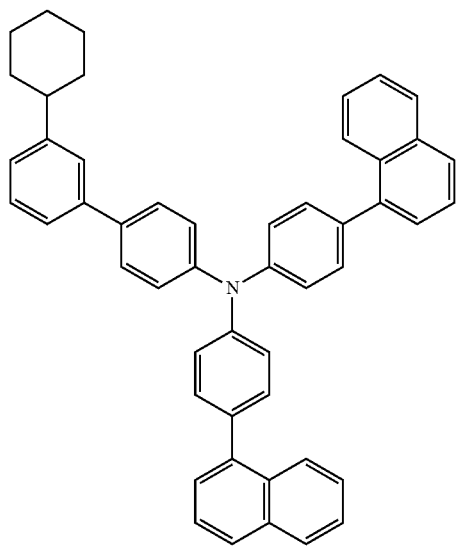
(78)
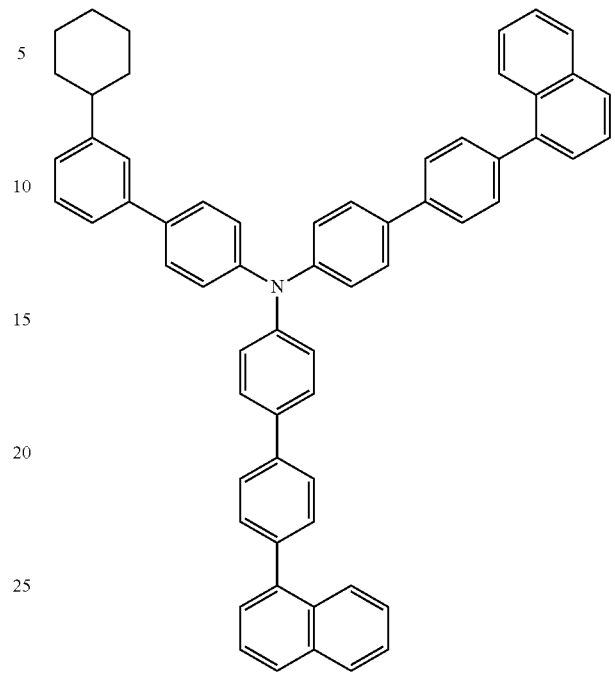
(77)
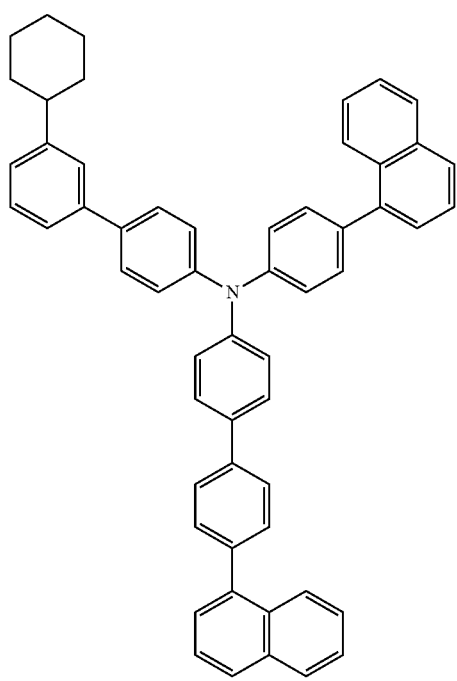
(79)
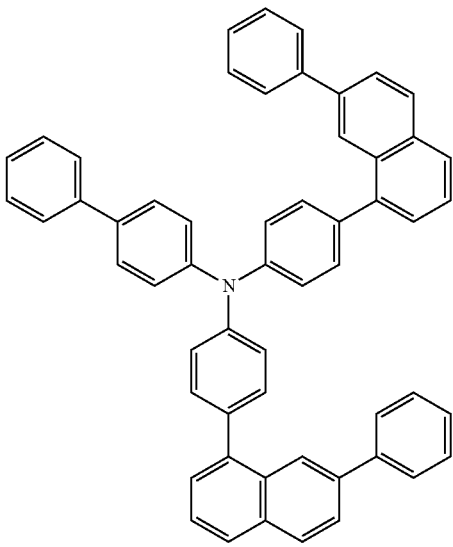

(80)
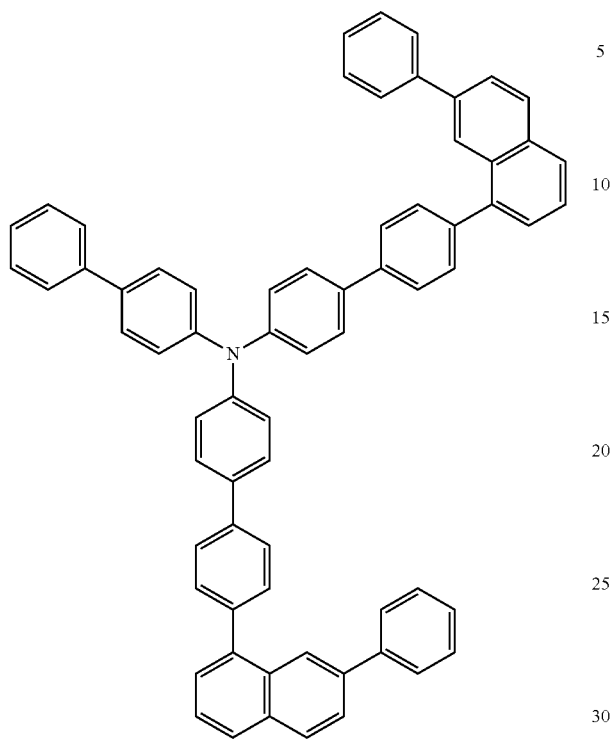
(81)
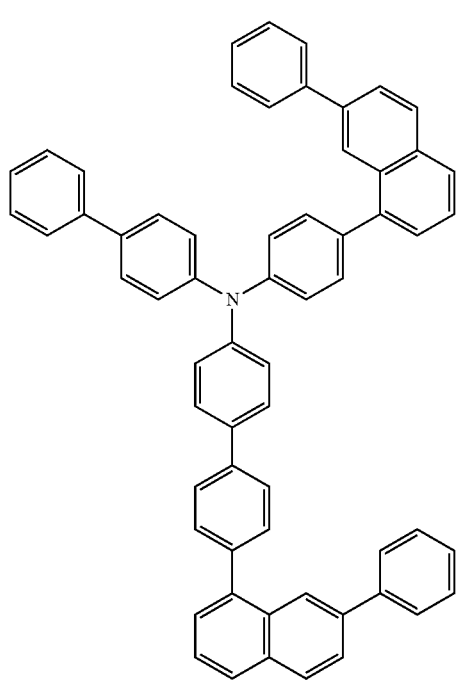
(82)
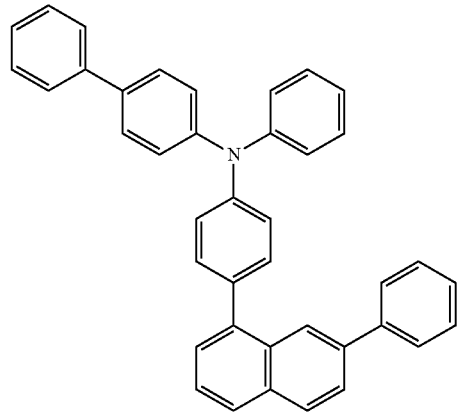
(83)
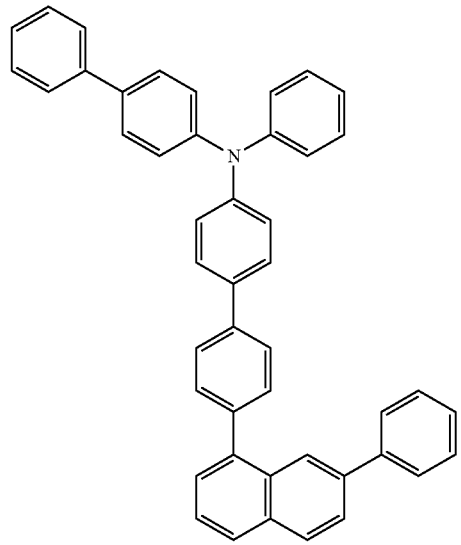
(84)
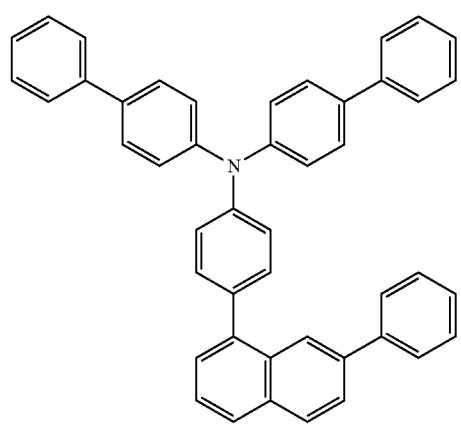

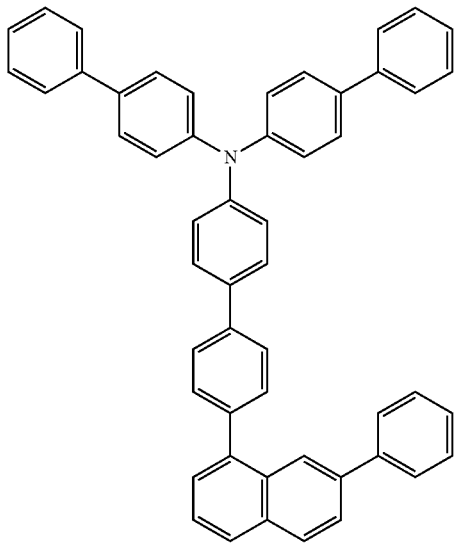

(85)

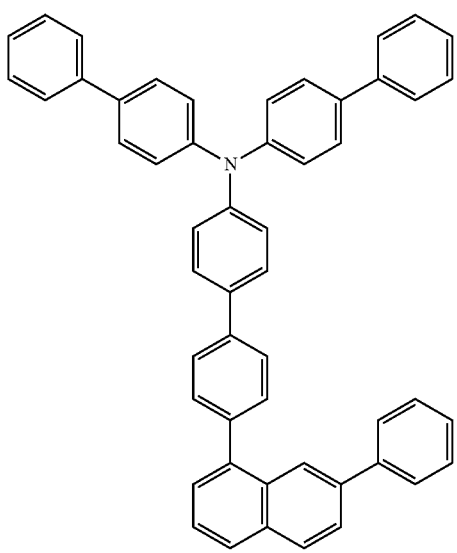

(86)

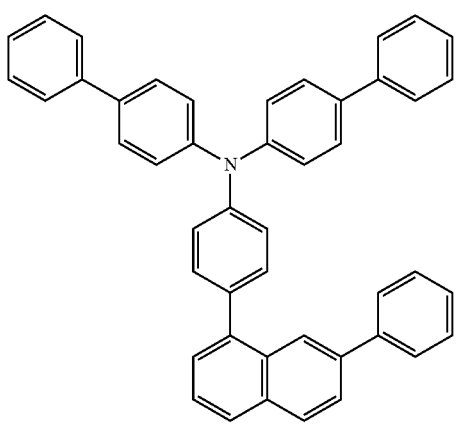

(87)

The triarylamine derivative in this embodiments as described above, which has large energy gap or in which there is an energy difference (hereinafter also referred to as triplet energy) between a ground state and triplet excited state, can be very preferably used as a host material or a carrier transporting material (especially as a hole transporting material) of a light-emitting element providing blue fluorescence or a light-emitting element providing green phosphoresce. Therefore, the triarylamine derivative in this embodiment can be used as a host material or a carrier transporting material of a light-emitting substance having emission wavelengths in a wide visible region (from blue light to red light), whereby light can be emitted efficiently. In addition, in the case of a light-emitting device including a plurality of red, green, and blue pixels, a host material or a carrier transporting material can have the same kind also in a process of forming a light-emitting element; therefore; the process can be simplified and the use efficiency of the material is also high, which are preferable.

Embodiment 2

Subsequently, a synthetic method of the triarylamine derivative described in Embodiment 1 will be shown in this embodiment <Synthetic Method 1>

In this synthetic method, the following compound M which is the triarylamine derivative described in Embodiment 1 is synthesized by two methods, <Synthetic Method 1-1> and <Synthetic Method 1-2>. First, the above compound M is synthesized by Reaction Scheme (A-1) in this synthetic method. Reaction Scheme (A-1) shows a synthetic method of the above compound M through coupling with secondary arylamine (a compound D1) and coupling with an arylboronic acid, with dihalogenated aryl (a compound E2) used as a starting material. Note that the compound D1 is secondary arylamine in which an aryl group represented by Ar and an aryl group having § are bonded to central nitrogen.

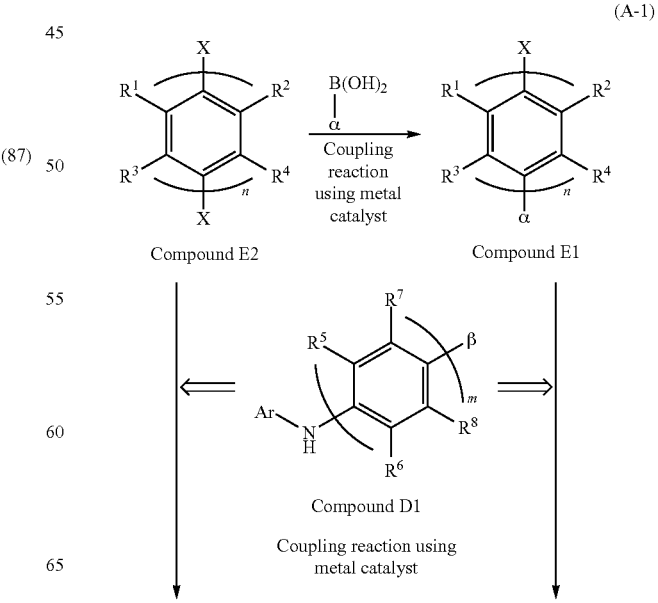

(A-1)

-continued

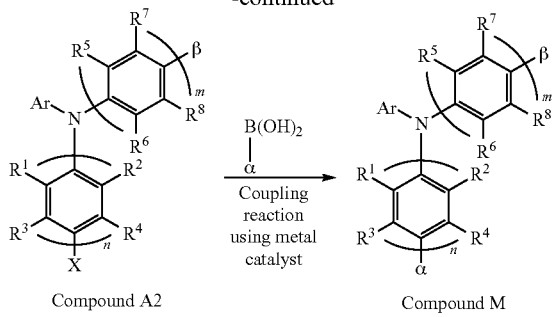

Compound A2 → Compound M (Coupling reaction using metal catalyst, B(OH)₂)

In the synthetic method by Reaction Scheme (A-1), either the secondary arylamine (the compound D1) or an arylboronic acid may be coupled first with the halogenated aryl (the compound E2).

<Synthetic Method 1-1>

Here, a method in which the dihalogenated aryl (the compound E2) and the secondary arylamine (the compound D1) are coupled to synthesize tertiary arylamine and then the tertiary arylamine is coupled with an arylboronic acid is shown.

In order to couple the secondary arylamine (the compound D1) and the halogenated aryl (the compound E2), a synthetic method using a metal catalyst in the presence of a base can be applied. Accordingly, a compound A2 which is tertiary arylamine can be synthesized. The compound A2 is tertiary arylamine in which an aryl group represented by Ar, an aryl group having β, and an aryl group having a halogen group represented by X are bonded to central nitrogen.

The case of using a Buchwald-Hartwig reaction in the above reaction is shown. As a palladium catalyst which can be used as a metal catalyst, bis(dibenzylideneacetone)palladium(0), palladium(II) acetate, and the like can be given. As a ligand in the above palladium catalyst, tri(tert-butyl)phosphine, tri(n-hexyl)phosphine, tricyclohexylphosphine, 1,1-bis(diphenylphosphino)ferrocene (abbreviation: DPPF), and the like can be given. As a substance which can be used as the base, an organic base such as sodium tert-butoxide, an inorganic base such as potassium carbonate, and the like can be given. In addition, the above reaction is preferably performed in a solution, and toluene, xylene, benzene, and the like can be given as a solvent that can be used in the above reaction. However, the catalyst, ligand, base, and solvent which can be used are not limited thereto.

The case of using the Ullmann reaction in the above reaction is shown. A copper catalyst can be used as the metal catalyst, and copper iodide (1) and copper acetate (II) can be given as the copper catalyst. As a substance that can be used as the base, an inorganic base such as potassium carbonate can be given. The above reaction is preferably performed in a solution, and 1,3-dimethyl-3,4,5,6-tetrahydro-2(1H)-pyrimidinone (abbreviation: DMPU), toluene, xylene, benzene, and the like can be given as a solvent that can be used in the above reaction. However, the catalyst, base, and solvent which can be used are not limited thereto.

DMPU or xylene which has a high boiling point is preferably used as the base because, by an Ullmann reaction, an object can be obtained in a shorter time and at a higher yield when the reaction temperature is greater than or equal to 100° C. Since it is further preferable that the reaction temperature be a temperature greater than or equal to 150° C., DMPU is more preferably used.

The tertiary arylamine (the compound A2) having a halogen group, which is obtained as described above, is coupled with the arylboronic acid using a metal catalyst in the presence of a base, so that the compound M which is the triarylamine derivative described in Embodiment 1 can be synthesized. As for the arylboronic acid, an arylboronic acid having an aryl group represented by a is used.

As described above, as a reaction in which the tertiary arylamine (the compound A2) having a halogen group is coupled with the arylboronic acid, there are various reactions. As an example thereof, a Suzuki-Miyaura reaction can be given.

The case of performing a Suzuki-Miyaura reaction in the above reaction is described. As a palladium catalyst which can be used as a metal catalyst, palladium(II) acetate, tetrakis(triphenylphosphine)palladium(0), bis(triphenylphosphine)palladium(II)dichloride, and the like can be given. As a ligand in the above palladium catalyst, tri(ortho-tolyl)phosphine, triphenylphosphine, tricyclohexylphosphine, and the like can be given. In addition, as the above base, an organic base such as sodium tert-butoxide, an inorganic base such as potassium carbonate, and the like can be given. The reaction is preferably performed in a solution, and as the solvent which can be used, a mixed solvent of toluene and water; a mixed solvent of toluene, an alcohol such as ethanol, and water, a mixed solvent of xylene and water, a mixed solvent of xylene, an alcohol such as ethanol, and water; a mixed solvent of benzene and water, a mixed solvent of benzene, an alcohol such as ethanol, and water, a mixed solvent of ethers such as ethyleneglycoldimethylether and water; and the like can be given. However, the catalyst, ligand, base, and solvent which can be used are not limited thereto. In addition, in the above scheme, organoaluminum, organozirconium, organozinc, organotin compound, or the like may be used instead of an arylboronic acid.

<Synthetic Method 1-2>

In this synthetic method, a method in which the dihalogenated aryl (the compound E2) and an arylboronic acid are coupled first to synthesize monohalogenated aryl (a compound E1) and then the monohalogenated aryl (the compound E1) is coupled with the secondary arylamine (the compound D1) is shown. Note that in this reaction, as for the arylboronic acid, an arylboronic acid having an aryl group represented by a is used.

In order to couple the dihalogenated aryl (the compound E2) and the arylboronic acid, a reaction may be performed using a metal catalyst in the presence of a base. As a reaction example, a Suzuki-Miyaura reaction can be given. In the case of performing the reaction by using a Suzuki-Miyaura reaction, the synthesis is performed in a manner similar to that of the synthesis described in Synthetic Method 1-1. Since the description on the synthetic method will be repeated, the detailed description is omitted and the description on a Suzuki-Miyaura reaction in Synthetic Method 1-1 is to be referred. Through this reaction, the compound E1 which is a monohalogenated aryl having a substituent α can be synthesized.

After that, the synthesized monohalogenated aryl (the compound E1) and the secondary arylamine (the compound D1) are coupled using a metal catalyst in the presence of a base, so that the compound M which is the triarylamine derivative described in Embodiment 1 can be synthesized. As a coupling reaction used for the reaction, there are various reactions. As a typical example thereof, a Buchwald-Hartwig reaction, an Ullmann reaction, and the like can be given. The detailed description on the reaction using a Buchwald-Hartwig reaction or an Ullmann reaction is made in Synthetic Method 1-1, and this reaction can also be performed in a similar manner. Therefore, since the description on the synthetic method will be repeated, the description is omitted and the descriptions on a Buchwald-Hartwig reaction and Ullmann reaction in Synthetic Method 1-1 are to be referred.

<Synthetic Method 2>

In this synthetic method, the following compound M which is the triarylamine derivative described in Embodiment 1 is synthesized by Reaction Scheme (A-2). Reaction Scheme (A-2) shows a synthetic method of the above compound M in which, with secondary arylamine (a compound B3) used as a starting material, a substance (a compound B1) that is coupled with an arylboronic acid is coupled with halogenated aryl after the end group of an aryl group of the compound B3 is halogenated.

(A-2)

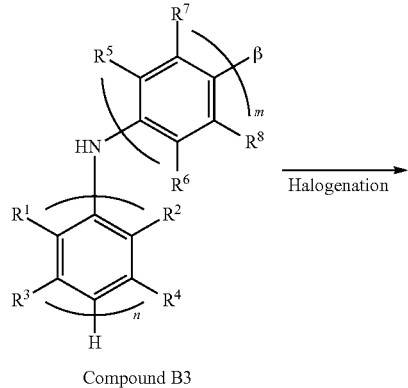

Compound B3

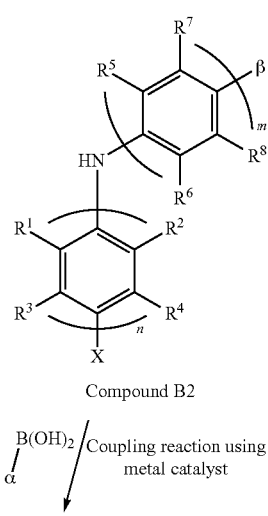

Compound B2

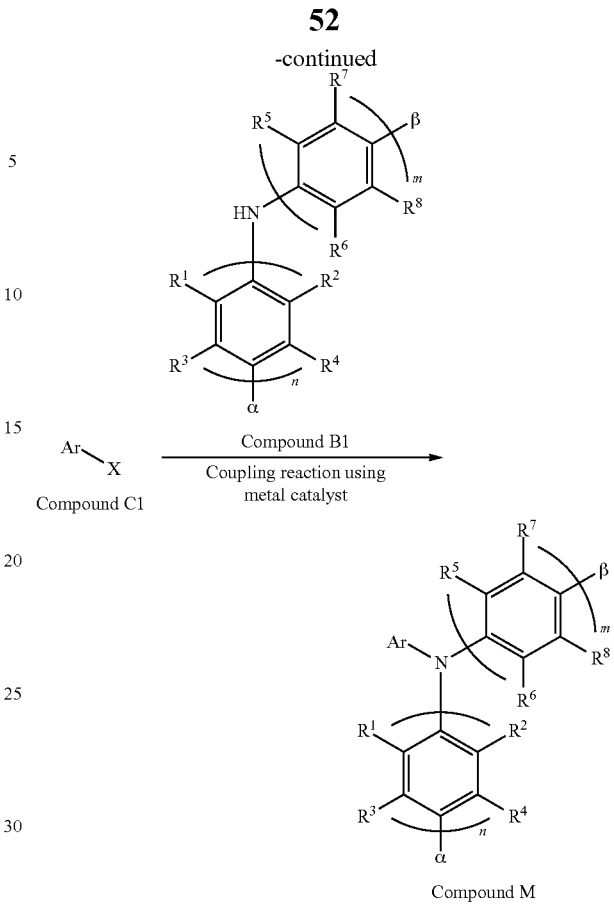

Compound M

In this Reaction Scheme, (A-2), hydrogen at the end group of an aryl group of the compound B3 which is secondary arylamine having a substituent β is first halogenated using a halogenating agent to obtain halide (a compound B2) of secondary arylamine having a substituent β. As the halogenating agent, N-Bromosuccinimide (abbreviation: NBS), N-Iodosuccinimide (abbreviation: NIS), bromine, iodine, potassium iodide, or the like can be used. As the halogenating agent, the use of a bromide such as N-Bromosuccinimide (abbreviation: NBS) or bromine is preferable because synthesis can be performed at low cost.

Subsequently, the compound B2 and the arylboronic acid are coupled to synthesize secondary arylamine represented by the compound B1. In order to couple the secondary arylamine (the compound B2) having a halogen group and the arylboronic acid, a reaction may be performed using a metal catalyst in the presence of a base. As a reaction example, a Suzuki-Miyaura reaction can be given. In the case of performing the reaction by using a Suzuki-Miyaura reaction, the synthesis is performed in a manner similar to that of the synthesis described in Synthetic Method 1-1. Since the description on the synthetic method will be repeated, the detailed description is omitted and the description on a Suzuki-Miyaura reaction in Synthetic Method 1-1 is to be referred. Through this reaction, the compound B1 which is the secondary arylamine having a substituent α and a substituent β can be synthesized. Note that as the halogenating agent for the halogenation, it is preferable to use an iodide such as N-Iodosuccinimide (abbreviation: NIS), iodine, or potassium iodide and select iodine as a halogen for substitution because this coupling reaction occurs efficiently in a shorter time.

Next, the Compound B1 which is the secondary arylamine and halogenated aryl represented by a compound C1 are coupled, so that the compound M which is the triarylamine derivative described in Embodiment 1 can be synthesized. As a coupling reaction used for the reaction, there are various reactions. As a typical example thereof, a Buchwald-Hartwig reaction, an Ullmann reaction, and the like can be given. The detailed description on the reaction using a Buchwald-Hartwig reaction or an Ullmann reaction is made in Synthetic Method 1-1, and this reaction can also be performed in a similar manner. Therefore, since the description on the synthetic method will be repeated, the description is omitted and the descriptions on a Buchwald-Hartwig reaction and Ullmann reaction in Synthetic Method 1-1 are to be referred.

Note that as described above, the compound B1 can be obtained by halogenating the secondary arylamine (the compound B3) and being coupled with the arylboronic acid. Alternatively, as in Reaction Scheme (A-3), there is a method in which synthesis is performed by coupling primary arylamine (a compound S1) and the monohalogenated aryl (the compound E1). As a coupling reaction used for the reaction, there are various reactions. As a typical example thereof, a Buchwald-Hartwig reaction, an Ullmann reaction, and the like can be given. The detailed description on the reaction using a Buchwald-Hartwig reaction or an Ullmann reaction is made in Synthetic Method 1-1, and this reaction can also be performed in a similar manner. Therefore, since the description on the synthetic method will be repeated, the description is omitted and the descriptions on a Buchwald-Hartwig reaction and Ullmann reaction in Synthetic Method 1-1 are to be referred.

pound B1), the primary arylamine (the compound S1) and the halogenated aryl can be reacted with a high yield in an equivalent of 1:1, which is preferable.

<Synthetic Method 3>

In this synthetic method, the following compound M which is the triarylamine derivative described in Embodiment 1 is synthesized by Reaction Scheme (A-4). Reaction Scheme (A-4) shows a synthetic method of the compound M in which, with tertiary arylamine (a compound A3) used as a starting material, boron oxidation is performed and a substance (a compound A1) on which the boron oxidation is performed is coupled with halogenated aryl after the end group of an aryl group of the compound A3 is halogenated.

(A-4)

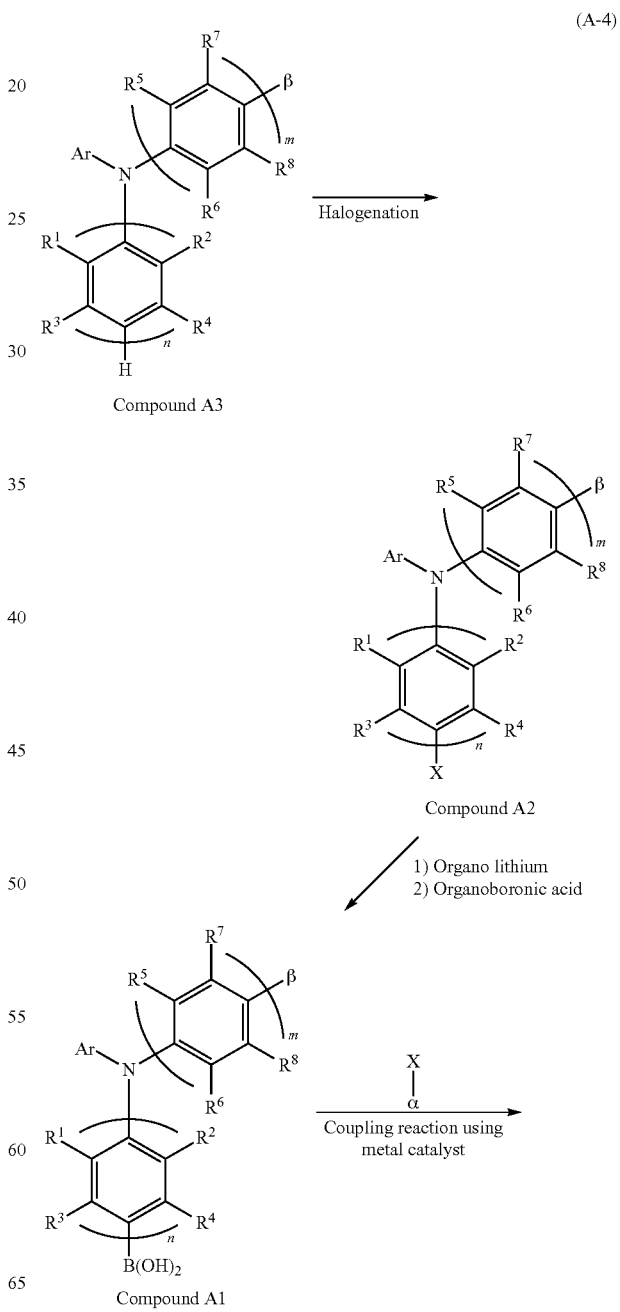

(A-3)

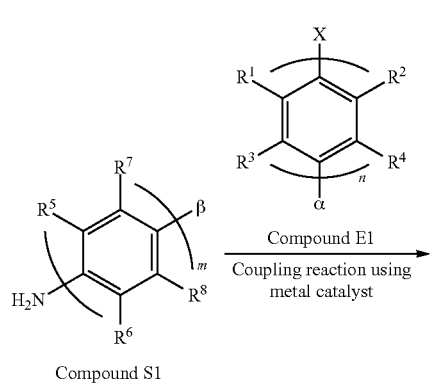

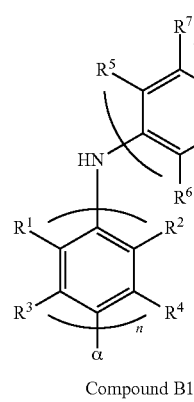

Note that when a Buchwald-Hartwig reaction is used for the synthesis of the above secondary arylamine (the com-

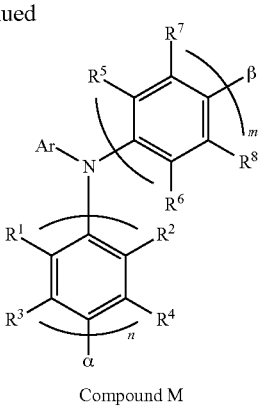

Compound M

The tertiary arylamine (the compound A3) is a compound in which a portion represented by α in the compound M, which is the triarylamine derivative described in Embodiment 1, is hydrogen. Therefore, by halogenating the hydrogen portion, the halogenated aryl (the compound A2) in which the portion represented by α in the compound M is halogen can be synthesized. The halogenation can be performed using a halogenating agent. As the halogenating agent, N-Bromosuccinimide (abbreviation: NBS), N-Iodosuccinimide (abbreviation: NIS), bromine, iodine, potassium iodide, or the like can be used. As the halogenating agent, the use of a bromide such as N-Bromosuccinimide (abbreviation: NBS) or bromine is preferable because synthesis can be performed at low cost.

Subsequently, boron oxidation of the obtained halogenated aryl (the compound A2) is performed to synthesize arylboronic acid (the compound A1). Synthesis of the arylboronic acid (the compound A1) can be performed by a method using organolithium and organoboronic acid. In addition, n-butyllithium, methyllithium, or the like can be used as the organolithium. Trimethyl borate, isopropyl borate, or the like can be used as the organoboronic acid.

After that, the synthesized arylboronic acid (the compound A1) is coupled with the halogenated aryl in which an aryl group represented by α and a halogen are bonded, so that the compound M which is the triarylamine derivative described in Embodiment 1 can be synthesized. In order to couple the arylboronic acid (the compound A1) with the halogenated aryl in which an aryl group represented by α and a halogen are bonded, a reaction may be performed using a metal catalyst in the presence of a base. As a reaction example, a Suzuki-Miyaura reaction can be given. In the case of performing the reaction by using a Suzuki-Miyaura reaction, the synthesis is performed in a manner similar to that of the synthesis described in Synthetic Method 1-1. Since the description on the synthetic method will be repeated, the detailed description is omitted and the description on a Suzuki-Miyaura reaction in Synthetic Method 1-1 is to be referred. Note that as the halogenating agent for the halogenation, it is preferable to use an iodide such as N-Iodosuccinimide (abbreviation: NIS), iodine, or potassium iodide and select iodine as a halogen for substitution because this coupling reaction occurs efficiently in a shorter time.

In the following Reaction Scheme (A-5), a synthetic method of the compound A3 which is used as a starting material of Reaction Scheme (A-4) will be shown. In this Reaction Scheme (A-5), although the following methods are shown, the synthetic method of the compound A3 is not limited thereto: a method of coupling the secondary arylamine (the compound B3) and the halogenated aryl (the compound C1); a method of coupling the secondary arylamine (the compound D1) and halogenated aryl (a compound E3); and a method of coupling two kinds of halogenated aryl (the compound C1 and a compound F1) and primary arylamine (a compound G1).

(A-5)

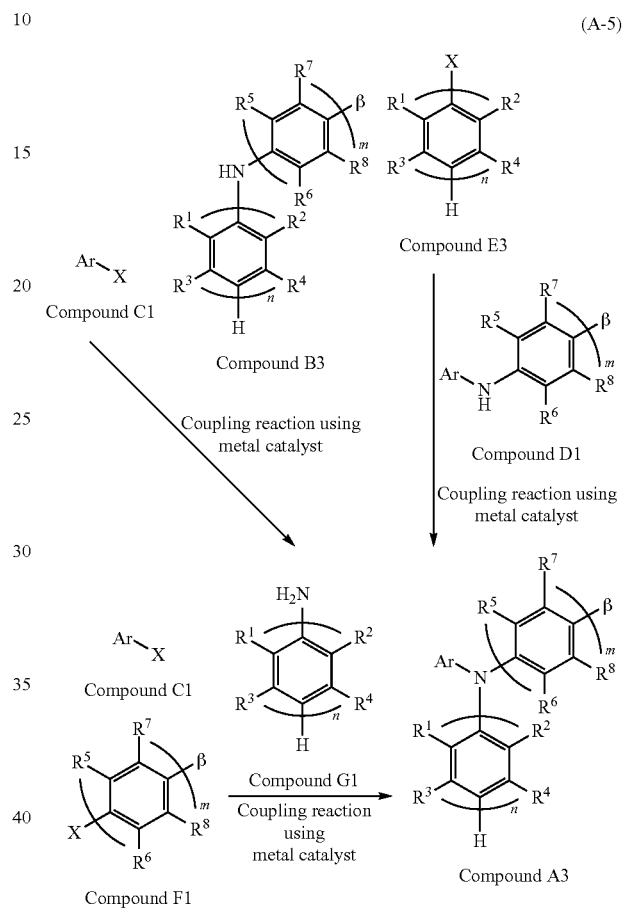

For the above coupling reaction, a coupling reaction using a metal catalyst can be used. As such a reaction, there are various reactions. As a typical example thereof, a Buchwald-Hartwig reaction, an Ullmann reaction, and the like can be given. The detailed description on the reaction using a Buchwald-Hartwig reaction or an Ullmann reaction is made in Synthetic Method 1-1, and this reaction can also be performed in a similar manner. Therefore, since the description on the synthetic method will be repeated, the description is omitted and the descriptions on a Buchwald-Hartwig reaction and Ullmann reaction in Synthetic Method 1-1 are to be referred. Note that in the method of coupling the two kinds of halogenated aryl (the compound C1 and the compound F1) and the primary arylamine (the compound G1), when the compound C1 and the compound F1 are the same (X may be different), the compound A3 can be obtained with a higher yield, which is preferable. In addition, in this reaction, when the Ullmann reaction described above is used, 2 equivalent halogenated aryl can be reacted more efficiently with respect to the primary arylamine, which is preferable.

\<Synthetic Method 4\>

In this synthetic method, the following Compound M which is the triarylamine derivative described in Embodiment 1 is synthesized by two schemes, Reaction Scheme (A-6) and Reaction Scheme (A-7). Reaction Scheme (A-6) shows a synthetic method of the above compound M in which the halogenated aryl (the compound C1) and secondary arylamine (a compound P3) are coupled to synthesize tertiary arylamine (a compound P2); among three aryl groups of the tertiary arylamine (the compound P2), the end groups of two aryl groups are halogenated to synthesize dihalide (a compound P1) of the tertiary arylamine; and after that arylboronic acids and the compound P1 are coupled.

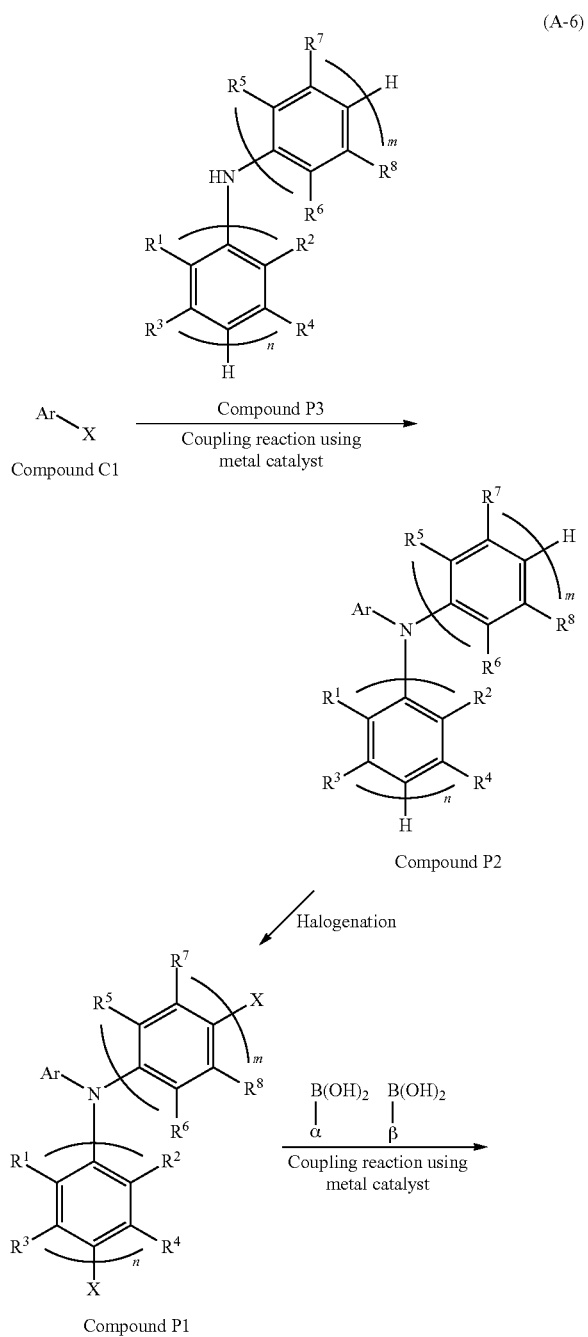

(A-6)

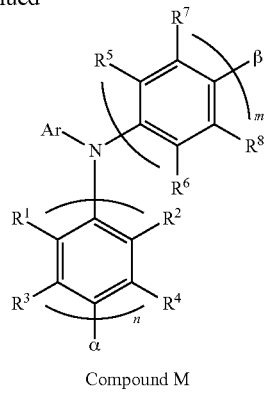

Compound M

First, the tertiary arylamine (the compound P2) is synthesized by coupling the halogenated aryl (the compound C1) and the secondary arylamine (the compound P3). Note that here, the compound P2 is compound in which both α and β in the compound KI which is the triarylamine derivative described in Embodiment 1, are hydrogen. For the coupling reaction, a coupling reaction using a metal catalyst can be used. As such a reaction, there are various reactions. As a typical example thereof, a Buchwald-Hartwig reaction, an Ullmann reaction, and the like can be given. The detailed description on the reaction using a Buchwald-Hartwig reaction or an Ullmann reaction is made in Synthetic Method 1-1, and this reaction can also be performed in a similar manner. Therefore, since the description on the synthetic method will be repeated, the description is omitted and the descriptions on a Buchwald-Hartwig reaction and Ullmann reaction in Synthetic Method 1-1 are to be referred.

Subsequently, the dihalogenated aryl (the compound P1) is synthesized by halogenating hydrogen of the compound P2, which corresponds to positions of α and β in the compound M which is the triarylamine derivative described in Embodiment 1. The halogenated reaction can be performed using a halogenating agent. As the halogenating agent, N-Bromosuccinimide (abbreviation: NBS), N-Iodosuccinimide (abbreviation: NIS), bromine, iodine, potassium iodide, or the like can be used. As the halogenating agent, the use of a bromide such as N-Bromosuccinimide (abbreviation: NBS) or bromine is preferable because synthesis can be performed at low cost. Note that the halogenating agent is preferably 2 equivalents or more, more preferably 2 equivalents in normality with respect to the compound P2.

After that, the dihalogenated aryl (the compound P1) are coupled with an arylboronic acid having an aryl group represented by a and an arylboronic acid having an aryl group represented by β, so that the compound M which is the triarylamine derivative described in Embodiment 1 can be synthesized. In order to couple the arylboronic acids and the dihalogenated aryl (the compound P1), a reaction may be performed using a metal catalyst in the presence of a base. As a reaction example, a Suzuki-Miyaura reaction can be given. In the case of performing the reaction by using a Suki-Miyaura reaction, the synthesis is performed in a manner similar to that of the synthesis described in Synthetic Method 1-1. Since the description on the synthetic method will be repeated, the detailed description is omitted and the description on a Suzuki-Miyaura reaction in Synthetic Method 1-1 is to be referred. Note that as the halogenating agent for the halogenation, it is preferable to use an iodide such as N-Iodosuccinimide (abbreviation: NIS), iodine, or potassium iodide and select iodine as a halogen for substitution because this coupling reaction occurs efficiently in a shorter time. In addition, when the arylboronic acid having a group represented by α as an aryl group and the arylboronic acid having a group represented by β as an aryl group are the same in this reaction, the compound M can be obtained with a high yield, which is preferable.

In Reaction Scheme (A-6), the halogenation of the tertiary arylamine (the compound P2) and the coupling with the arylboronic acid are performed at the same time on two aryl groups; however, in Reaction Scheme (A-7), a method is shown in which halogenation of the tertiary arylamine (the compound P2) and coupling with an arylboronic acid are performed on two aryl groups one by one.

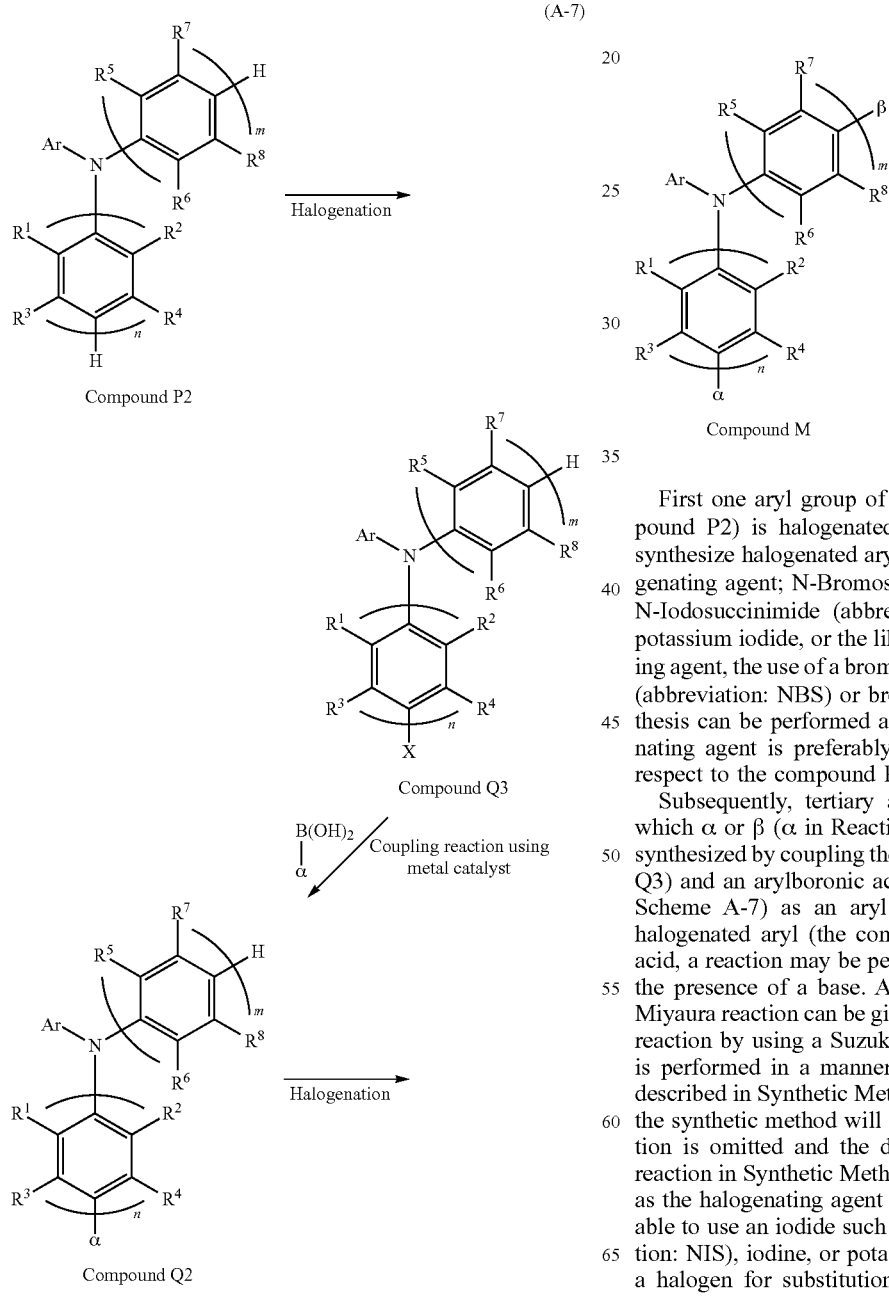

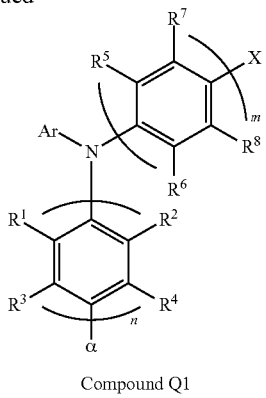

First one aryl group of the tertiary arylamine (the compound P2) is halogenated using a halogenating agent to synthesize halogenated aryl (a compound Q3). As the halogenating agent; N-Bromosuccinimide (abbreviation: NBS), N-Iodosuccinimide (abbreviation: NIS), bromine, iodine, potassium iodide, or the like can be used. As the halogenating agent, the use of a bromide such as N-Bromosuccinimide (abbreviation: NBS) or bromine is preferable because synthesis can be performed at low cost. Note that the halogenating agent is preferably 1 equivalent in normality with respect to the compound P2 because a yield improves.

Subsequently, tertiary arylamine (a compound Q2) to which α or β (α in Reaction Scheme A-7) is introduced is synthesized by coupling the halogenated aryl (the compound Q3) and an arylboronic acid having α or β (α in Reaction Scheme A-7) as an aryl group. In order to couple the halogenated aryl (the compound Q3) and the arylboronic acid, a reaction may be performed using a metal catalyst in the presence of a base. As a reaction example, a Suzuki-Miyaura reaction can be given. In the case of performing the reaction by using a Suzuki-Miyaura reaction, the synthesis is performed in a manner similar to that of the synthesis described in Synthetic Method 1-1. Since the description on the synthetic method will be repeated, the detailed description is omitted and the description on a Suzuki-Miyaura reaction in Synthetic Method 1-1 is to be referred. Note that as the halogenating agent for the halogenation, it is preferable to use an iodide such as N-Iodosuccinimide (abbreviation: NIS), iodine, or potassium iodide and select iodine as a halogen for substitution because this coupling reaction occurs efficiently in a shorter time.

After that, the compound Q2 which is the obtained tertiary arylamine is halogenated to synthesize halogenated aryl (a compound Q1). The halogenation may be performed using a halogenation agent, and as the halogenating agent, N-Bromosuccinimide (abbreviation: NBS), N-Iodosuccinimide (abbreviation: NIS), bromine, iodine, potassium iodide, or the like can be used. As the halogenating agent, the use of a bromide such as N-Bromosuccinimide (abbreviation: NBS) or bromine is preferable because synthesis can be performed at low cost. Note that the halogenating agent is preferably 1 equivalent in normality with respect to the compound Q2 because a yield improves.

Lastly, the halogenated aryl (the compound Q1) and an arylboronic acid having an aryl group represented by α or β (β in Reaction Scheme A-7) are coupled, so that the compound M, which is the triarylamine derivative described in Embodiment 1, to which α or β is introduced can be synthesized. In order to couple the halogenated aryl (the compound Q1) and the arylboronic acid, a reaction may be performed using a metal catalyst in the presence of a base. As a reaction example, a Suzuki-Miyaura reaction can be given. In the case of performing the reaction by using a Suzuki-Miyaura reaction, the synthesis is performed in a manner similar to that of the synthesis described in Synthetic Method 1-1. Since the description on the synthetic method will be repeated, the detailed description is omitted and the description on a Suzuki-Miyaura reaction in Synthetic Method 1-1 is to be referred. Note that as the halogenating agent for the halogenation, it is preferable to use an iodide such as N-Iodosuccinimide (abbreviation: NIS), iodine, or potassium iodide and select iodine as a halogen for substitution because this coupling reaction occurs efficiently in a shorter time.

<Synthetic Method 5>

In this synthetic method, the following compound M which is the triarylamine derivative described in Embodiment 1 is synthesized by Reaction Scheme (A-8). Reaction Scheme (A-8) shows a synthetic method of the above compound M in which primary arylamine (a compound R1) is coupled at the same time with the halogenated aryl (the compound E1) in which α is bonded to its end group and the halogenated aryl (the compound F1) in which β is bonded to its end group.

(A-8)

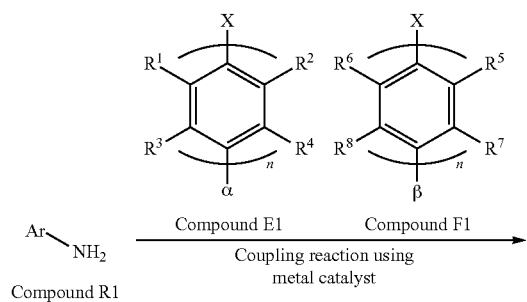

Compound R1    Compound E1    Compound F1
Coupling reaction using metal catalyst -continued

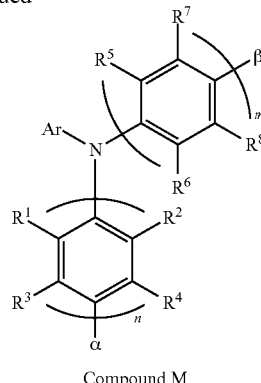

Compound M

By this reaction, the compound M which is the triarylamine derivative described in Embodiment 1 is synthesized in such a manner that the compound R1 which is primary arylamine having an aryl group represented by Ar is coupled at the same time with the compound E1 which is the halogenated aryl having an aryl group represented by at and the compound F1 which is the halogenated aryl having a substituent represented by β, with the use of a metal catalyst. As such a reaction, there are various reactions. As a typical example thereof, a Buchwald-Hartwig reaction, an Ullmann reaction, and the like can be given. The detailed description on the reaction using a Buchwald-Hartwig reaction or an Ullmann reaction is made in Synthetic Method 1-1, and this reaction can also be performed in a similar manner. Therefore, since the description on the synthetic method will be repeated, the description is omitted and the descriptions on a Buchwald-Hartwig reaction and Ullmann reaction in Synthetic Method 1-1 are to be referred. Note that in the method of coupling two kinds of the halogenated aryl (the compound E1 and the compound F1) and the primary arylamine (the compound R1), when the compound E1 and the compound F1 are the same (X may be different), the compound M can be obtained with a higher yield, which is preferable. In addition, in this reaction, when the Ullmann reaction described above is used, 2 equivalent halogenated aryl can be reacted more efficiently with respect to the primary arylamine, which is preferable.

Note that in each of Reaction Schemes (A-1) to (A-8), X represents a halogen group, which is a chloro group, a bromo group, or an iodine group, preferably a bromo group or an iodine group. In addition, Ar is a phenyl group or a biphenyl group, α is a naphthyl group, and β is hydrogen or a naphthyl group. In addition, $R^1$ to $R^8$ each independently represent any of hydrogen, an alkyl group having 1 to 6 carbon atoms, or a phenyl group; and n and m each independently represent 1 or 2. Although a number of reaction schemes are given as examples in the above description, of course, the compound M which is the triarylamine derivative described in Embodiment 1 may be synthesized by any other synthetic methods.

Embodiment 3

One embodiment of a light-emitting element using the triarylamine derivative described in Embodiment 1 will be shown below with reference to FIG. 1A.

A light-emitting element of this embodiment has a plurality of layers between a pair of electrodes. In this embodiment, a light-emitting element includes a first electrode 102, a second electrode 104, and an EL layer 103 provided between the first electrode 102 and the second electrode 104. In addition, in this embodiment, the first electrode 102 functions as an anode and the second electrode 104 serves as a cathode. In other words, when voltage is applied to the first electrode 102 and the second electrode 104 such that the potential of the first electrode 102 is higher than that of the second electrode 104, light emission can be obtained.

A substrate 101 is used as a support of the light-emitting element. The substrate 101 can be formed with, for example, glass, plastic, or the like. Note that materials other than glass or plastic can be used as long as they can function as a support of the light-emitting element.

As the first electrode 102, a metal, an alloy, a conductive compound, a mixture thereof or the like having a high work function (specifically 4.0 eV or more) is preferably used. Specifically, for example, indium tin oxide (ITO), indium tin oxide containing silicon or silicon oxide, indium zinc oxide (IZO), indium oxide containing tungsten oxide and zinc oxide (IWZO), and the like can be given. These conductive metal oxide films are generally formed by sputtering; however, the films may be manufactured by applying a sol-gel method. For example, indium zinc oxide (IZO) can be formed by a sputtering method using indium oxide into which zinc oxide of 1 wt % to 20 wt % is added, as a target. Indium oxide containing tungsten oxide and zinc oxide (IWZO) can be formed by a sputtering method using a target in which 0.5 wt % to 5 wt % of tungsten oxide and 0.1 wt % to 1 wt % of zinc oxide are mixed with indium oxide. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like can be given.

There is no particular limitation on a stack structure of the EL layer 103. The EL layer 103 may be formed as appropriate using a layer including the triarylamine derivative according to one embodiment of the present invention, which is described in Embodiment 1, in combination with any of a layer including a substance with a high electron transporting property, a substance with a high hole transporting property, a layer including a substance with a high electron injecting property, a layer including a substance with a high hole injecting property, a layer including a substance with a bipolar property (a material with high electron and hole transporting properties), or the like. For example, the EL layer 103 can be formed by an appropriate combination of a hole injecting layer, a hole transporting layer, a light-emitting layer, an electron transporting layer, an electron injecting layer, or the like. This embodiment will show the EL layer 103 having a structure in which a hole injecting layer 111, a hole transporting layer 112, a light-emitting layer 113, and an electron transporting layer 114 are sequentially stacked over the first electrode 102. Specific materials to form each of the layers is given below.

The hole injecting layer 111 is a layer containing a substance having a high hole injecting property. As the substance with a high hole injecting property, the following can be used: molybdenum oxide, vanadium oxide, ruthenium oxide, tungsten oxide, manganese oxide, or the like. Alternatively, the hole injecting layer 111 can be formed using any of the following materials: phthalocyanine compounds such as phthalocyanine ($H_2PC$) and copper phthalocyanine (CuPc); aromatic amine compounds such as 4,4'-bis[N-(4-diphenylaminophenyl)-N-phenylamino]biphenyl (abbreviation: DPAB) and 4,4'-bis(N-{4-[N-(3-methylphenyl)-N-phenylamino]phenyl}-N-phenylamino)biphenyl (abbreviation: DNTPD); macromolecules such as poly(3,4-ethylene dioxythiophene)/poly(styrenesulfonic acid) (abbreviation: PEDOT/PSS); and the like. Note that the triarylamine derivative described in Embodiment 1 can also be used as the hole injecting material.

Alternatively, the hole injecting layer 111 can be formed using a composite material in which an acceptor substance is contained in a substance having a high hole transporting property. Note that by using the substance having a high hole transporting property containing an acceptor substance, a material used to form an electrode may be selected regardless of its work function. In other words, besides a material with a high work function, a material with a low work function may also be used as the first electrode 102. As the acceptor substance, 7,7,8,8-tetracyano-2,3,5,6-tetrafluoro-quinodimethane (abbreviation: $F_4$-TCNQ), chloranil, and the like can be given. Further, transition metal oxides can be given. Further, oxides of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are each preferable because of a high electron accepting property. Among these, molybdenum oxide is especially preferable because it is stable in the air and its hygroscopic property is low so that it can be easily treated.

As the substance having a high hole transporting property used for the composite material, any of various compounds such as an aromatic amine compound, a carbazole derivative, aromatic hydrocarbon, and a macromolecular compound (such as an oligomer, a dendrimer, and a polymer) can be used. The organic compound used for the composite material is preferably an organic compound having a high hole transporting property. Specifically, a substance having a hole mobility of $10^{-6}$ cm$^2$/Vs or more is preferably used. Note that any substance other than the above substances may also be used as long as it is a substance in which the hole transporting property is higher than the electron transporting property. An organic compound which can be used as a substance having a high hole transporting property for the composite material is specifically given below.

As aromatic amine compounds, for example, the following can be given: N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); and the like.

As carbazole derivatives which can be used for the composite material, the following can be given: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); and the like.

As other examples of carbazole derivatives which can be used for the composite material, the following can be given: 4,4'-di(N-carbazolyl)biphenyl (abbreviation: CBP), 1,3,5-tris[4-(N-carbazolyl)phenyl]benzene (abbreviation: TCPB), 9-[4-(10-phenyl-9-anthryl)phenyl]-9H-carbazole (abbreviation: CzPA), 1,4-bis[4-(N-carbazolyl)phenyl]-2,3,5,6-tetraphenylbenzene, and the like.

Further, as aromatic hydrocarbons which can be used for the composite material, for example, the following can be given: 2-tert-butyl-9,10-di(2-naphthyl)anthracene (abbreviation: t-BuDNA); 2-tert-butyl-9,10-di(1-naphthyl)anthracene, 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl 10,10'-bis[(2,3,4,5,6-pentaphenyl)phenyl]-9,9'-bianthryl; anthracene; tetracene; rubrene; perylene; 2,5,8,11-tetra(tert-butyl)perylene; and the like. Alternatively, pentacene, coronene, or the like can also be used. Note that it is preferable that the aromatic hydrocarbon have a hole mobility of $1 \times 10^{-6}$ cm$^2$/Vs or more, and in addition thereto, it is preferable that the number of carbon atoms that forms a condensed ring be 14 to 42 in terms of evaporativity at the time of evaporation or film quality after film formation, when the above aromatic hydrocarbon is formed by an evaporation method.

Note that an aromatic hydrocarbon which can be used for the composite material may have a vinyl skeleton. As an aromatic hydrocarbon having a vinyl group, for example, there are 4,4'-bis(2,2-diphenylvinyl)biphenyl (abbreviation: DPVBi), 9,10-bis[4-(2,2-diphenylvinyl)phenyl]anthracene (abbreviation: DPVPA), and the like.

Alternatively, a macromolecular compound such as poly(N-vinylcarbazole) (abbreviation: PVK), poly(4-vinyltriphenylmine) (abbreviation: PVTPA), poly[N-(4-{N-[4-(4-diphenylamino)phenyl]phenyl-N-phenylamino}phenyl) methacrylamide] (abbreviation: PTPDMA), or poly[N,N'-bis(4-butylphenyl)-N,N'-bis(phenyl)benzidine (abbreviation: Poly-TPD) can be used.

Note that the triarylamine derivative described in Embodiment 1 can also be used as the organic compound in the composite material.

The hole transporting layer 112 is a layer containing a substance having a high hole transporting property. In this embodiment, the triarylamine derivative described in Embodiment 1 is used as the hole transporting layer.

In addition, the triarylamine derivative according to one embodiment of the present invention, which is described in Embodiment 1, can also be used for both the hole injecting layer 111 and the hole transporting layer 112. In this case, an element can be manufactured easily and the use efficiency of the material can be improved. Moreover, since energy diagrams of the hole injecting layer 111 and the hole transporting layer 112 are the same or similar, carriers can be transported easily between the hole injecting layer 111 and the hole transporting layer 112.

The light-emitting layer 113 is a layer containing a light-emitting substance. The light-emitting layer 113 may be formed using a film including only a light-emitting substance or a film in which a light-emitting substance is dispersed in a host material.

Materials that can be used as the above light-emitting substance in the light-emitting layer 113 are not particularly limited, and light emitted by these materials may be fluorescence or phosphoresce. For example, the following materials can be given as the above light-emitting substance.

As a fluorescent light-emitting material, the following materials having an emission wavelength of 450 nm or more can be given in addition to N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), and the like: 4-(9H-carbazol-9-yl)-4'-(9,10-diphenyl-2-anthryl)triphenylamine (abbreviation: 2YGAPPA); N,9-diphenyl-N-[4-(10-phenyl-9-anthryl)phenyl]-9H-carbazol-3-amine (abbreviation: PCAPA); perylene; 2,5,8,11-tetra-tert-butylperylene (abbreviation: TBP); 4-(10-phenyl-9-anthryl)-4'-(9-phenyl-9H-carbazol-3-yl)triphenylamine (abbreviation: PCBAPA); N,N'-(2-tert-butylanthracene-9,10-diyldi-4,1-phenylene)bis[N,N,N-triphenyl-1,4-phenylenediamine] (abbreviation: DPABPA); N,9-diphenyl-N-[4-(9,10-diphenyl-2-anthryl)phenyl]-9H-carbazol-3-amine (abbreviation: 2PCAPPA); N-[4-(9,10-diphenyl-2-anthryl)phenyl]-N,N',N'-triphenyl-1,4-phenylenediamine (abbreviation: 2DPAPPA); N,N,N',N',N'',N'',N'''-octaphenyldibenzo[g,p]chrysene-2,7,10,15-tetramine (abbreviation: DBC1); coumarin 30; N-(9,10-diphenyl-2-anthryl)-N,9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N',N'-triphenyl-1,4-phenylenediamine (abbreviation: 2DPAPA); N-[9,10-bis(1,1'-biphenyl-2-yl)-2-anthryl]-N,N',N'-triphenyl-1,4-phenylenediamine (abbreviation: 2DPABPhA); 9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); coumarin 545T; N,N'-diphenylquinacridone (abbreviation: DPQd); rubrene; 5,12-bis(1,1'-biphenyl-4-yl)-6,11-diphenyltetracene (abbreviation: BPT); 2-(2-{2-[4-(dimethylamino)phenyl]ethenyl}-6-methyl-4H-pyran-4-ylidene)propanedinitrile (abbreviation: DCM1); 2-{2-methyl-6-[2-(2,3,6,7-tetrahydro-1H,5H-benzo[ij]quinolizin-9-yl)etheyl]-4H-pyran-4-ylidene}propanedinitrile (abbreviation: DCM2); N,N,N',N'-tetrakis(4-methylphenyl)tetracene-5,11-diamine (abbreviation: p-mPhTD); 7,13-diphenyl-N,N,N',N'-tetrakis(4-methylphenyl)acenaphtho[1,2-a]fluoranthene-3,10-d iamine (abbreviation: p-mPhAFD); 2-{2-isopropyl-6-[2-(1,1,7,7-tetramethyl-2,3,6,7-tetrahydro-1H,5H-benzo[g]quinolizin-9-ylethenyl]-4H-pyran-4-ylidene)propanedinitrile (abbreviation: DCJTI); 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB); 2-(2,6-bis{2-[4-(dimethylamino)phenyl]ethenyl}-4H-pyran-4-ylidene)propanedinitrile (abbreviation: BisDCM); 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene)propanedinitrile (abbreviation: BisDCJTM); and the like.

As a phosphorescent light-emitting material, in addition to bis[2-(4',6'-difluorophenyl)pyridinato-N,C$^2$']iridium(I) tetrakis(1-pyrazolyl)borate (abbreviation: FIr6), materials having an emission wavelength in the range of 470 nm to 500 nm, such as bis[2-(4',6'-difluorophenyl)pyridinato-N,C$^2$']iridium(II)picolinate (abbreviation: FIrpic); bis[2-(3',5'-bistrifluoromethylphenyl)pyridinat-N,C$^2$']iridium(III) picolinate (abbreviation: Ir(CF$_3$ppy)$_2$(pic)); and bis[2-(4',6'-difluorophenyl)pyridinato-N,C$^2$']iridium(II)acetylacetonate (abbreviation: FIracac) can be given, and materials having an emission (green light emission) wavelength of 500 nm or more can be given, such as tris(2-phenylpyridinato)iridium(III) (abbreviation: Ir(ppy)$_3$); bis(2-phenylpyridinato)iridium(III) acetylacetonate (abbreviation: Ir(ppy)$_2$(acac)); tris(acetylacetonatoxmonophenanthroline)terbium (III) (abbreviation: Tb(acac)$_3$(Phen)); bis(benzo[h]quinolinato)iridium(OI)acetylacetonate (abbreviation: Ir(bzq)$_2$(acac)); bis(2,4-diphenyl-1,3-oxazolato-N,C$^{c'}$)iridium(acetyactonate (abbreviation: Ir(dpo)$_2$(acac)); bis[2-(4'-perfluorophenylphenyl)pyridinato]iridium(III)acetylacetonate (abbreviation: Ir(p-PF-ph)$_2$(acac)); bis(2-phenylbenzothiazolato-N,C$^{2'}$)iridium(III)acetylacetonate (abbreviation: Ir(btp)$_2$(acac)); bis[2-(2'-benzo[4,5-a]thienyl)pyridinato-N,C$^{3'}$]iridium(II)acetylacetonate (abbreviation: Ir(btp)$_2$(acac)); bis(1-phenylisoquinolinato-N,C$^{2'}$)iridium(MI)acetylacetonate (abbreviation: Ir(piq)$_2$(acac)); (acetylacetonato)bis[2,3-bis(4-fluorophenyl)quinoxalinato]iridium(III) (abbreviation: Ir(Fdpq)$_2$(acac)); (acetylacetonato)bis(2,3,5-triphenylpyrazinato)iridium(III) (abbreviation: Ir(tppr)$_2$(acac)); 2,3,7,8,12,13,17,18-octaethyl-21H,23H-porphyrinplatinum(II) (abbreviation: PtOEP); tris(1,3-diphenyl-1,3-propanedionatoXmonophenanthroline)europium(III) (abbreviation: Eu(DBM)$_3$(Phen)); and tris[1-(2-thenoyl)-3,3,3-trifluoroacetonato](monophenanthroline)europium (III) (abbreviation: Eu(TTA)$_3$(Phen)).

Having a large energy gap or triplet energy, the triarylamine derivative described in Embodiment 1 can be very preferably used as a material that forms the hole transporting layer in contact with the light-emitting layer. Among the materials described above, when the fluorescent light-emitting substance having an emission (blue light emission) wavelength of 450 nm or more or the phosphorescent light-emitting substance having an emission (green light emission) wavelength of 470 nm or more, preferably 500 nm or more is used, reduction in luminous efficiency or color purity unlikely occurs, which is a preferable structure.

In addition, materials that can be used as the above host material are not particularly limited and metal complexes, heterocyclic compounds, and aromatic amine compounds can be given, for example. As metal complexes, the following can be given: tris(8-quinolinolato)aluminum(III) (abbreviation: Alq); tris(4-methyl-8-quinolinolato)aluminum(MI) (abbreviation: Almqa$_3$); bis(10-hydroxybenzo[h]quinolinato)beryllium(II) (abbreviation: BeBq$_2$); bis(2-methyl-8-quinolinolato)$_4$-phenylphenolato)aluminum(I) (abbreviation: BAlq); bis(8-quinolinolato)zinc(I) (abbreviation: Znq); bis[2-(2-benzoxazolyl)phenolato]zinc(II) (abbreviation: ZnPBO); bis[2-(2-benzothiazolyl)phenolato]zinc(II) (abbreviation: ZnBTZ); and the like. As heterocyclic compounds, the following can be given: 2-(4-biphenylyl)-5-(4-tert-butylphenyl)-1,3,4-oxadiazole (abbreviation: PBD); 1,3-bis[5-(p-tert-butylphenyl)-1,3,4-oxadiazol-2-yl]benzene (abbreviation: OXD-7); 3-(4-biphenylyl)-4-phenyl-5-(4-tert-butylphenyl)-1,2,4-triazole (abbreviation: TAZ); 2,2',2''-(1,3,5-benzenetriyl)tris(1-phenyl-H-benzimidazole) (abbreviation: TPBI); bathophenanthroline (abbreviation: BPhen); bathocuproine (abbreviation: BCP); 9-[4-(5-phenyl-1,3,4-oxadiazol-2-yl)phenyl]-9H-carbazole (abbreviation: CO11); and the like. As aromatic amine compounds, the following can be given: 4,4'-bis[N-(1-naphthyl)-N-phenylamino]biphenyl (abbreviation: NPB or α-NPD); N,N'-bis(3-methylphenyl)-N,N-diphenyl-[1,1'-biphenyl]-4,4'-diamine. (abbreviation: TPD); 4,4'-bis[N-(spiro-9,9'-bifluoren-2-yl)-N-phenylamino]-1,1'-biphenyl (abbreviation: BSPB); and the like. Moreover, condensed polycyclic aromatic compounds such as an anthracene derivative, a phenanthrene derivative, a pyrene derivative, a chrysene derivative, and a dibenzo[g,p]chrysene derivative can be given. The following is specifically given as the condensed polycyclic aromatic compound: 9,10-diphenylanthracene (abbreviation: DPAnth); N,N-diphenyl-9-[4-(10-phenyl-9-anthryl)phenyl]-9H-carbazol-3-amine (abbreviation: CzA1PA); 4-(10-phenyl-9-anthryl)triphenylamine (abbreviation: DPhPA); 4-(9H-carbazol-9-yl)-4'-(10-phenyl-9-anthryl)triphenylamine (abbreviation: YGAPA); N,9-diphenyl-N-[4-(10-phenyl-9-anthryl)phenyl]-9H-carbazol-3-amine (abbreviation: PCAPA); N,9-diphenyl-N-{4-[4-(10-phenyl-9-anthryl)phenyl]phenyl}-9H-carbazol-3-amine (abbreviation: PCAPBA); N,9-diphenyl-N-(9,10-diphenyl-2-anthryl)-9H-carbazol-3-amine (abbreviation: 2PCAPA); 6,12-dimethoxy-5,11-diphenylchrysene; N,N,N',N',N'',N'',N''',N'''-octaphenyldibenzo[g,p]chrysene-2,7,10,15-tetramine (abbreviation: DBC1); 9-[4-(10-phenyl-9-anthryl)phenyl]-9H-carbazole (abbreviation: CzPA); 3,6-diphenyl-9-[4-(10-phenyl-9-antryl)phenyl]-9H-carbazole (abbreviation: DPCzPA); 9,10-bis(3,5-diphenylphenyl)anthracene (abbreviation: DPPA); 9,10-di(2-naphthyl)anthracene (abbreviation: DNA); 2-tert-butyl-9,10-di(2-naphthyl)anthracene (abbreviation: t-BuDNA); 9,9'-bianthryl (abbreviation: BANT); 9,9'-(stilbene-3,3'-diyl)diphenanthrene (abbreviation: DPNS); 9,9'-(stilbene-4,4'-diyl)diphenanthrene (abbreviation: DPNS2); 3,3',3''-(benzene-1,3,5-triyl)tripyrene (abbreviation: TPB3); and the like. From these materials and known materials, a substance having an energy gap larger than that of the light-emitting substance may be selected. Moreover, in the case where a light-emitting substance emits phosphorescence, a substance having a triplet energy (energy difference between a ground state and a triplet excitation state) which is higher than that of the light-emitting substance may be selected as a host material.

The light-emitting layer 113 may be a stack of two or more layers. For example, in the case where the light-emitting layer 113 is formed by stacking a first light-emitting layer and a second light-emitting layer in that order from the hole transporting layer side, for example, the first light-emitting layer can be formed using a substance having a hole transporting property as the host material and the second light-emitting layer can be formed using a substance having an electron transporting property as the host material.

When the light-emitting layer having the structure described above is formed using a plurality of materials, the light-emitting layer can be formed using co-evaporation by a vacuum evaporation method; or an ink-jet method, a spin coating method, a dip coating method, or the like as a method for mixing a solution.

The electron transporting layer 114 is a layer containing a substance having a high electron transporting property. For example, the electron transporting layer 114 is a layer including a metal complex having a quinoline skeleton or a benzoquinoline skeleton such as tris(8-quinolinolato)aluminum (abbreviation: Alq), tris(4-methyl-8-quinolinolato)aluminum (abbreviation: Almq$_3$), bis(10-hydroxybenzo[h]quinolinato)beryllium (abbreviation: BeBq$_2$), or bis(2-methyl-8-quinolinolato)(4-phenylphenolato)aluminum (abbreviation: BAlq). Alternatively, a metal complex having an oxazole-based or thiazole-based ligand, such as bis[2-(2-hydroxyphenyl)benzoxazolato]zinc (abbreviation: Zn(BOX)$_2$) or bis[2-(2-hydroxyphenyl)-benzothiazolato]zinc (abbreviation Zn(BTZ)$_2$) can be used. Besides the metal complexes, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), bathophenanthroline (abbreviation: BPhen), bathocuproine (abbreviation: BCP), or the like can also be used. The substances described here are mainly substances having an electron mobility of $10^{-6}$ cm$^2$Vs or more. Note that a substance other than the above substances may be used as long as it has a higher electron transporting property than a hole transporting property.

Further, the electron transporting layer is not limited to a single layer, and two or more layers made of the above substances may be stacked.

Further, a layer for controlling transport of electron carriers may be provided between the electron transporting layer and the light-emitting layer. Specifically, the layer for controlling transport of electron carriers is a layer formed by adding a small amount of substance having a high electron trapping property to the material having a high electron transporting property as described above, so that carrier balance can be adjusted. Such a structure is very effective in suppressing a problem (such as shortening of element lifetime) caused when electrons pass through the light-emitting layer.

In addition, an electron injecting layer may be provided between the electron transporting layer and the second electrode 104, in contact with the second electrode 104. As the electron injecting layer, an alkali metal, an alkaline earth metal, or a compound thereof such as lithium fluoride (LiF), cesium fluoride (CsF), or calcium fluoride ($CaF_2$) can be used. For example, a layer of a material having an electron transporting property containing an alkali metal, an alkaline earth metal, or a compound thereof, specifically a layer of Alq containing magnesium (Mg), can be used. By using a layer of a substance having an electron transporting property containing an alkali metal or an alkaline earth metal as the electron injecting layer, electron injection from the second electrode 104 is performed efficiently, which is preferable.

As a substance for forming the second electrode 104, a metal, an alloy, an electrically conductive compound, a mixture thereof, or the like having a low work function (specifically 3.8 eV or less) can be used. As a specific example of such a cathode material, an element belonging to group 1 or 2 in the periodic table, that is, an alkali metal such as lithium (Li) or cesium (Cs); an alkaline earth metal such as magnesium (Mg), calcium (Ca), or strontium (Sr); an alloy containing the element belonging to group 1 or 2 (MgAg or AILi); a rare-earth metal such as europium (Eu) or ytterbium (Yb); an alloy thereof; or the like can be used. However, when the electron injecting layer is provided between the second electrode 104 and the electron transporting layer, the second electrode 104 can be formed from any of a variety of conductive materials such as Al, Ag, TO, or indium oxide-tin oxide including silicon or silicon oxide regardless of its work function. These conductive materials can be formed by a sputtering method, an ink-jet method, a spin coating method, or the like.

Various methods can be used for forming the EL layer 103, regardless of a dry method or a wet method. For example, a vacuum evaporation method, an ink-jet method, a spin coating method, or the like may be used. In addition, different film formation methods may be used for forming the respective electrodes or layers. In addition, when a film is formed using the triarylamine derivative described in Embodiment 1 by a vacuum evaporation method or when the above triarylamine derivative is purified by a sublimation purification method, it is preferable to select a triarylamine derivative having molecular weight of 1000 or less, preferably 800 or less, for the triarylamine derivative in order to avoid influence on the triarylamine derivative due to heat In addition, in order to improve solubility in a solvent in the case of using a wet method, it is preferable to use a triarylamine derivative described in Embodiment 1, in which an alkyl group is introduced as a substituent.

Similarly, the electrodes may be formed by a wet process such as a sol-gel process or by a wet process using a metal paste. Further, the electrode may be formed by a dry method such as a sputtering method or a vacuum evaporation method.

In the light-emitting element according to one embodiment of the present invention having the structure as described above, the potential difference generated between the first electrode 102 and the second electrode 104 makes a current flow, whereby holes and electrons are recombined in the light-emitting layer 113 that is a layer containing high light-emitting property and thus light is emitted. That is, the light-emitting element of the present invention has a structure in which a light-emitting region is formed in the light-emitting layer 113.

The light emission is extracted out through one of or both the first electrode 102 and the second electrode 104. Therefore, one of or both the first electrode 102 and the second electrode 104 is/are formed using an electrode having a light transmitting property. In the case where only the first electrode 102 has a light transmitting property, light emission is extracted from a substrate side through the first electrode 102. Alternatively, when only the second electrode 104 has a light-transmitting property, light emission is extracted from the side opposite to the substrate through the second electrode 104. When each of the first electrode 102 and the second electrode 104 has a light-transmitting property, light emission is extracted from both the substrate side and the side opposite to the substrate side through the first electrode 102 and the second electrode 104.

The structure of the layers provided between the first electrode 102 and the second electrode 104 is not limited to the above one. However, it is preferable to use a structure in which a light-emitting region where holes and electrons are recombined is provided away from the first electrode 102 and the second electrode 104 so as to prevent quenching due to the proximity of the light-emitting region and a metal used for the electrode or the carrier (electron or hole) injecting layer. The order of stacking the layers is not limited to the above, and the following order, which is opposite to the layers in FIG. 1A, may be employed: the second electrode, the electron injecting layer, the electron transporting layer, the light-emitting layer, the hole transporting layer, the hole injecting layer, and the first electrode from the substrate side.

In addition, as for the hole transporting layer or the electron transporting layer in direct contact with the light-emitting layer, particularly a carrier (electron or hole) transporting layer in contact with a side closer to a light-emitting region in the light-emitting layer 113, in order to suppress energy transfer from an exciton which is generated in the light-emitting layer, it is preferable that an energy gap thereof be larger than an energy gap of a light-emitting substance which forms the light-emitting layer or an energy gap of a light-emitting substance included in the light-emitting layer.

Since, the triarylamine derivative described in the Embodiment 1, which has a large energy gap, is used as the hole transporting layer in the light-emitting element of this embodiment, light emission having favorable color purity can be obtained efficiently even when the light-emitting substance having a large energy gap that emits blue light is used. Accordingly, a light-emitting element having lower power consumption can be provided. Specifically, since the energy gap of the triarylamine derivative described in Embodiment 1 is about 3.0 eV to 3.4 eV, the triarylamine derivative can be preferably used without reduction in luminous efficiency or color purity due to energy transfer in the light-emitting element having a light-emitting layer where a light-emitting substance having an energy gap of less than or equal to the above energy gap is used. Note that the energy gap of a substance that emits blue light is about 2.7 eV to 3.0 eV.

In this embodiment, the light-emitting element is manufactured over a substrate made of glass, plastic, or the like. By forming a plurality of such light-emitting elements over a substrate, a passive matrix light-emitting device can be manufactured. In addition, for example, a thin film transistor (TFT) may be formed over a substrate made of glass, plastic, or the like, and a light-emitting element may be manufactured over an electrode electrically connected to the TFT. Accordingly, an active matrix light-emitting device which controls the driving of a light-emitting element by a TFT can be manufactured. Note that a structure of the TFT is not particularly limited. Either a staggered TFT or an inverted staggered TFT may be employed. In addition, crystallinity of a semiconductor used for the TFT is also not particularly limited, and an amorphous semiconductor or a crystalline semiconductor may be used. In addition, a driving circuit formed over a TFT substrate may be formed using an n-type TFT and a p-type TFT or any one of an n-type TFT or a p-type TFT.

The triarylamine derivative according to one embodiment of the present invention has a large energy gap; therefore, when the above triarylamine derivative is used as a light-emitting substance, a light-emitting element with sufficiently short wavelengths and high color purity for blue light emission can be obtained.

Embodiment 4

In this embodiment, a light-emitting element having a different structure from that shown in Embodiment 3 will be described.

A structure is described in which light emission is obtained from a substance having a light-emitting property by forming the light-emitting layer 113 described in Embodiment 3 in such a manner that the substance having a light-emitting property is dispersed into the triarylamine derivative described in Embodiment 1; that is, a structure in which the triarylamine derivative described in Embodiment 1 is used as the host material of the light-emitting layer 113.

Since the triarylamine derivative described in Embodiment 1 has a large energy gap, it can effectively excite other light-emitting substances to achieve light emission; therefore, the triarylamine derivative described in Embodiment 1 can be preferably used as the host material and light emission resulted from the light-emitting substance can be obtained. Therefore, a light-emitting element having high luminous efficiency with small energy loss can be obtained. In addition, a light-emitting element which can easily provide light emission of a desired color that is derived from the light-emitting substance can be formed. Accordingly, a light-emitting element which emits light with high color purity can be easily obtained.

Here, there is no particular limitation on a light-emitting substance dispersed into the triarylamine derivative described in Embodiment 1, and various materials can be used.

Specifically, as a fluorescent light-emitting material, the following materials having an emission wavelength of 450 nm or more can be given in addition to N,N'-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), and the like: 4-(9H-carbazol-9-yl)-4'-(9,10-diphenyl-2-antbryl)triphenylamine (abbreviation: 2YGAPPA); N,9-diphenyl-N-[4-(10-phenyl-9-anthryl)phenyl]-9H-carbazol-3-amine (abbreviation: PCAPA); perylene; 2,5,8,11-tetra-tert-butylperylene (abbreviation: TBP); 4-(10-phenyl-9-anthryl)-4'-(9-phenyl-9H-carbazol-3-yl)phenylamine (abbreviation: PCBAPA); N,N'-(2-tert-butylanthracene-9,10-diyldi-4,1-phenylene)bis[N,N',N'-triphenyl-1,4-phenylenediamine] (abbreviation: DPABPA); N,9-diphenyl-N-[4-(9,10-diphenyl-2-anthryl)phenyl]-9H-carbazol-3-amine (abbreviation: 2PCAPPA); N-[4-(9,10-diphenyl-2-anthryl)phenyl]-N,N',N''-triphenyl-1,4-phenylendiamine (abbreviation: 2DPAPPA); N,N,N',N',N'',N'',N''',N'''-octaphenyldibenzo[g,p]chrysene-2,7,10,15-tetramine (abbreviation: DBC1); coumarin 30; N-(9,10-diphenyl-2-anthryl)-N,9-diphenyl-9H-carbazol-3-amine (abbreviation: 2PCAPA); N-[9,10-bis(1,1'-biphenyl-2-yl)-2-anthryl]-N,9-diphenyl-9H-carbazol-3-amine (abbreviation: 2PCABPhA); N-(9,10-diphenyl-2-anthryl)-N,N,N-triphenyl-1,4-phenylenediamine (abbreviation: 2DPAPA); N-[9,10-bis(1,1'-biphenyl-2-yl)-2-anthryl]-N,N,N-triphenyl-1,4-phenylenediamine (abbreviation: 2DPABPhA); 9,10-bis(1,1'-biphenyl-2-yl)]-N-[4-(9H-carbazol-9-yl)phenyl]-N-phenylanthracen-2-amine (abbreviation: 2YGABPhA); N,N,9-triphenylanthracen-9-amine (abbreviation: DPhAPhA); coumarin 545T, N,N'-diphenylquinacridone (abbreviation: DPQd); rubrene; 5,12-bis(1,1'-biphenyl-4-yl)-6,11-diphenyltetracene (abbreviation: BPT); 2-(2-{2-(dimethylamine)phenyl]ethenyl}-6-methyl-4H-pyran-4-yliden)propanedinitrile (abbreviation: DCM1); 2-{2-methyl-6-[2-(2,3,6,7-tetrahydro-1H,5H-benzo[ij]quinolizin-9-yl)ethenyl]-4H-pyan-4-ylidene}propanedinitrile (abbreviation: DCM2); N,N,N',N'-tetrakis(4-methylphenyl)tetracene-5,11-diamine (abbreviation: p-mPhTD); 7,13-diphenyl-N,N,N',N-tetrakis (4-methylphenyl)acenaphtho[1,2-a]fluoranthene-3,10-diamine (abbreviation: p-mPhAFD); 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI); 2-{2-tert-butyl-6-[2-(1,1,7,7-tetramethyl-2,3,6,7-tetrahydro-1H,5H-benzo[ij]quinolizin-9-yl) ethenyl]-4H-pyran-4-ylidene}propanedinitrile (abbreviation: DCJTB); 2-(2,6-bis{2-[4-(dimethylamino)phenyl] ethenyl}-4H-pyran-4-ylidene)propanedinitrile (abbreviation: BisDCM); 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM); and the like.

As a phosphorescent light-emitting material, in addition to bis[2-(4',6'-difluorophenyl)pyridinato-N,$C^{2'}$]iridium(III) tetrakis(1-pyrazolyl)borate (abbreviation: FIr6), materials having an emission wavelength in the range of 470 nm to 500 nm, such as bis[2-(4',6'-difluorophenyl)pyridinato-N,$C^{2'}$]iridium(III)picolinate (abbreviation: FIrpic); bis[2-(3',5'-bistrifluoromethylphenyl)pyridinato-N,$C^{2'}$]iridium(III) picolinate (abbreviation: Ir($CF_3$ppy)$_2$(pic)); and bis[2-(4',6'-difluorophenyl)pyridinato-N,$C^{2'}$]iridium(III)acetylacetonate (abbreviation: FIracac) can be given, and materials having an emission (green light emission) wavelength of 500 nm or more can be given, such as tris(2-phenylpyridinato)iridium (III) (abbreviation: Ir(ppy)$_3$); bis(2-phenylpyridinato)iridium(III) acetylacetonate (abbreviation: Ir(ppy)$_2$(acac)); tris(acetylacetonatoxmonophenanthroline)terbium (III) (abbreviation: Tb(acac)$_3$(Phen)); bis(benzo[h]quinolinato)iridium(III)acetylacetonate (abbreviation: Ir(bzq)$_2$(acac)); bis(2,4-diphenyl-1,3-oxazolato-N,$C^{2'}$)iridium(III)acetylacetonate (abbreviation: Ir(dpo)$_2$(acac)); bis[2-(4'-perfluorophenylphenyl)pyridinato]iridium(I)acetylacetonate (abbreviation: Ir(p-PF-ph)$_2$(acac)); bis(2-phenylbenzothiazolato-N, $C^{2'}$)iridium(III)acetylacetonate (abbreviation: Ir(bt)$_2$(acac)); bis[2-(2'-benzo[4,5-α]thienyl)pyridinato-N,$C^{3'}$]iridium(III) acetylacetonate (abbreviation: Ir(btp)$_2$(acac)); bis(1-phenylisoquinolinato-N,$C^{2'}$)iridium(III)acetylacetonate (abbreviation: Ir(piq)$_2$(acac)); (acetylacetonato)bis[2,3-bis(4-fluorophenyl)quinoxalinato]iridium(M) (abbreviation: Ir(Fdpq)$_2$(acac)); (acetylacetonato)bis(2,3,5-triphenylpyrmzinato)iridium(III) (abbreviation: Ir(tppr)$_2$(acac)); 2,3,7,8,12,13,17,18-octaethyl-21H,23H-porphyrinplatinum (II) (abbreviation: PtOEP); tris(1,3-diphenyl-1,3-propanedionato)(monophenanthroline)europium(II) (abbreviation: Eu(DBM)$_3$(Phen)); and tris[1-(2-thenoyl)-3,3,3-trifluoroacetonato](monophenanthroline)europium (III) (abbreviation: Eu(TTA)$_3$(Phen)).

Among the materials described above, when the fluorescent light-emitting substance having an emission wavelength of 450 nm or more or the phosphorescent light-emitting substance having an emission wavelength of 470 nm or more, preferably 470 nm or more and more preferably 500 nm or more, is used as the light-emitting substance, reduction in luminous efficiency or color purity unlikely occurs, and thus a light-emitting element having preferable luminous efficiency with high color purity can be obtained. Accordingly, a light-emitting element having lower power consumption can be provided. Further, other organic compounds may be dispersed at the same time in addition to the triarylamine derivative described in Embodiment 1 and the light-emitting substance dispersed into the triarylamine derivative. In this case, a substance that improves carrier balance of the light-emitting layer is preferable and the above substance having a high electron transporting property and the like are given, and a substance that has an energy gap as wide as the triarylamine derivative according to one embodiment of the present invention is preferable.

Note that other than the light-emitting layer 113, the structure described in Embodiment 3 can be used as appropriate; however, as the hole transporting layer 112, other than the materials shown in Embodiment 3, a substance having a high hole transporting property such as the following aromatic amine compounds can be used 4,4'-bis[N-(1-naphthyl)-N-phenylamino]biphenyl (abbreviation: NPB); N,N-bis(3-methylphenyl)-N,N-diphenyl-[1,1'-biphenyl]-4,4'-diamine (abbreviation: TPD); 4,4',4"-tris(N,N-diphenylamino)triphenylamine (abbreviation: TDATA); 4,4',4"-tris[N-(3-methylphenyl)-N-phenylamino]triphenylamine (abbreviation: MTDATA); 4,4'-bis[N-(spiro-9,9'-bifluoren-2-yl)-N-phenylamino]-1,1'-biphenyl (abbreviation: BSPB); and the like. The substances described here are mainly substances having an electron mobility of 106 cm$^2$Ns or more. Note that a substance other than the above substances may be used as long as it has a higher hole transporting property than an electron transporting property. Note that the layer containing a substance having a high hole transporting property is not limited to a single layer, and two or more layers made of the above substances may be stacked.

Further, a macromolecular compound such as poly(N-vinylcarbazole) (abbreviation: PVK) or poly(4-vinyltriphenylamine) (abbreviation: PVTPA) can also be used for the hole transporting layer 112.

Embodiment 5

In this embodiment, an embodiment of a light-emitting element with a structure in which a plurality of light-emitting units are stacked (hereinafter this type of light-emitting element is also referred to as a stacked element) is described with reference to FIG. 1B. This light-emitting element is a light-emitting element having a plurality of light-emitting units between a first electrode and a second electrode. The light-emitting units can be similar to the EL layer 103 described in Embodiments 3 or 4. That is, Embodiment 3 or 4 describes the light-emitting element having a single light-emitting unit, and this embodiment describes a light-emitting element having a plurality of light-emitting units.

Figure 1B:
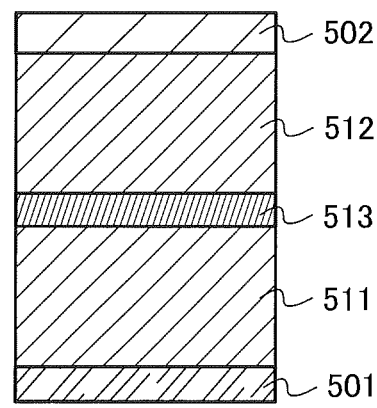

In FIG. 1B, a first light-emitting unit 511 and a second light-emitting unit 512 are stacked between a first electrode 501 and a second electrode 502, and a charge generation layer 513 is provided between the first light-emitting unit 511 and the second light-emitting unit 512. The first electrode 501 and the second electrode 502 correspond to the first electrode 102 and the second electrode 104 in Embodiment 3, respectively, and electrodes similar to those described in Embodiment 3 can be used as the first electrode 501 and the second electrode 502. Further, the first light-emitting unit 511 and the second light-emitting unit 512 may have the same structure or different structures.

The charge generation layer 513 includes a composite material of an organic compound and a metal oxide. This composite material of an organic compound and a metal oxide is the composite material described in Embodiment 3 and includes an organic compound and a metal oxide such as vanadium oxide, molybdenum oxide, or tungsten oxide. As the organic compound, any of various compounds such as an aromatic amine compound, a carbazole derivative, aromatic hydrocarbon, and a macromolecular compound (such as an oligomer, a dendrimer, and a polymer) can be used. Note that the organic compound having a hole mobility of $10^{-6}$ cm$^2$/Vs or more is preferably used as a hole transporting organic compound. Note that any substance other than the above substances may also be used as long as it is a substance in which the hole transporting property is higher than the electron transporting property. The composite of an organic compound and a metal oxide is superior in a carrier injecting property and a carrier transporting property, and accordingly, low-voltage driving and low-current driving can be realized.

Alternatively, the charge generation layer 513 may be formed with a combination of a layer containing the composite material of an organic compound and a metal oxide with a layer formed using another material. For example, the charge generation layer 513 may be formed with a combination of a layer containing the composite material of an organic compound and a metal oxide and a layer including one compound selected from electron donating substances and a compound having a high electron transporting property. Further, the charge generation layer 513 may be formed with a combination of a layer containing the composite material of an organic compound and a metal oxide with a transparent conductive film.

In any case, the charge generation layer 513 which is interposed between the first light-emitting unit 511 and the second light-emitting unit 512 is acceptable as long as electrons are injected to one light-emitting unit and holes are injected to the other light-emitting unit when a voltage is applied between the first electrode 501 and the second electrode 502. For example, in FIG. 1B, any layer can be employed as the charge generation layer 513 as long as the layer injects electrons into the first light-emitting unit 511 and holes into the second light-emitting unit 512 when voltage is applied so that the potential of the first electrode is higher than that of the second electrode.

Although the light-emitting element having two light-emitting units is described in this embodiment, a light-emitting element in which three or more light-emitting units are stacked can be employed in a similar manner. When the charge generation layer is provided between the pair of electrodes so as to partition the plural light-emitting units like the light-emitting element according to this embodiment, the element can have long lifetime in a high luminous region while keeping low current density. In the case where the light-emitting element is applied to lighting as an application example, voltage drop due to resistance of an electrode material can be reduced. Accordingly, light can be uniformly emitted with a large area. Moreover, a light-emitting device with low power consumption, which can be driven at low voltage, can be achieved.

The light-emitting units emit light having different colors from each other, thereby obtaining light emission of a desired color in the whole light-emitting element. For example, in the light-emitting element having two light-emitting units, when the emission color of the first light-emitting unit and the emission color of the second light-emitting unit are complementary colors, a light-emitting element which emits white light as a whole can be obtained. Note that "complementary color" means a relation between colors which becomes an achromatic color when they are mixed. That is, white light emission can be obtained by mixture of lights obtained from substances emitting the lights of complementary colors. The same can be applied to a light-emitting element having three light-emitting units. For example, when the first light-emitting unit emits red light, the second light-emitting unit emits green light, and the third light-emitting unit emits blue light, white light can be emitted from the whole light-emitting element.

Since the light-emitting element of this embodiment includes the triarylamine derivative described in Embodiment 1, a light-emitting element having preferable luminous efficiency can be obtained. In addition, since the light-emitting units which include the triarylamine derivative can obtain light that is derived from a light-emitting substance with favorable color purity, color of a light-emitting element as a whole is easily adjusted.

Note that this embodiment can be combined with any of other embodiments as appropriate.

Embodiment 6

This embodiment shows an example in which the triarylamine derivative described in Embodiment 1 is used for an active layer of a vertical transistor (SIT), which is a kind of organic semiconductor element.

Figure 2:
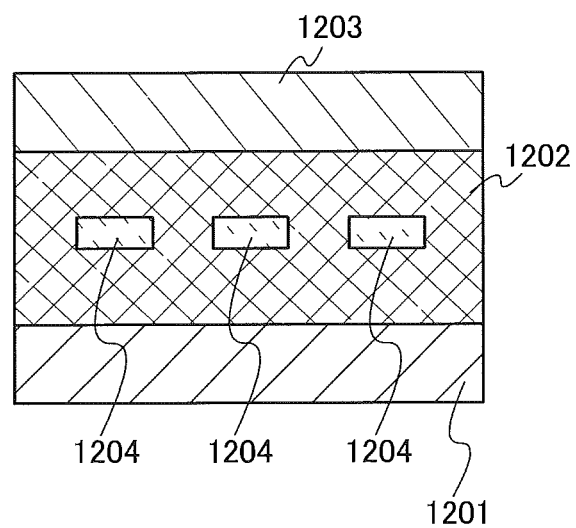
FIG. 2 is a conceptual view of an organic semiconductor element (Embodiment 6)

The element has a structure in which a thin-film active layer 1202 including a triarylamine derivative described in Embodiment 1 is interposed between a source electrode 1201 and a drain electrode 1203, and a gate electrode 1204 is embedded in the active layer 1202, as illustrated in FIG. 2. The gate electrode 1204 is electrically connected to a unit for applying a gate voltage, and the source electrode 1201 and the drain electrode 1203 are electrically connected to a unit for controlling a source-drain voltage.

In such an element structure, when a voltage is applied between the source and the drain under the condition where a gate voltage is not applied, a current flows (becomes an ON state). When a gate voltage is applied in this state, a depletion layer is generated in the periphery of the gate electrode 1204, whereby a current does not flow (becomes an OFF state). With the above mechanism, the element operates as a transistor.

In a vertical transistor, a material which has both a carrier transporting property and favorable film quality is required for an active layer like in a light-emitting element. The triarylamine derivative described in Embodiment 1 is useful because it sufficiently meets these requirements.

Embodiment 7

In this embodiment, a light-emitting device manufactured using the triarylamine derivative described in Embodiment 1 will be described.

Figure 3A:
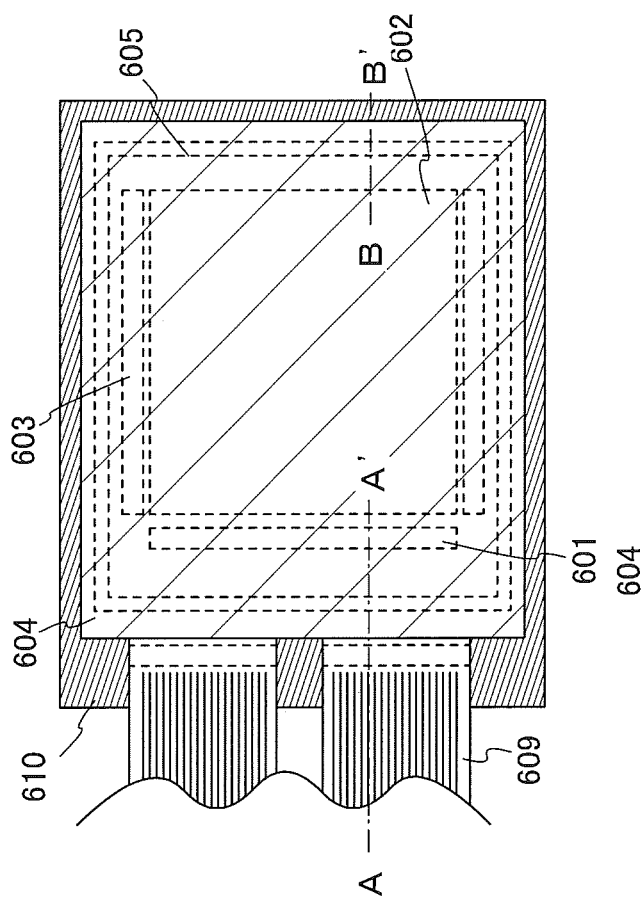
FIGS. 3A and 3B are conceptual views of an active matrix light-emitting device (Embodiment 7)
Figure 3B:
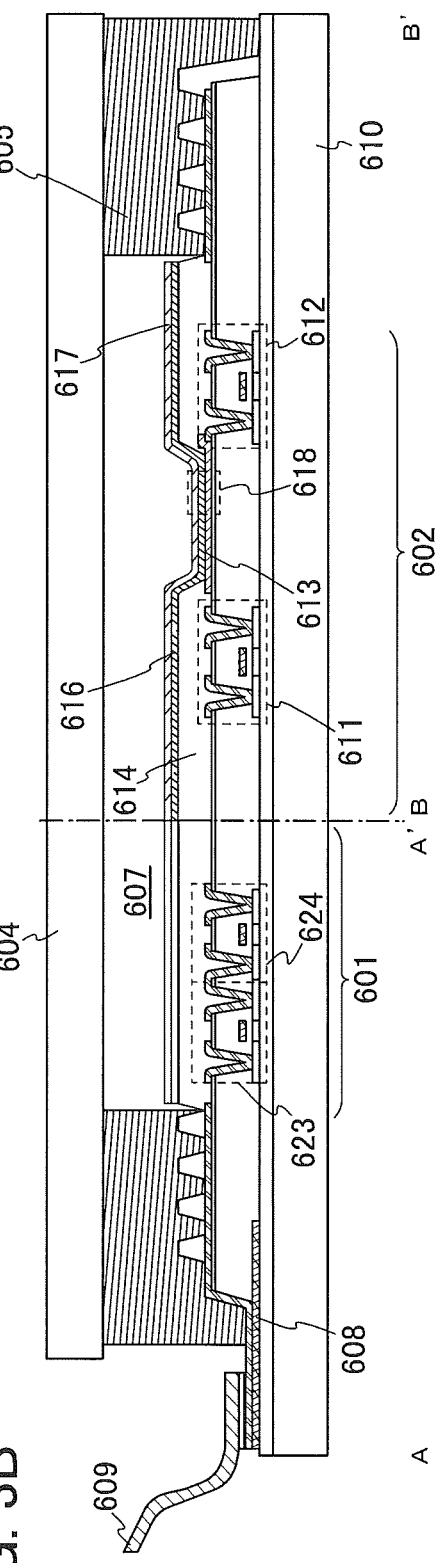

In this embodiment, a light-emitting device manufactured using the triarylamine derivative described in Embodiment 1 is described with reference to FIGS. 3A and 3B. FIG. 3A is a top view of the light-emitting device, and FIG. 3B is a cross-sectional view taken along A-A' and B-B' of FIG. 3A. This light-emitting device includes a driver circuit portion (source-side driver circuit) 601, a pixel portion 602, and a driver circuit portion (gate-side driver circuit) 603, which are indicated by dotted lines, in order to control the light emission of a light-emitting element. Moreover, reference numeral 604 denotes a sealing substrate; 605, a sealant; and 607, a space surrounded by the sealant 605

A lead wiring 608 transmits a signal to be inputted to the source-sido driver circuit 601 and the gate-side driver circuit 603 and receives a video signal, a clock signal, a start signal, a reset signal, or the like from an FPC (Flexible Printed Circuit) 609 which is an external input terminal. Although only the FPC is illustrated here, this FPC may be provided with a printed wiring board (PWB). The light-emitting device in this specification includes not only a light-emitting device body but also the light-emitting device in which an FPC or a PWB is attached thereto.

Next, a cross-sectional structure is described with reference to FIG. 3B. Although the driver circuit portion and the pixel portion are formed over an element substrate 610, the source-side driver circuit 601 which is the driver circuit portion and one pixel in the pixel portion 602 are illustrated here.

Note that a CMOS circuit in which an n-channel TFT 623 and a p-channel TFT 624 are combined is formed as the source-side driver circuit 601. The driver circuit may be formed by various CMOS circuits, PMOS circuits, or NMOS circuits. It is not always necessary to form the driver circuit on the substrate integrally as in this embodiment, and it is also possible to form the driver circuit not on the substrate but outside the substrate externally.

The pixel portion 602 has a plurality of pixels, each of which includes a switching TFT 611, a current control TFT 612, and a first electrode 613 which is electrically connected to a drain of the current control TFT 612. Note that an insulator 614 is formed to cover an end portion of the first electrode 613. Here, the insulator 614 is formed using a positive photosensitive-acrylic resin film.

In order to improve the coverage, the insulator 614 is provided such that either an upper edge portion or a lower edge portion of the insulator has a curved surface with a curvature. For example, in the case of using a positive photosensitive-acrylic as a material for the insulator 614, it is preferable to give only the upper edge portion of the insulator 614 a curved surface, having a curvature radius (of 0.2 μm to 3 μm). As the insulator 614, either a negative type which becomes insoluble in etchant by irradiation with light or a positive type which becomes soluble in etchant by irradiation with light can be used.

An EL layer 616 and a second electrode 617 are formed over the first electrode 613. Here, a material having a high work function is preferably used as a material for the first electrode 613 which serves as an anode. For example, a single-layer film of an ITO film, an indium tin oxide film containing silicon, an indium oxide film containing 2 wt % to 20 wt % of zinc oxide, a titanium nitride film, a chromium film, a tungsten film, a Zn film, a Pt film, or the like can be used. Besides these single-layer films, a stack of a titanium nitride film and a film containing aluminum as its main component; a stack of three layers of a titanium nitride film, a film containing aluminum as its main component, and a titanium nitride film; or the like can be used. Note that when a stacked structure is employed, resistance of a wiring is low, and a favorable ohmic contact is obtained.

The EL layer 616 is formed by various methods such as an evaporation method using an evaporation mask, an inkjet method, or a spin coating method. The EL layer 616 contains the triarylamine derivative described in Embodiment 1. Further, the EL layer 616 may also be formed using another material including a low molecular compound or a macromolecular compound (including an oligomer or a dendrimer).

As a material used for the second electrode 617, which is formed over the EL layer 616 and serves as a cathode, a material having a low work function (Al, Mg, Li, Ca, or an alloy or a compound thereof such as MgAg, MgIn, AlLi, LiF, or $CaF_2$) is preferably used. In the case where light generated in the EL layer 616 passes through the second electrode 617, the second electrode 617 is preferably formed using a stack of a thin metal film with a reduced thickness and a transparent conductive film (ITO, indium oxide containing 2 wt % to 20 wt % of zinc oxide, indium tin oxide containing silicon, zinc oxide (ZnO), or the like).

In addition, a light-emitting element 618 includes the first electrode 613, the EL layer 616, and the second electrode 617. The light-emitting element 618 has any of the structures described in Embodiments 3 to 5. Further, the pixel portion, which includes a plurality of light-emitting elements, in the light-emitting device of this embodiment may include both the light-emitting element with any of the structures described in Embodiments 3 to 5 and the light-emitting element with a structure other than those.

When the sealing substrate 604 and the element substrate 610 are attached to each other with the sealant 605, the light-emitting element 618 is provided in the space 607 surrounded by the element substrate 610, the sealing substrate 604, and the sealant 605. There are also cases where the space 607 is filled with an inert gas (such as nitrogen or argon) as such a filler, or where the space 607 is filled with the sealant 605.

As the sealant 605, an epoxy resin is preferably used. In addition, it is preferable to use a material that allows permeation of moisture or oxygen as little as possible. As the sealing substrate 604, a plastic substrate formed of FRP (Fiberglass-Reinforced Plastics), PVF (polyvinyl fluoride), polyester, acrylic, or the like can be used besides a glass substrate or a quartz substrate.

As described above, the light-emitting device manufactured using the triarylamine derivative described in Embodiment 1 can be obtained.

Since the triarylamine derivative described in Embodiment 1 is used for the light-emitting device according to one embodiment of the present invention, preferable characteristics can be obtained. Specifically, since the triarylamine derivative described in Embodiment 1 has a large energy gap and can suppress energy transfer from a light-emitting substance, a light-emitting element having preferable luminous efficiency can be provided and thus a light-emitting device which consumes less power can be obtained according to one embodiment of the present invention. In addition, since light emission having high color purity, especially preferable blue light emission can also be obtained, a light-emitting device having excellent color reproducibility and high display quality can be obtained.

Figure 4A:
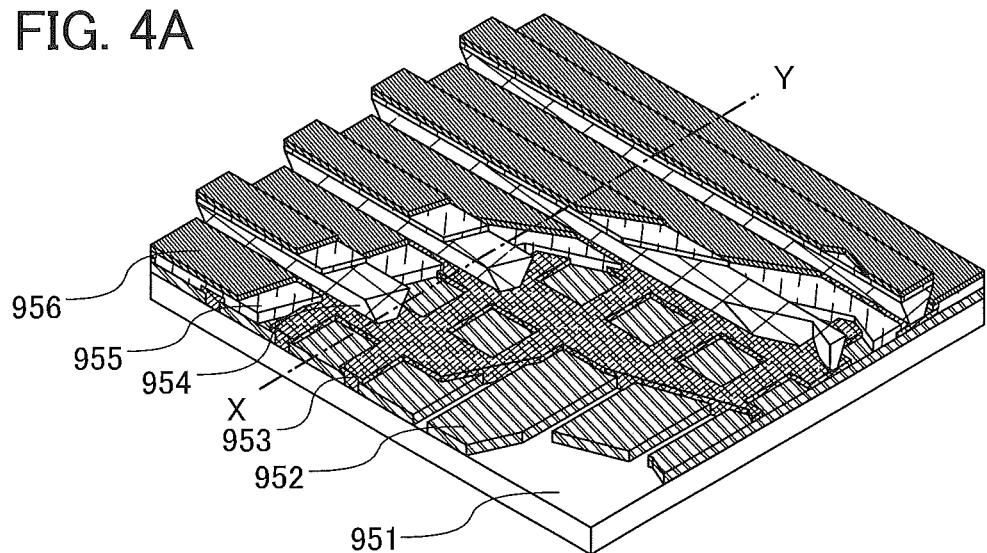
FIGS. 4A and 4B are conceptual views of a passive matrix light-emitting device (Embodiment 7)
Figure 4B:
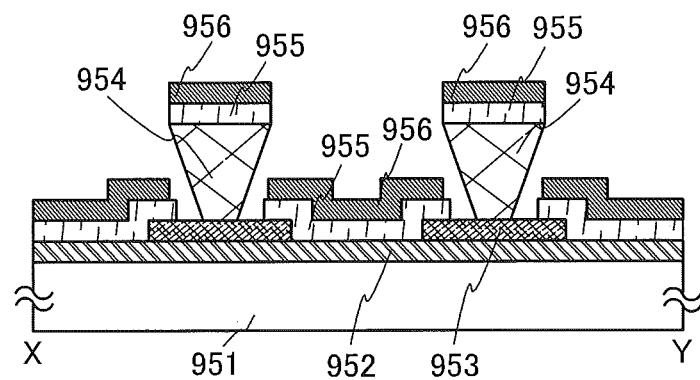

Although an active matrix light-emitting device is described in this embodiment as described above, a passive matrix light-emitting device may be alternatively manufactured. FIGS. 4A and 4B illustrate a passive matrix light-emitting device manufactured by applying one embodiment of the present invention. FIG. 4A is a perspective view of the light-emitting device, and FIG. 4B is a cross-sectional view taken along X-Y of FIG. 4A. In FIGS. 4A and 4B, an EL layer 955 is provided over a substrate 951 and between an electrode 952 and an electrode 956. The edge of the electrode 952 is covered with an insulating layer 953. A partition wall layer 954 is provided on the insulating layer 953. Sidewalls of the partition wall layer 954 have a slant such that a distance between one sidewall and the other sidewall becomes shorter as the sidewalls gets closer to the substrate surface. That is, a cross section in the direction of a narrow side of the partition wall layer 954 has a trapezoidal shape, and a lower base (a side facing a similar direction as a surface direction of the insulating layer 953, and is in contact with the insulating layer 953) is shorter than an upper base (a side facing a similar direction as the surface direction of the insulating layer 953, and is not in contact with the insulating layer 953). By providing the partition wall layer 954 in this manner, defects of the light-emitting element due to static charge and the like can be prevented. The passive matrix light-emitting device can also be driven with low power consumption when it includes the light-emitting element according to one embodiment of the present invention, which operates at a low driving voltage.

Embodiment 8

In this embodiment, an electronic device according to one embodiment of the present invention including the light-emitting device described in Embodiment 7 in part thereof will be described. The electronic device according to one embodiment of the present invention includes the triarylamine derivative described in Embodiment 1 and thus an electronic device having a display portion which consumes less power can be obtained. In addition, an electronic device having a display portion with excellent color reproducibility and high display quality can be obtained.

Examples of electronic devices each having a light-emitting element formed using the triarylamine derivative described in Embodiment 1 include a camera such as a video camera or a digital camera, a goggle type display, a navigation system, an audio playback device (e.g., a car audio component, an audio component, and the like), a computer, a game machine, a portable information terminal (e.g., a mobile computer, a cellular phone, a portable game machine, an electronic book, and the like), an image reproducing device provided with recording media (specifically, a device capable of reproducing recording media such as digital versatile discs (DVDs) and provided with a display device that can display the image), and the like. Such electronic devices are illustrated in FIGS. 5A to 5D.

Figure 5A:
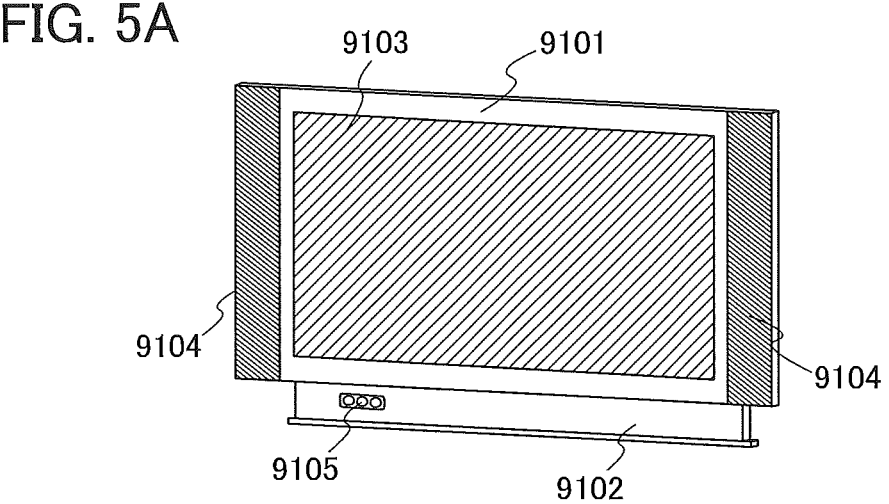
FIGS. 5A to 5D are views each illustrating an electronic device (Embodiment 8)

FIG. 5A illustrates a television device according to one embodiment of the present invention, which includes a housing 9101, a supporting base 9102, a display portion 9103, speaker portions 9104, a video input terminal 9105, and the like. In the display portion 9103 of this television device, light-emitting elements similar to those described in any of Embodiments 3 to 5 are arranged in matrix. The luminous efficiency of the light-emitting elements is high.

The light-emitting elements are capable of emitting light of favorable colors. Therefore, this television device having the display portion 9103 which is formed using the light-emitting elements consumes less power. In addition, the television device can have excellent color reproducibility and high display quality.

Figure 5B:
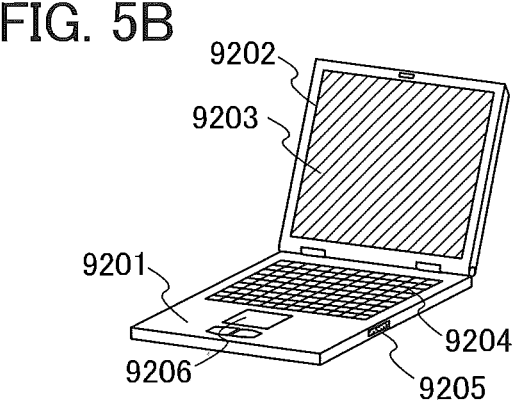

FIG. 5B illustrates a computer according to one embodiment of the present invention, which includes a main body 9201, a housing 9202, a display portion 9203, a keyboard 9204, an external connection port 9205, a pointing device 9206, and the like. In the display portion 9203 of this computer, light-emitting elements similar to those described in any of Embodiments 3 to 5 are arranged in matrix. The luminous efficiency of the light-emitting elements is high. The light-emitting elements are capable of emitting light of favorable colors. Therefore, this computer having the display portion 9203 which is formed using the light-emitting elements consumes less power. In addition, the computer can have excellent color reproducibility and high display quality.

Figure 5C:
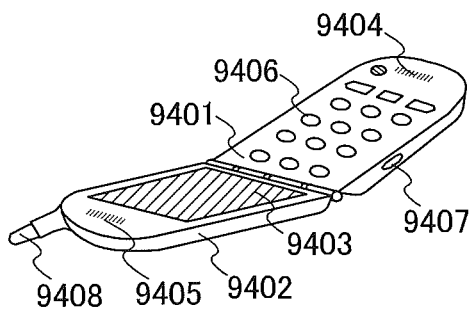

FIG. 5C illustrates a cellular phone according to one embodiment of the present invention, which includes a main body 9401, a housing 9402, a display portion 9403, an audio input portion 9404, an audio output portion 9405, operation keys 9406, an external connecting port 9407, an antenna 9408, and the like. In the display portion 9403 of this cellular phone, light-emitting elements similar to those described in any of Embodiments 3 to 5 are arranged in matrix. The luminous efficiency of the light-emitting elements is high. The light-emitting elements are capable of emitting light of favorable colors. Therefore, this cellular phone having the display portion 9403 which is formed using the light-emitting elements consumes less power. In addition, the cellular phone can have excellent color reproducibility and high display quality.

Figure 5D:
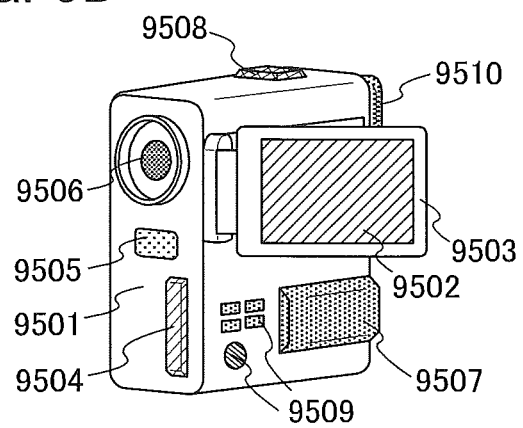

FIG. 5D illustrates a camera according to one embodiment of the present invention, which includes a main body 9501, a display portion 9502, a housing 9503, an external connecting port 9504, a remote controller receiving portion 9505, an image receiving portion 9506, a battery 9507, an audio input portion 9508, operation keys 9509, an eye piece portion 9510, and the like. In the display portion 9502 of this camera, light-emitting elements similar to those described in any of Embodiments 3 to 5 are arranged in matrix. The luminous efficiency of the light-emitting elements is high. The light-emitting elements are capable of emitting light of favorable colors. Therefore, this camera having the display portion 9502 which is formed using the light-emitting elements consumes less power. In addition, the camera can have excellent color reproducibility and high display quality.

As described above, the application range of the light-emitting device described in Embodiment 7 is so wide that the light-emitting device can be applied to electronic devices of every field. An electronic device which consumes less power can be obtained by using the triarylamine derivative described in Embodiment 1. In addition, an electronic device having a display portion capable of providing high-quality display with excellent color reproducibility can be obtained.

The light-emitting device described in Embodiment 7 can also be used as a lighting apparatus. One embodiment in which the light-emitting device described in Embodiment 7 is used as a lighting apparatus is described with reference to FIG. 6.

Figure 6:
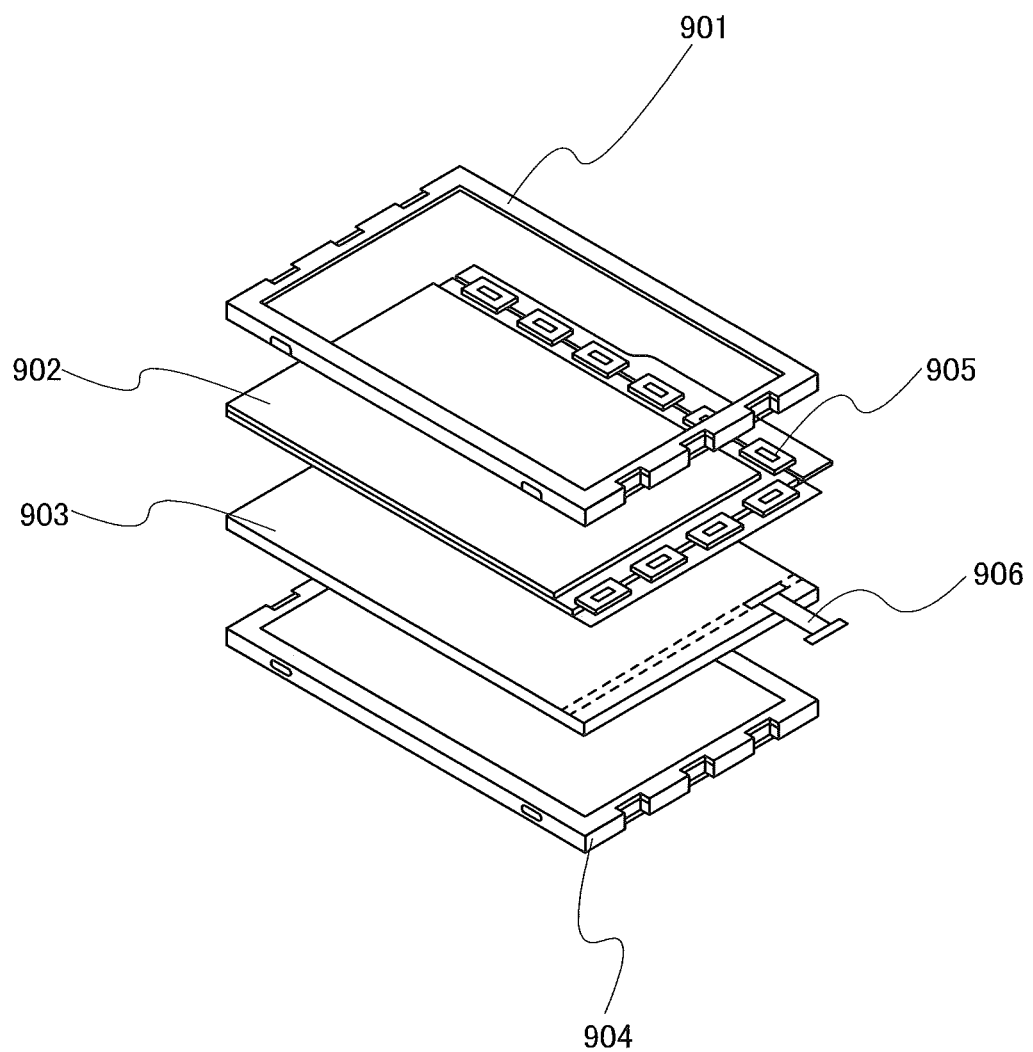
FIG. 6 is a view illustrating an electronic device (Embodiment 8)

FIG. 6 illustrates an example of a liquid crystal display device using the light-emitting device described in Embodiment 7 as a backlight. The liquid crystal display device illustrated in FIG. 6 includes a housing 901, a liquid crystal layer 902, a backlight unit 903, and a housing 904. The liquid crystal layer 902 is connected to a driver IC 905. The light-emitting device described in Embodiment 7 is used as the backlight unit 903, to which current is supplied through a terminal 906.

With the use of the light-emitting device described in Embodiment 7 as the backlight of the liquid crystal display device, the backlight consumes less power. Further, the light-emitting device described in Embodiment 7 is a lighting apparatus with plane light emission and can have a large area. Therefore, the backlight can have a large area, and a liquid crystal display device having a large area can be obtained. Furthermore, since the light-emitting device described in Embodiment 7 is thin, it becomes possible to reduce the thickness of a display device.

Figure 7:
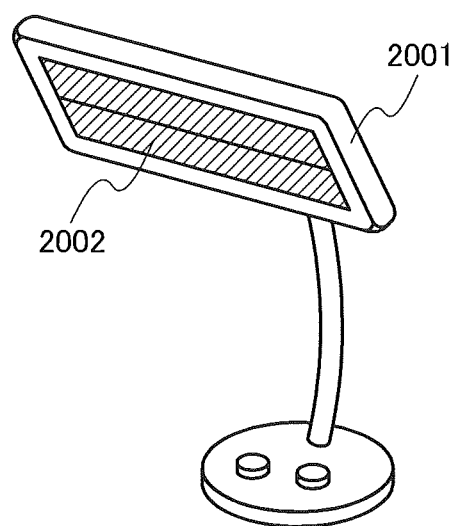
FIG. 7 is a view illustrating a lighting apparatus (Embodiment 8)

FIG. 7 illustrates an example in which the light-emitting device described in Embodiment 7 is used as a table lamp which is a lighting apparatus. The table lamp illustrated in FIG. 7 includes a housing 2001 and a light source 2002, and the light-emitting device described in Embodiment 7 is used as the light source 2002.

Figure 8:
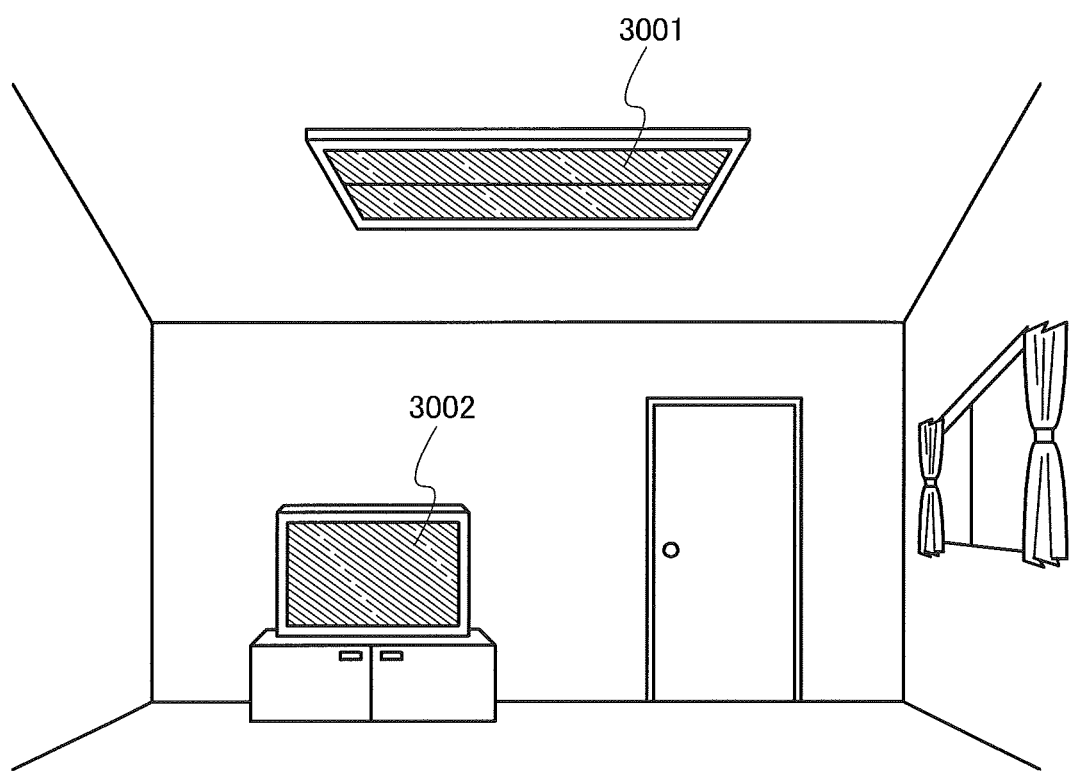
FIG. 8 is a view illustrating a lighting apparatus (Embodiment 8)

FIG. 8 illustrates an example in which the light-emitting device described in Embodiment 7 is used as an indoor lighting apparatus 3001. Since the light-emitting device described in Embodiment 7 consumes less power, a lighting apparatus that consumes less power can be obtained. Further, since the light-emitting device described in Embodiment 7 can have a large area, the light-emitting device can be used as a large-area lighting apparatus. Further, since the light-emitting device described in Embodiment 7 is thin, the light-emitting device can be used for a lighting apparatus having reduced thickness. In a room where the light-emitting device described in Embodiment 7 is used as the indoor lighting apparatus 3001 in this manner, a television device 3002 according to one embodiment of the present invention, as illustrated in FIG. 5A, is placed so that public broadcasting and movies can also be watched.

Example 1

Synthetic Example 1

This example is a synthetic example of 4-(1-naphthyl)-4'-phenyltriphenylamine (abbreviation: αNBA1BP), which is the triarylamine derivative described in Embodiment 1 as the structural formula (3). Hereinafter, the structure of αNBA1BP is shown.

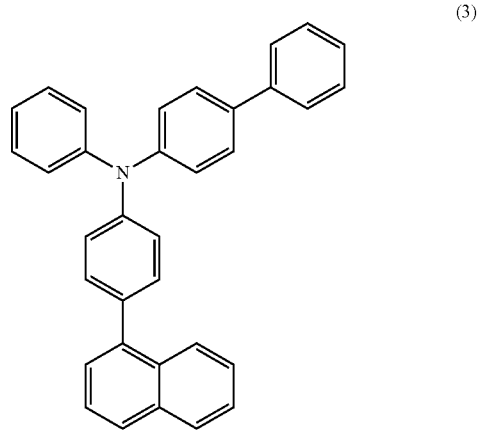 [SMILES: c1ccc(-c2ccc(N(c3ccccc3)c3ccc(-c4cccc5ccccc45)cc3)cc2)cc1]

(3)

Step 1: Synthesis of 4-phenyltriphenylamine

In a 300-mL three-neck flask, 9.3 g (40 mmol) of 4-bromobiphenyl, 6.8 g (40 mmol) of diphenylamine, 5.0 g (50 mmol) of sodium tert-butoxide, and 10 mg of bis(dibenzylideneacetone)palladium(0) were put, and 100 mL of xylene and 0.6 mL of tri(tert-butyl)phosphine (a 10 wt % hexane solution) were added to this mixture. This mixture was deaerated while being stirred under low pressure. After the deaeration, the mixture was stirred under a nitrogen atmosphere at 130° C. for 3.5 hours. After the stirring, 250 mL of toluene was added to this reaction mixture, and this suspension was filtrated through Celite (produced by Wako Pure Chemical Industries Ltd., Catalogue No. 531-16855, the same product was used hereinafter), alumina, and then Florisil (produced by Wako Pure Chemical Industries Ltd., Catalogue No. 540-00135, the same product was used hereinafter). The obtained filtrate was washed with water, and magnesium sulfate was added thereto to dry the filtrate. This mixture was filtrated through Celite, alumina, and then Florisil to obtain filtrate. The obtained filtrate was concentrated, methanol was added thereto, ultrasonic waves were applied thereto, and then recrystallization thereof was performed to obtain 11 g of an objective white powder at a yield of 89%. The synthetic scheme of Step 1 is shown in (A-1) given below.

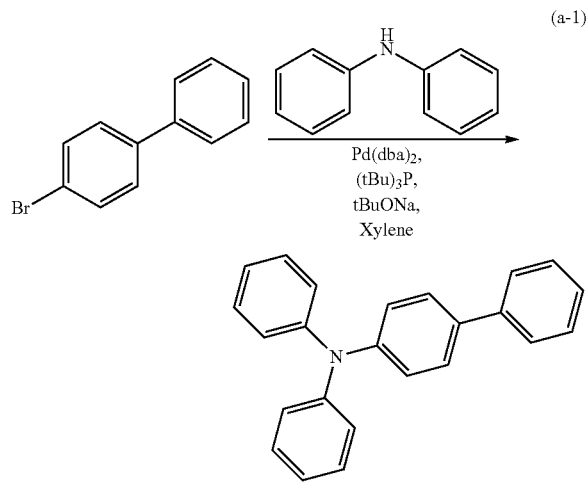

(a-1)

Step 2: Synthesis of 4-bromo-4'-phenyltriphenylamine

In a 500-mL conical flask, 6.4 g (20 mmol) of 4-phenyltriphenylamine, 250 mL of ethyl acetate, and 150 mL of toluene were added and the mixture was stirred, and then 3.6 g (20 mmol) of N-Bromosuccinimide (abbreviation: NBS) was added to this solution. After that, this mixture was stirred for 27.5 hours. After the obtained suspension was washed with water, moisture was removed by magnesium sulfate. This suspension was concentrated and dried to obtain 7.7 g of an objective white powder at a yield of 96%. A synthetic scheme of Step 2 is shown in (b-1) given below.

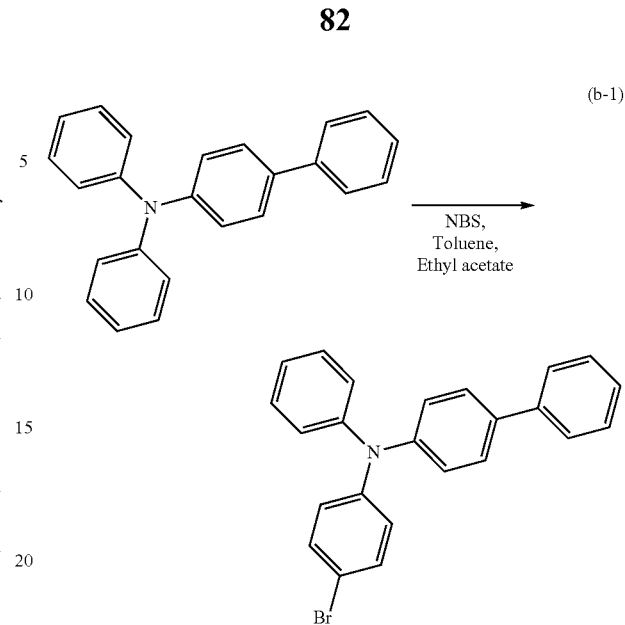

(b-1)

Step 3: Synthesis of 4-(1-naphthyl)-4'-phenyltriphenylamine (Abbreviation: αNBA1BP)]

In a 100-mL three-neck flask, 8.0 g (20 mmol) of 4-bromo-4'-phenyltriphenylamine, 3.4 g (20 mmol) of 1-naphthaleneboronic acid, 44 mg (0.2 mmol) of palladium (I) acetate, and 60 mg (0.4 mmol) of tri(o-tolyl)phosphine were put, and 20 mL of toluene, 10 mL of ethanol, and 15 mL of a potassium carbonate aqueous solution (2 mol/L) were added to this mixture. This mixture was deaerated while being stirred under low pressure. After the deaeration, the mixture was stirred under a nitrogen atmosphere at 90° C. for 2.5 hours to be reacted. After the reaction, 150 mL of toluene was added to this reaction mixture, and this suspension was filtrated through Florisil, silica gel, and then Celite. The obtained filtrate was washed with water, and magnesium sulfate was added thereto to remove moisture. This suspension was filtrated through Florisil, alumina, silica gel, and then Celite to obtain filtrate. The obtained filtrate was concentrated, methanol was added thereto, ultrasonic waves were applied thereto, and then recrystallization thereof was performed to obtain 8.6 g of an objective white solid at a yield of 97%. A synthetic scheme of Step 3 is shown in (c-1) given below.

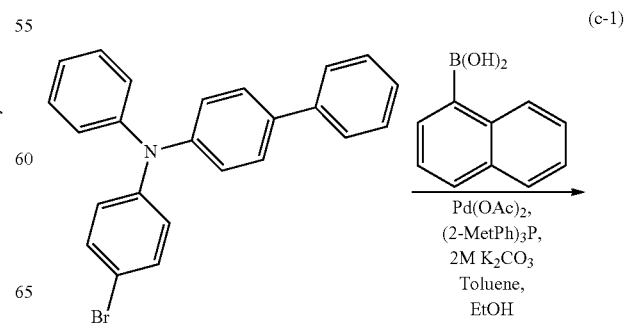

(c-1)

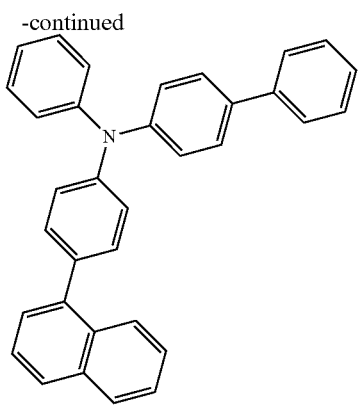

An Rf value of the objective substance by a silica gel thin layer chromatography (TLC) (developing solvent, ethyl acetate:hexane=1:10) was 0.43 and that of 4-bromo-4'-phenyltriphenylamine was 0.50.

The compound which was obtained through Step 3 described above was measured by a nuclear magnetic resonance method (1H NMR). The measurement data are shown below.

$^1$H NMR (CDCl$_3$, 300 MHz): δ (ppm)=7.07 (t, J=7.5 Hz, 1R), 7.22-7.61 (m, 17H), 7.83 (d, J=7.8 Hz, 1H), 7.88-7.91 (m, 1H), 8.02-8.05 (m, 1H)

Figure 9A:
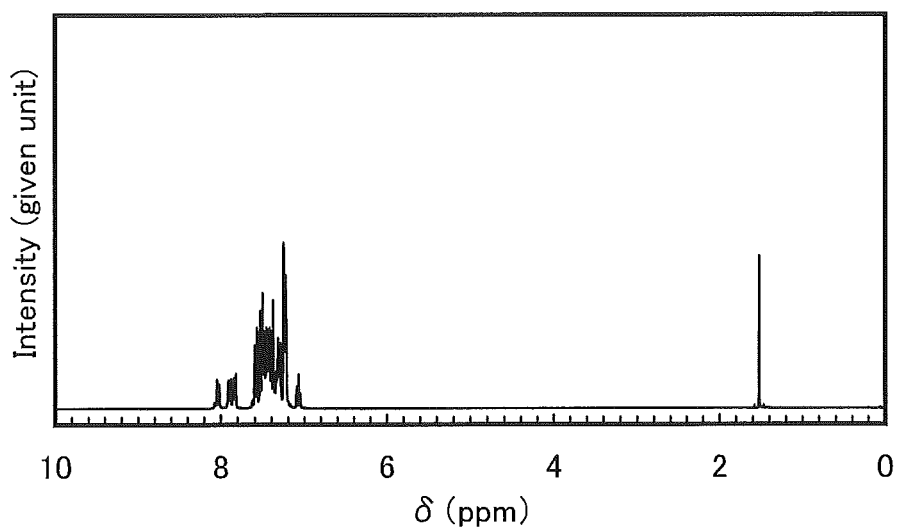
FIGS. 9A and 9B are graphs of $^1$H NMR charts of αNBA1BP.
Figure 9B:
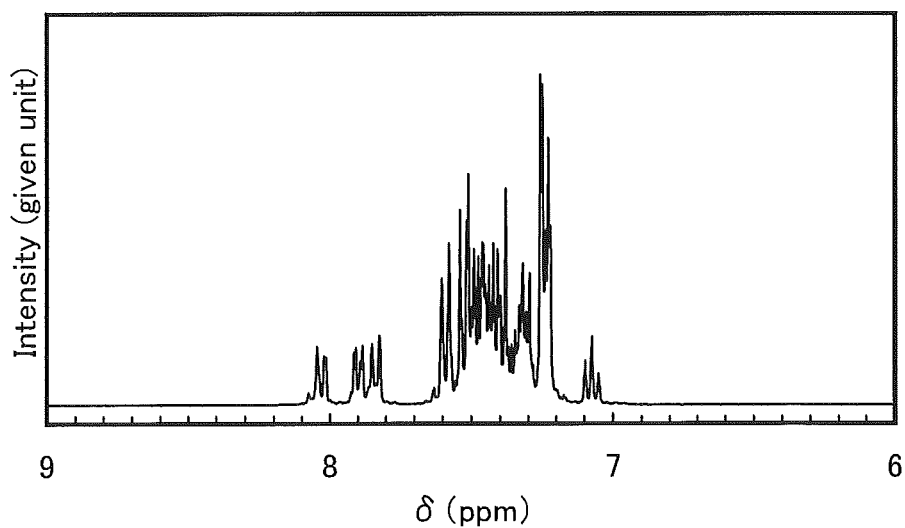

A chart of $^1$H NMR is shown in FIG. 9A. Further, FIG. 9B is a chart showing an enlarged portion in the range of 6 ppm to 9 ppm of FIG. 9A.

Subsequently, molecular weight of the above compound was measured by a Tune-of-flight mass spectrometry (abbreviation: TOF-MS) detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 448.21 (mode is ES+) was detected.

From the above measurement results, it was understood that αNBA1BP, which is the triarylamine derivative represented by the above structural formula (3), was obtained by this synthetic example.

Figure 10:
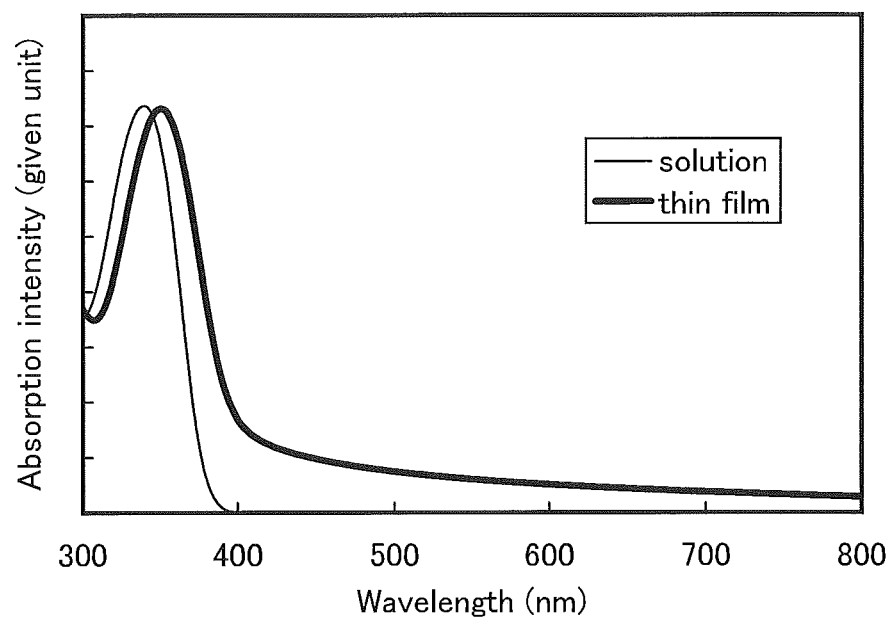
FIG. 10 is a graph of absorption spectra of αNBA1BP.

Next, FIG. 10 shows an absorption spectrum of the toluene solution of αNBA1BP and an absorption spectrum of a thin film of αNBA1BP. An ultraviolet-visible spectrophotometer (V-550, manufactured by JASCO Corporation) was used for measurement of the absorption spectra. The spectrum of the toluene solution of αNBA1BP was measured in a quartz cell. The absorption spectrum of the solution which was obtained by subtracting the quartz cell from the measured absorption spectrum is shown in FIG. 10. In addition, as for the absorption spectrum of the thin film, a sample was manufactured by evaporation of αNBA1BP over a quartz substrate, and the absorption spectrum thereof, from which the absorption spectrum of the quartz substrate is subtracted, is shown in FIG. 10. In FIG. 10, a horizontal axis represents a wavelength (nm), and a longitudinal axis represents an absorption intensity (given unit). From FIG. 10, in the case of the toluene solution of αNBA1BP, an absorption peak on a long wavelength side was observed at around 332 nm, and in the case of the thin film, an absorption peak on a long wavelength side was observed at around 339 nm.

Figure 11:
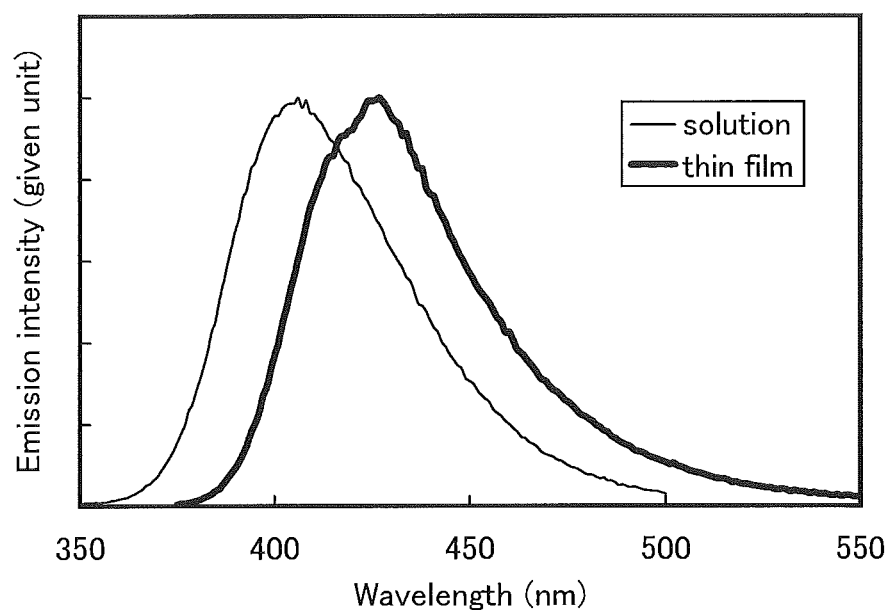
FIG. 11 is a graph of emission spectra of αNBA1BP.

Emission spectra of the toluene solution of αNBA1BP and the thin film of αNBA1BP are shown in FIG. 11. The measurement was performed using an ultraviolet-visible spectrophotometer (V-550, manufactured by JASCO Corporation) in a manner similar to that of the absorption spectra measurement. The emission spectrum of the toluene solution of αNBA1BP was measured in a quartz cell, and the emission spectrum of the thin film of αNBA1BP was measured by manufacturing a sample by evaporation of αNBA1BP over a quartz substrate. From FIG. 11, in the case of the toluene solution of αNBA1BP, the maximum emission wavelength was observed at around 404 nm (excitation wavelength: 365 nm), and in the case of the thin film, the maximum emission wavelength was observed at around 423 nm (excitation wavelength: 340 nm).

The results of measuring the thin film of αNBA1BP by photoelectron spectrometry (AC-2, product of Riken Keiki Co., Ltd.) in the atmosphere indicated that the HOMO level of αNBA1BP was −5.52 eV. The Tauc plot of the absorption spectrum of the thin film in FIG. 10 revealed that the absorption edge was 3.27 eV. Thus, the energy gap in the solid state of αNBA1BP was estimated to be 3.27 eV, which means that the LUMO level of αNBA1BP is −2.25 eV. As thus described, it was understood that αNBA1BP has a large energy gap of 3.27 eV in the solid state.

In addition, oxidation reaction characteristics of αNBA1BP were measured. The oxidation reaction characteristics were examined by a cyclic voltammetry (CV) measurement. Further, an electrochemical analyzer (ALS model 600A or 600C, manufactured by BAS Inc.) was used for the measurement.

As for a solution used for the CV measurement, dehydrated N,N-dimethylformamide (abbreviation: DMF, product of Sigma-Aldrich Inc., 99.8%, catalog No. 22705-6) was used as a solvent, and tetra-n-butylammonium perchlorate (abbreviation: n-Bu$_4$NClO$_4$, product of Tokyo Chemical Industry Co., Ltd., catalog No. T0836), which was a supporting electrolyte, was dissolved in the solvent such that the concentration of tetra-n-butylammonium perchlorate was 100 mmol/L. Further, the object to be measured was also dissolved in the solvent such that the concentration thereof was 2 mmol/L. Further, a platinum electrode (a PTE platinum electrode, manufactured by BAS Inc.) was used as a working electrode; a platinum electrode (a VC-3 Pt counter electrode (5 cm), manufactured by BAS Inc.) was used as an auxiliary electrode; and an Ag/Ag$^+$ electrode (an RE5 non-aqueous solvent reference electrode, manufactured by BAS Inc.) was used as a reference electrode. Note that the measurement was performed at room temperatures (20° C. to 25° C.). The scan speed at these CV measurements was set at 0.1 V/s.

A scan for changing the potential of the working electrode with respect to the reference electrode from 0.22V to 0.70 V and then from 0.70 V to 0.22V was set to one cycle, and measurement was performed for 100 cycles.

From the measurement results, it was understood that repetition of the oxidation reduction between an oxidation state and a neutral state had favorable characteristics in αNBA1BP without large change in oxidation peak even after 100 cycles of measurements.

Further, the HOMO level of αNBA1BP was also calculated from the CV measurement results.

First, a potential energy (eV) of the reference electrode (Ag/Ag$^+$ electrode), which was used in this example, with respect to the vacuum level was calculated. That is, the Fermi level of the Ag/Age electrode was calculated. It is known that the oxidation-reduction potential of ferrocene in methanol is +0.610 V [vs. SHE] with respect to a standard hydrogen electrode (Reference: Christian R. Goldsmith et al., J. Am. Chem. Soc., Vol. 124, No. 1, pp. 83-96, 2002). On the other hand, by using the reference electrode, which was used in this example, the oxidation-reduction potential of ferrocene in methanol was calculated to be +0.11 V [vs. Ag/Ag$^+$]. Therefore, it was understood that the potential energy of the reference electrode, which was used in this example, was lower than that of the standard hydrogen electrode by 0.50 [eV].

Here, it is also known that the potential energy of the standard hydrogen electrode with respect to the vacuum level is −4.44 eV (Reference: Toshihiro Ohnishi and Tamami Koyama, Macromolecular EL material, Kyoritsu Shuppan, pp. 64-67). As described above, it was possible to calculate the potential energy of the reference electrode, which was used in this example, with respect to the vacuum level as follows: −4.44−0.50=−4.94 [eV].

Subsequently, the calculation of the HOMO level of αNBA1BP by CV measurement is described in detail. An oxidization peak potential $E_{pa}$ of αNBA1BP was 0.61 V. In addition, a reduction peak potential $E_{pc}$ thereof was 0.54 V. Therefore, a half-wave potential (an intermediate potential between $E_{pa}$ and $E_{pc}$) can be calculated to be 0.57 V. This shows that αNBA1BP was oxidized by electric energy of 0.57 V [vs. Ag/Ag$^+$], and this energy corresponds to the HOMO level. Here, as described above, the potential energy of the reference electrode, which was used in this example, with respect to the vacuum level is −4.94 [eV]; therefore, it was understood that the HOMO level of αNBA1BP was calculated as follows: −4.94−0.57=−5.51 [eV].

Example 2

Synthetic Example 2

This example is a synthetic example of 4,4'-di-(1-naphthyl)-4"-phenyltriphenylamine (abbreviation: αNBB1BP), which is the triarylamine derivative described in Embodiment 1 as the structural formula (10). Hereinafter, the structure of αNBB1BP is shown.

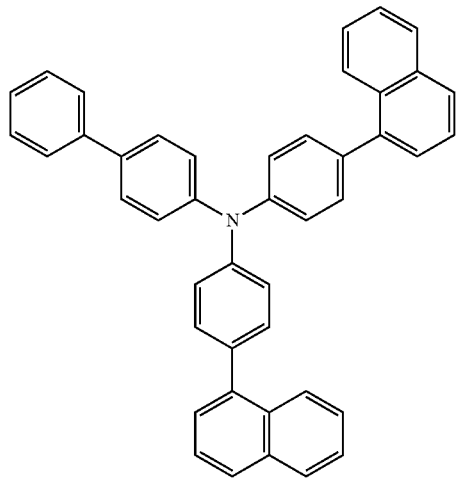

(10)

Step 1: Synthesis of 4-phenyltriphenylamine

In a manner similar to that of Step 1 in Synthetic Example 1, the synthesis was performed.

Step 2: Synthesis of 4,4'-dibromo-4"-phenyltriphenylamine

In a 300-mL conical flask, 4.8 g (15 mmol) of 4-phenyltriphenylamine which was synthesized in Step 1, 150 mL of ethyl acetate, and 100 mL of toluene were added and the mixture was stirred, and then 5.3 g (30 mmol) of N-Bromosuccinimide (abbreviation: NBS) was added to this solution. After that, this mixture was stirred for 27.5 hours. After the obtained suspension was washed with water, moisture was removed by magnesium sulfate. This suspension was concentrated and dried to obtain 7.1 g of an objective white powder at a yield of 99%. A synthetic scheme of Step 2 is shown in (b-2) given below.

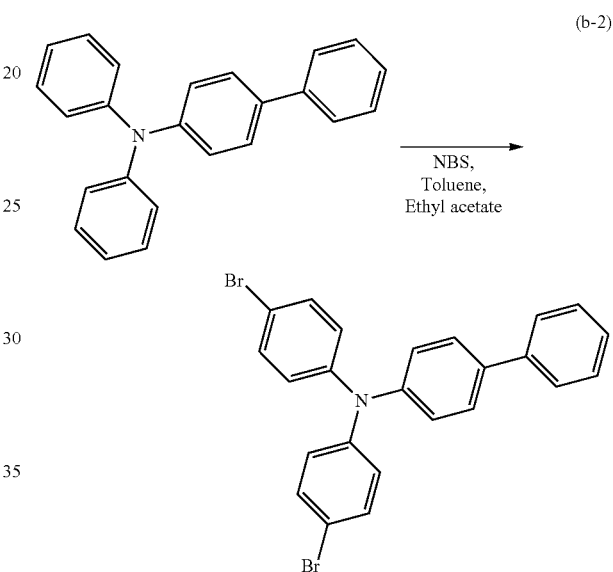

(b-2)

Step 3: Synthesis of 4,4'-di-(1-naphthyl)-4"-phenyl-triphenylamine (Abbreviation: αNBB1BP In a 100-mL three-neck flask, 1.4 g (3.0 mmol) of 4,4'-dibromo-4"-phenyltriphenylamine, 1.1 g (6.6 mmol) of 1-naphthaleneboronic acid, 33 mg (0.15 mmol) of palladium (I) acetate, and 91 mg (0.3 mmol) of tri(o-tolyl)phosphine were put, and 20 mL of toluene, 5 mL of ethanol, and 2.5 mL of a potassium carbonate aqueous solution (2 mol/L) were added to this mixture. This mixture was deaerated while being stirred under low pressure. After the deaeration, the mixture was stirred under a nitrogen atmosphere at 90° C. for 6 hours to be reacted. After the reaction, 150 mL of toluene was added to this reaction mixture, and this suspension was filtrated through Florisil, alumina, and then Celite. The obtained filtrate was washed with water, and magnesium sulfate was added thereto to dry the filtrate. After the drying, this suspension was filtrated through Florisil, alumina, and then Celite to obtain filtrate. The obtained filtrate was concentrated, methanol was added thereto, ultrasonic waves were applied thereto, and then recrystallization thereof was performed to obtain 1.2 g of an objective white solid at a yield of 53%. Synthetic scheme of Step 3 is shown in (c-2) given below.

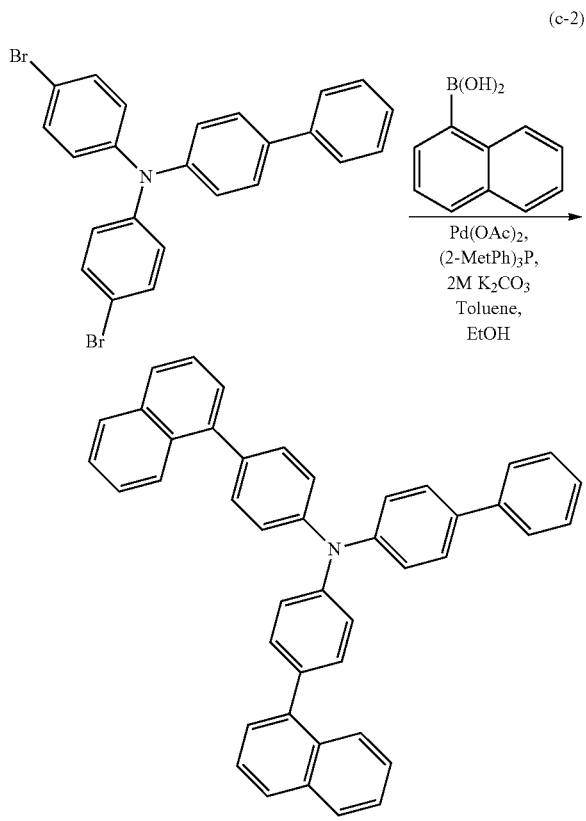

(c-2)

An Rf value of the objective substance by a silica gel thin layer chromatography (TLC) (developing solvent, ethyl acetate:hexane=1:10) was 0.59 and that of 4,4'-dibromo-4''-phenyltriphenylamine was 0.74.

The compound which was obtained through Step 3 described above was measured by a nuclear magnetic resonance method ($^1$H NMR). The measurement data are shown below.

$^1$H NMR (CDCl$_3$, 300 MHz): δ (ppm)=7.30-7.64 (m, 25H), 7.85 (d, J=7.8 Hz, 2H), 7.90-7.93 (m, 2H), 8.04-8.08 (m, 2H)

Figure 12A:
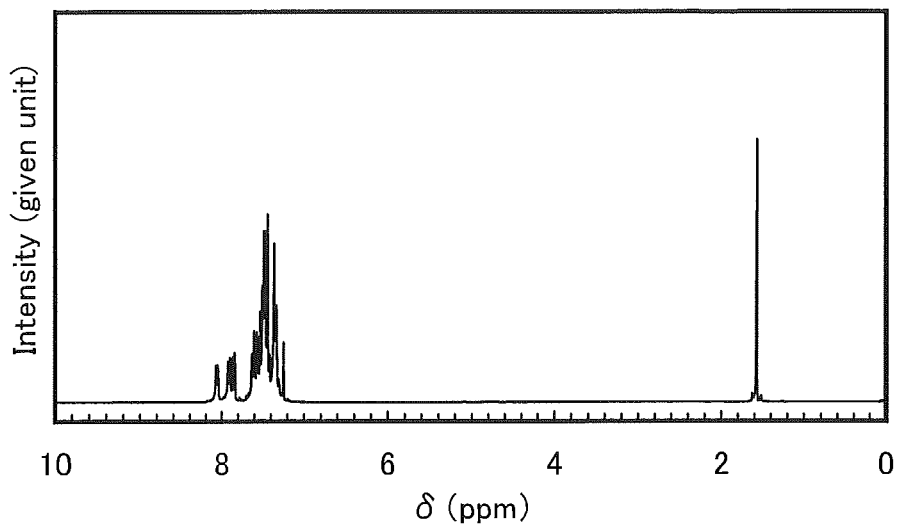
FIGS. 12A and 12B are graphs of $^1$H NMR charts of αNBB1BP.
Figure 12B:
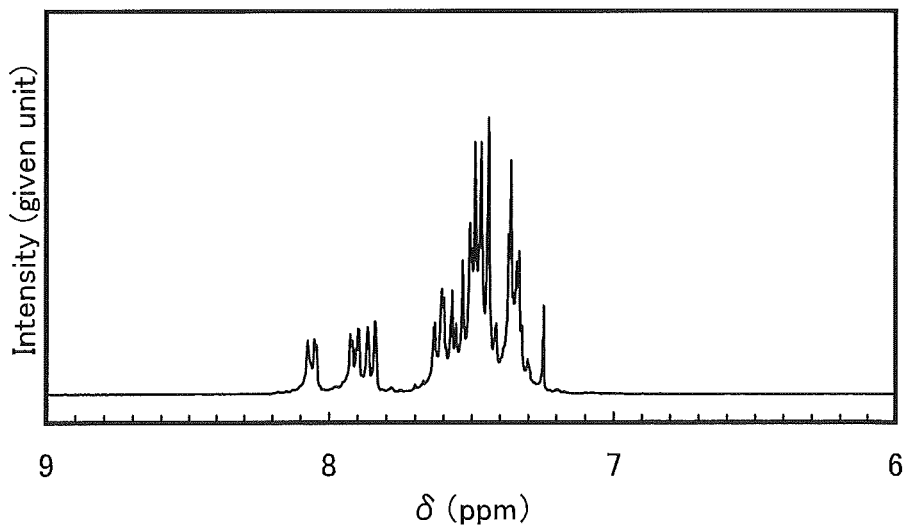

A chart of $^1$H NMR is shown in FIG. 12A. Further, FIG. 12B is a chart showing an enlarged portion in the range of 6 ppm to 9 ppm of FIG. 12A.

The molecular weight of the above compound was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 574.25 (mode is ES+) was detected.

From the above measurement results, it was understood that αNBB1BP, which is the triarylamine derivative represented by the above structural formula (10), was obtained by this synthetic example.

Figure 13:
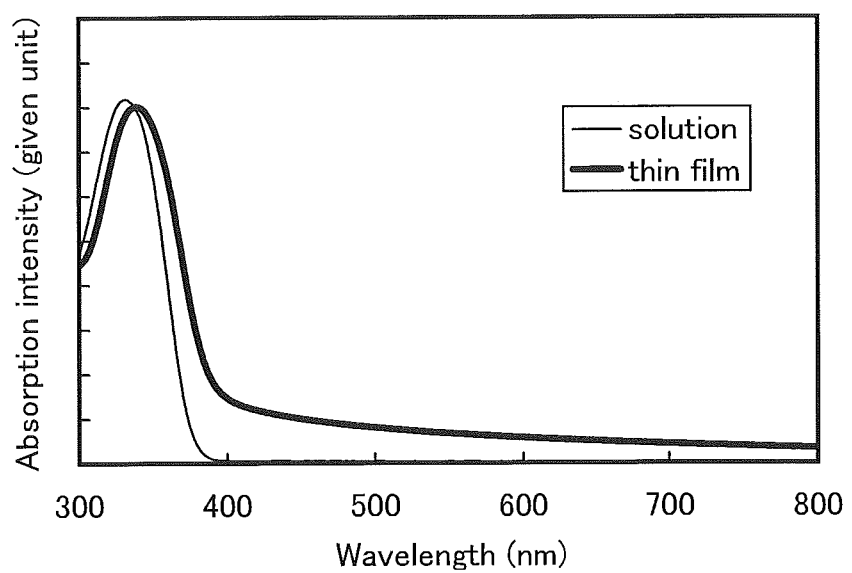
FIG. 13 is a graph of absorption spectra of αNBB1BP.

Next, FIG. 13 shows an absorption spectrum of the toluene solution of αNBB1BP and an absorption spectrum of a thin film of αNBB1BP. An ultraviolet-visible spectrophotometer (V-550, manufactured by JASCO Corporation) was used for measurement of the absorption spectra. The spectrum of the toluene solution of αNBB1BP was measured in a quartz cell. The absorption spectrum of the solution which was obtained by subtracting the quartz cell from the measured absorption spectrum is shown in FIG. 13. In addition, as for the absorption spectrum of the thin film, a sample was manufactured by evaporation of αNBB1BP over a quartz substrate, and the absorption spectrum thereof, from which the absorption spectrum of the quartz substrate is subtracted, is shown in FIG. 13. In FIG. 13, a horizontal axis represents a wavelength (nm), and a longitudinal axis represents an absorption intensity (given unit). From FIG. 13, in the case of the toluene solution of αNBB1BP, an absorption peak on a long wavelength side was observed at around 341 nm, and in the case of the thin film, an absorption peak on a long wavelength side was observed at around 351 nm.

Figure 14:
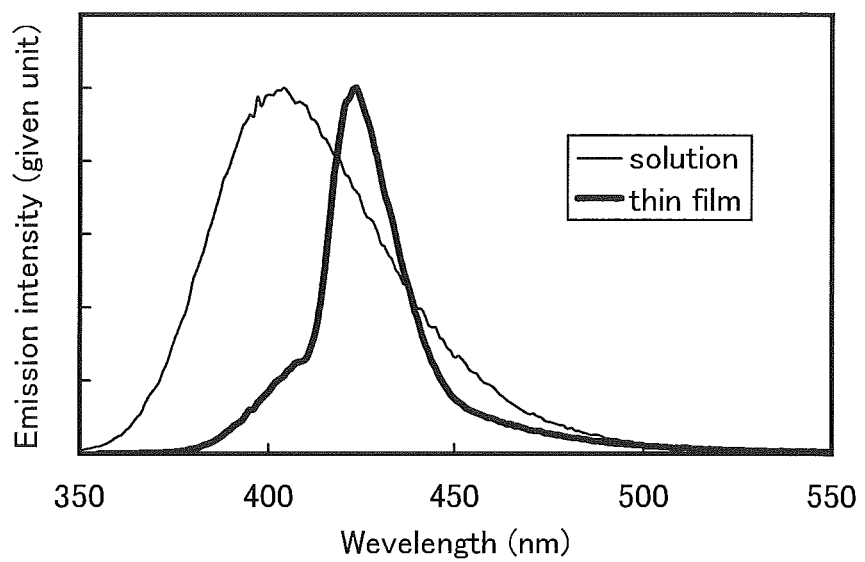
FIG. 14 is a graph of emission spectra of αNBB1BP.

Emission spectra of the toluene solution of αNBB1BP and the thin film of αNBB1BP are shown in FIG. 14. The measurement was performed using an ultraviolet-visible spectrophotometer (V-550, manufactured by JASCO Corporation) in a manner similar to that of the absorption spectra measurement. The emission spectrum of the toluene solution of αNBB1BP was measured in a quartz cell, and the emission spectrum of the thin film of αNBB1BP was measured by manufacturing a sample by evaporation of αNBB1BP over a quartz substrate. From FIG. 14, in the case of the toluene solution of αNBB1BP, the maximum emission wavelength was observed at around 408 nm (excitation wavelength: 340 nm), and in the case of the thin film, the maximum emission wavelength was observed at around 426 nm (excitation wavelength: 368 nm).

The results of measuring the thin film of αNBB1BP by photoelectron spectrometry (AC-2, product of Riken Keiki Co., Ltd.) in the atmosphere indicated that the HOMO level of αNBB1BP was −5.58 eV. The Tauc plot of the absorption spectrum of the thin film in FIG. 13 revealed that the absorption edge was 3.21 eV. Thus, the energy gap in the solid state of αNBB1BP was estimated to be 3.21 eV, which means that the LUMO level of αNBB1BP is −2.37 eV. As thus described, it was understood that αNBB1BP has a large energy gap of 3.21 eV in the solid state.

In addition, oxidation reaction characteristics of αNBB1BP were measured. The oxidation reaction characteristics were examined by a cyclic voltammetry (CV) measurement in a manner similar to that of Example 1.

From the measurement results, it was understood that repetition of the oxidation reduction between an oxidation state and a neutral state had favorable characteristics in αNBB1BP without large change in oxidation peak even after 100 cycles of measurements.

According to the calculation similar to that of Example 1, it was understood that the HOMO level of αNBB1BP was −5.50 [eV].

Example 3

Synthetic Example 3

This example is a synthetic example of 4-(1-naphthyl)-triphenylamine (abbreviation: αNBA1P), which is the triarylamine derivative described in Embodiment 1 as the structural formula (1). Hereinafter, the structure of αNBA1P is shown.

(1)

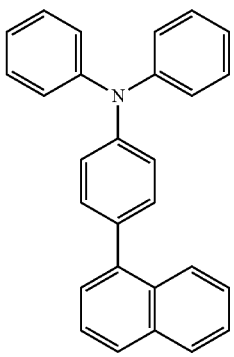

Step 1: Synthesis of 4-bromotriphenylamine

To 1.5 L of an ethyl acetate solution containing 54.0 g (220 mmol) of triphenylamine, 35.6 g (200 mmol) of N-Bromosuccinimide (abbreviation: NBS) was added. After that, this mixture was stirred for 24 hours. After the obtained suspension was concentrated to 1 L, the concentrated suspension was washed with 1 L of an aqueous solution containing 5% of sodium acetate. After the washing, this solution was further concentrated to about 50 mL. Then, methanol was added to the concentrated solution and the solution was precipitated. The obtained precipitate was filtered and dried to obtain 46.5 g of an objective white powder at a yield of 73%. A synthetic scheme of Step 1 is shown in (b-3) given below.

(b-3)

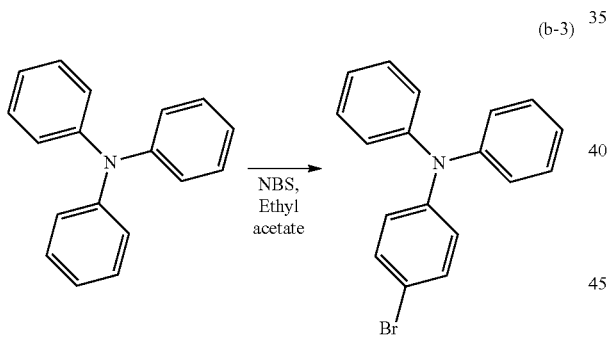

Step 2: Synthesis of 4-(1-naphthyl)-triphenylamine (Abbreviation: αNBA1P)

In a 200 mL three-neck flask, 9.7 g (30 mmol) of 4-bromotriphenylamine which was synthesized in Step 1, 5.7 g (33 mmol) of 1-naphthaleneboronic acid, 67 mg (0.3 mmol) of palladium(II) acetate, and 91 mg (0.3 mmol) of tri(o-tolyl)phosphine were put, and 50 mL of toluene, 20 mL of ethanol, and 20 mL of a potassium carbonate aqueous solution (2 mol/L) were added to this mixture. This mixture was deaerated while being stirred under low pressure. After the deaeration, the mixture was stirred under a nitrogen atmosphere at 90° C. for 2 hours to be reacted. After the reaction, 150 mL of toluene was added to this reaction mixture, and this suspension was filtrated through Florisil, silica gel, and then Celite. The obtained filtrate was washed with sodium hydrogen carbonate aqueous solution and water in this order, and magnesium sulfate was added thereto to dry the filtrate. After the drying, this suspension was filtrated through Florisil, alumina, silica gel, and then Celite to obtain filtrate. The obtained filtrate was concentrated and dried to obtain 11 g of an objective white solid at a yield of 99%. A synthetic scheme of Step 2 is shown in (c-3) given below.

(c-3)

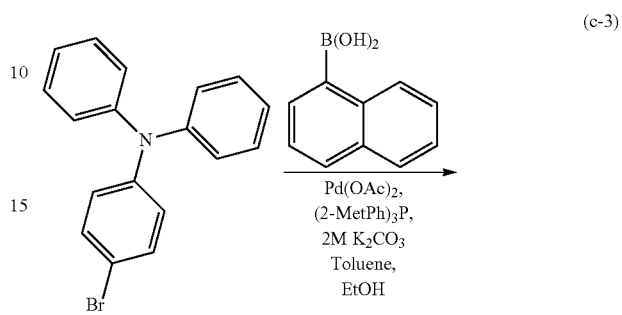

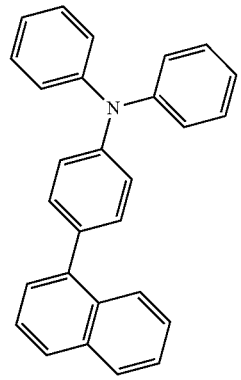

An Rf value of the objective substance by a silica gel thin layer chromatography (TLC) (developing solvent, ethyl acetate:hexane=1:10) was 0.48 and that of 4-bromotriphenylamine was 0.55.

The molecular weight of the white solid which was obtained in Step 2 was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 372.17 (mode is ES+) was detected and it was confirmed that objective αNBA1P was obtained.

Example 4

Synthetic Example 4

This example is a synthetic example of 4,4'-di-(1-naphthyl)triphenylamine (abbreviation: αNBB1P), which is the triarylamine derivative described in Embodiment 1 as the structural formula (7). Hereinafter, the structure of αNBB1P is shown.

(7)

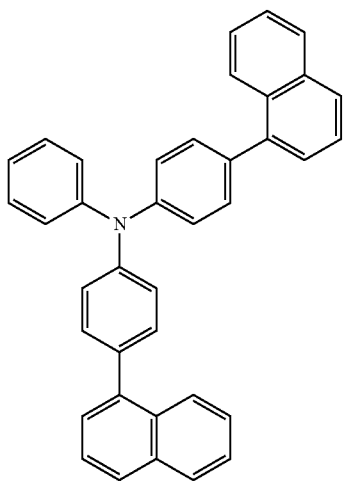

Step 1: Synthesis of 4,4'-dibromotriphenylamine

After 12 g (50 mmol) of triphenylamine was dissolved in 250 mL of ethyl acetate in a 500-mL conical flask, 18 g (100 mmol) of N-Bromosuccinimide (abbreviation: NBS) was added to this solution. After that, this mixture was stirred at room temperature for 24 hours to be reacted. After completion of the reaction, this mixture solution was washed with water, and magnesium sulfate was added thereto to remove moisture. This mixture solution was filtrated, and the obtained filtrate was concentrated and dried to obtain 20 g of an objective white solid at a yield of 99%. A synthesis scheme of Step 1 is shown in (b-4) given below.

(b-4)

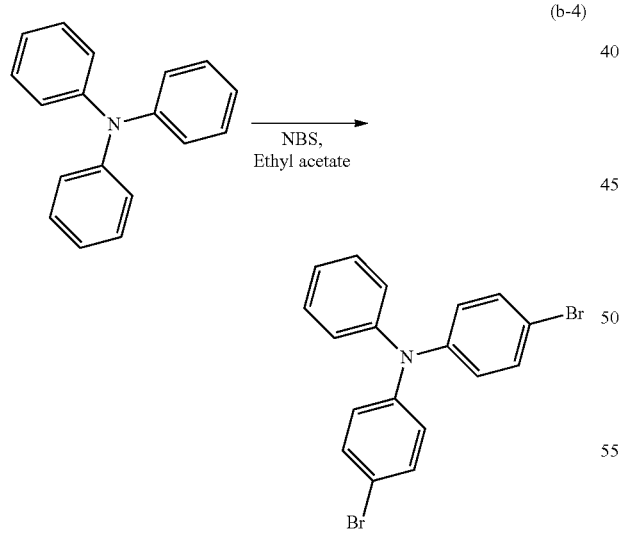

Step 2: Synthesis of 4,4'-di-(1-naphthyl)triphenylamine (Abbreviation: αNBB1P)

In a 100-mL three-neck flask, 6.0 g (15 mmol) of 4,4'-dibromotriphenylamine which was synthesized in Step 1, 5.2 g (30 mmol) of 1-naphthaleneboronic acid, 2.0 mg (0.01 mmol) of palladium(II) acetate, and 6.0 mg (0.02 mmol) of tri(o-tolyl)phosphine were put, and 20 mL of toluene, 5 mL of ethanol, and 20 mL of a potassium carbonate aqueous solution (2 mol/L) were added to this mixture. This mixture was deaerated while being stirred under low pressure. After the deaeration, the mixture was stirred under a nitrogen atmosphere at 90° C. for 4.5 hours to be reacted. After the reaction, 150 mL of toluene was added to this reaction mixture, and this suspension was filtrated through Florisil and then Celite. The obtained filtrate was washed with water, and magnesium sulfate was added thereto to remove moisture. This suspension was filtrated through Florisil, alumina, silica gel, and then Celite to obtain filtrate. The obtained filtrate was concentrated, methanol was added thereto, ultrasonic waves were applied thereto, and then recrystallization thereof was performed to obtain 6.4 g of an objective white solid at a yield of 86%. A synthetic scheme of Step 2 is shown in (c-4) given below.

(c-4)

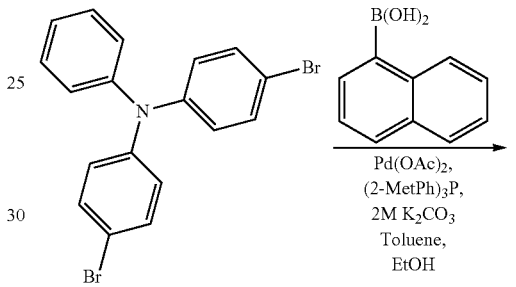

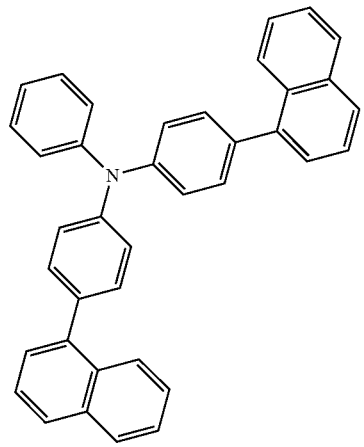

An Rf value of the objective substance by a silica gel thin layer chromatography (TLC) (developing solvent, ethyl acetate:hexane=1:10) was 0.53 and that of 4,4'-dibromotriphenylamine was 0.69.

The molecular weight of the white solid which was obtained in Step 2 was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 498.22 (mode is ES+) was detected and it was confirmed that objective αNBB1P was obtained.

Example 5

Synthetic Example 5

This example is a synthetic example of [4'-(1-naphthyl)biphenyl-4-yl]diphenylamine (abbreviation: αNTA1P), which is the triarylamine derivative described in Embodiment 1 as the structural formula (2). Hereinafter, the structure of αNTA1P is shown.

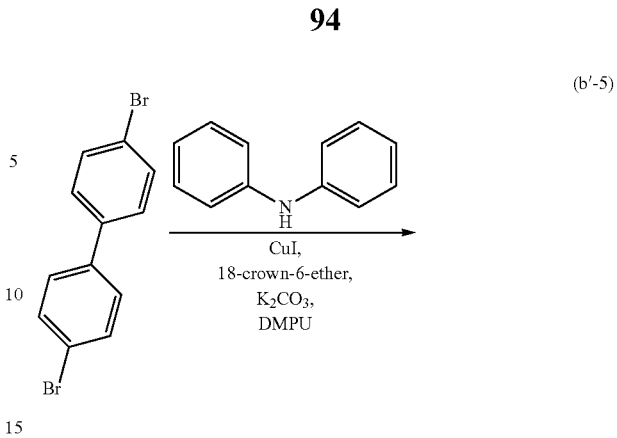

(b'-5)

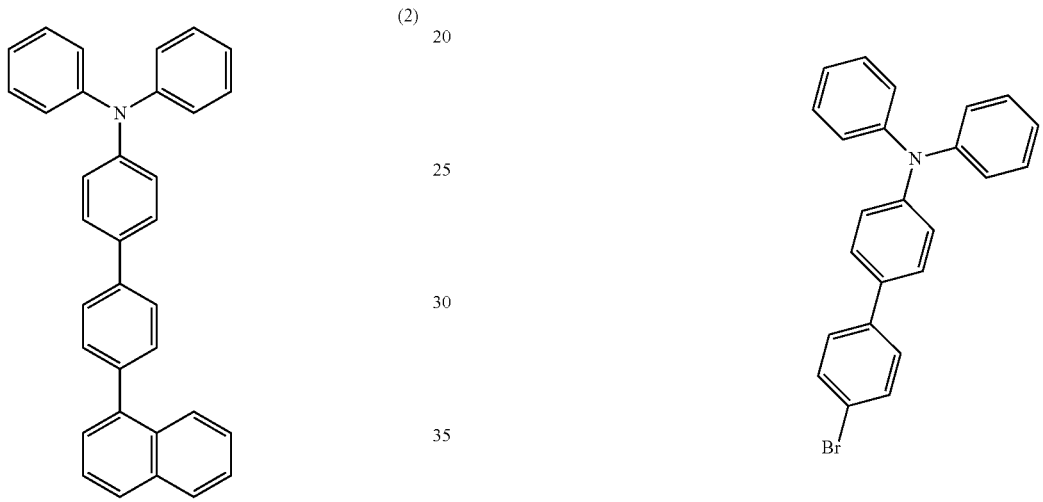

(2)

Step 1: Synthesis of 4-(4-bromophenyl)-triphenylamine

In a 500-mL three-neck flask, 22 g (70 mmol) of 4,4'-dibromobiphenyl, 8.5 g (50 mmol) of diphenylamine, 1.9 g (10 mmol) of copper(I) iodide, 2.6 g (10 mmol) of 18-crown-6-ether, 6.9 g (50 mmol) of potassium carbonate, and 50 mL of 1,3-dimethyl-3,4,5,6-tetrahydro-2(1H)-pyrimidinone (abbreviation: DMPU) were put, and the mixture was stirred under a nitrogen atmosphere at 180° C. for 37 hours to be reacted. After the reaction, 500 mL of toluene was added to this reaction mixture, and this suspension was filtrated through Florisil, silica gel, and then Celite. The obtained filtrate was washed with water, and magnesium sulfate was added thereto to remove moisture. This suspension was filtrated through Florisil, alumina, silica gel, and then Celite to obtain filtrate. The obtained filtrate was concentrated and purified by silica gel column chromatography (developing solvent, toluene:hexane=1:4). The obtained fraction was concentrated, hexane and methanol were added thereto, ultrasonic waves were applied thereto, and then recrystallization thereof was performed to obtain 5.3 g of an objective white powder at a yield of 27%. A synthetic scheme of Step 1 is shown in (b'-5) given below.

An Rf value of the objective substance by a silica gel thin layer chromatography (TLC) (developing solvent, ethyl acetate:hexane=1:10) was 0.5 and that of 4,4'-dibromobiphenyl was 0.59.

Step 2: Synthesis of [4'-(1-naphthyl)biphenyl-4-yl]diphenylamine (Abbreviation: αNTA1P In a 100-mL three-neck flask, 4.0 g (10 mmol) of 4-(4-bromophenyl)-triphenylamine which was synthesized in Step 1, 1.7 g (10 mmol) of 1-naphthaleneboronic acid, 11 mg (0.05 mmol) of palladium(II) acetate, and 15 mg (0.05 mmol) of tri(o-tolyl)phosphine were put, and 20 mL of toluene, 5 mL of ethanol, and 10 mL of a potassium carbonate aqueous solution (2 mol/L) were added to this mixture. This mixture was deaerated while being stirred under low pressure. After the deaeration, the mixture was stirred under a nitrogen atmosphere at 90° C. for 7 hours to be reacted. After the reaction, 150 mL of toluene was added to this reaction mixture, and this suspension was filtrated through silica gel, alumina, and then Celite. The obtained filtrate was washed with water, and magnesium sulfate was added thereto to remove moisture. This suspension was filtrated through silica gel, alumina, and then Celite to obtain filtrate. The obtained filtrate was concentrated, methanol was added thereto, ultrasonic waves were applied thereto, and then recrystallization thereof was performed to obtain 3.6 g of an objective white powder at a yield of 80%. A synthetic scheme of Step 2 is shown in (c-5) given below.

(c-5)

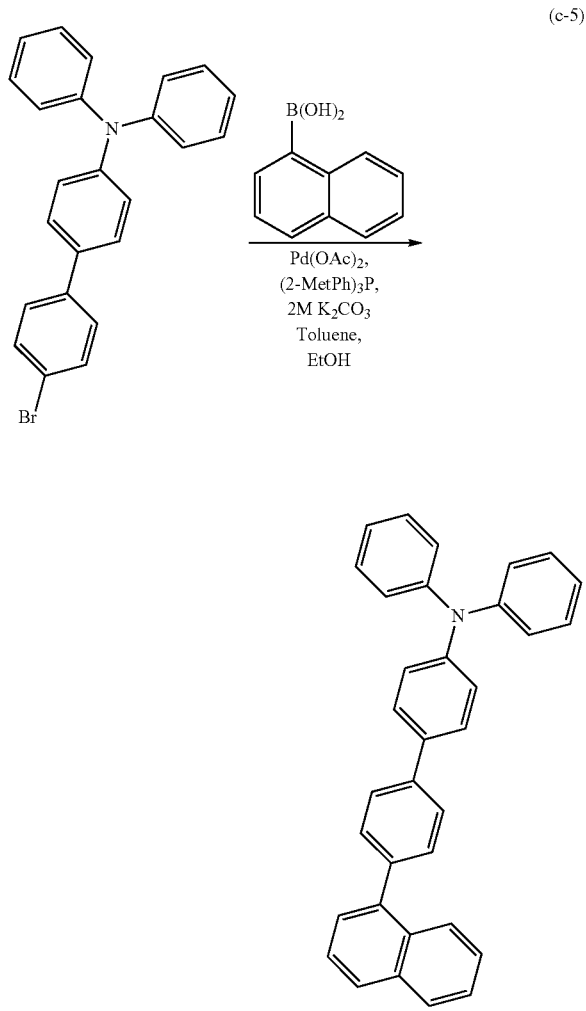

An Rf value of the objective substance by a silica gel thin layer chromatography (TLC) (developing solvent, ethyl acetate:hexane=1:10) was 0.58 and that of 1-(4'-bromobiphenyl-4-yl)naphthalene was 0.65.

The white solid which was obtained through Step 2 described above was measured by a nuclear magnetic resonance method ($^1$H NMR). The measurement data are shown below.

$^1$H NMR (CDCl$_3$, 300 MHz): δ (ppm)=7.05 (t, J=7.8 Hz, 2H), 7.12-7.58 (m, 18H), 7.70 (d, J=7.8 Hz, 2H), 7.87 (d, J=8.1 Hz, 1H), 7.92 (d, J=7.8 Hz, 1H), 7.99 (d, J=8.7 Hz, 1H)

The molecular weight of the above white solid was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 448.20 (mode is ES+) was detected.

From the above measurement results, it was understood that αNTA1P, which is the triarylamine derivative according to one embodiment of the present invention represented by the above structural formula (2), was obtained by this synthetic example.

Example 6

Synthetic Example 6

This example is a synthetic example of 4,4'-di-(2-naphthyl)triphenylamine (abbreviation: βNBB1P), which is the triarylamine derivative described in Embodiment 1 as the structural formula (19). Hereinafter, the structure of βNBB1P is shown.

(19)

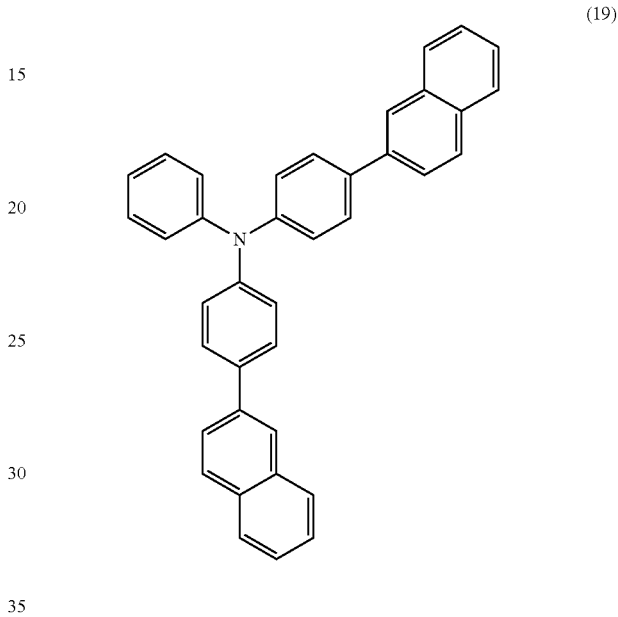

Step 1: Synthesis of 4,4'-dibromotriphenylamine

In a manner similar to that of Step 1 in Synthesis Example 4, the synthesis was performed.

Step 2: Synthesis of 4,4'-di-(2-naphthyl)triphenylamine (abbreviation: βNBB1P

In a 300-mL three-neck flask, 6.0 g (15 mmol) of 4,4'-dibromotriphenylamine which was synthesized in Step 1, 6.2 g (36 mmol) of 2-naphthaleneboronic acid, 16 mg (0.1 mmol) of palladium(II) acetate, and 21 mg (0.1 mmol) of tri(o-tolyl)phosphine were put and 50 mL of toluene, 20 mL of ethanol, and 20 mL of a potassium carbonate aqueous solution (2 mol/L) were added to this mixture. This mixture was deaerated while being stirred under low pressure. After the deaeration, the mixture was stirred under a nitrogen atmosphere at 90° C. for 4.5 hours to be reacted. After the reaction, 150 mL of toluene was added to this reaction mixture, and this suspension was filtrated through Florisil, silica gel, and then Celite. The obtained filtrate was washed with water, and magnesium sulfate was added thereto to remove moisture. This suspension was filtrated through Florisil, alumina, silica gel, and then Celite to obtain filtrate. The obtained filtrate was concentrated, hexane was added thereto, ultrasonic waves were applied thereto, and then recrystallization thereof was performed to obtain 5.6 g of an objective white powder at a yield of 75%. A synthetic scheme of Step 2 is shown in (c-6) given below.

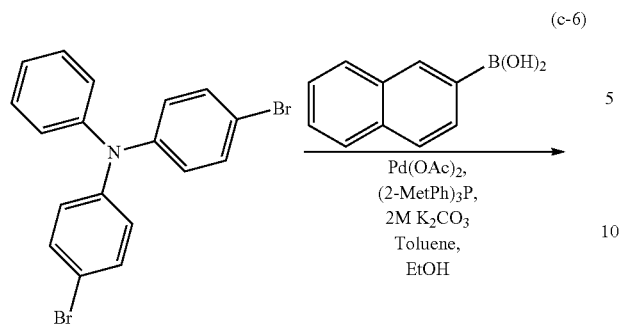

(c-6)

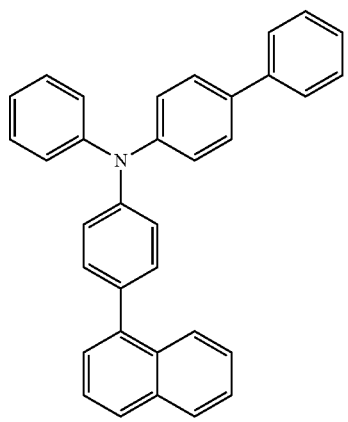

(3)

Step 1: Synthesis of 4-phenyl-diphenylame

In a 1000-mL three-neck flask, 51 g (220 mmol) of 4-bromobiphenyl, 23 g (250 mmol) of aniline, 50 g (500 mmol) of sodium tert-butoxide, and 250 mg (0.4 mmol) of bis(dibenzylideneacetone)palladium(0) were put, and the atmosphere in the flask was substituted by nitrogen. To this mixture, 500 mL of dehydrated toluene was added. This mixture was deaerated while being stirred under low pressure. After the deaeration, 3.0 mL (1.5 mmol) of tri(tert-butyl)phosphine (a 10 wt/hexane solution) was added thereto. Next, this mixture was stirred under a nitrogen atmosphere at 90° C. for 4.5 hours to be reacted. After the reaction, 600 mL of toluene was added to this reaction mixture, and this suspension was filtrated through Florisil and then Celite. The obtained filtrate was washed with water, and magnesium sulfate was added thereto to remove moisture. This suspension was filtrated through Florisil and then Celite to obtain filtrate. The obtained filtrate was concentrated, hexane was added thereto, ultrasonic waves were applied thereto, and then recrystallization thereof was performed to obtain 40 g of an objective white powder of 4-phenyl-diphenylamine at a yield of 73%. A synthetic scheme of Step 1 is shown in (α-7) given below.

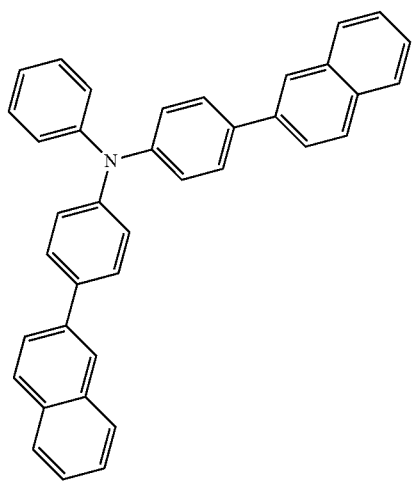

An Rf value of the objective substance by a silica gel thin layer chromatography (TLC) (developing solvent, ethyl acetate:hexane=1:10) was 0.53 and that of 4,4'-dibromotriphenylamine was 0.78.

The molecular weight of the white powder which was obtained in Step 2 was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 498.22 (mode is ES+) was detected and it was confirmed that objective βNBB1P was obtained.

Example 7

Synthetic Example 7

This example is a synthetic example of 4-(1-naphthyl)-4'-phenyltriphenylamine (abbreviation: αNBA1BP), which is the triarylamine derivative described in Embodiment 1 as the structural formula (3), in which a method different from that of Synthetic Example 1 is used. Hereinafter, the structure of αNBA1BP is shown.

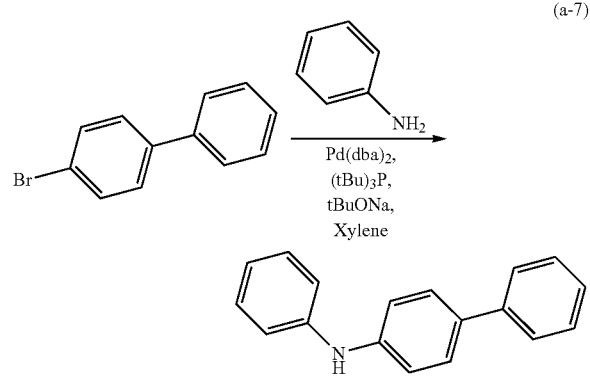

(a-7)

Step 2: Synthesis of 1-(4-bromophenyl)-naphthalene

In a 500-mL three-neck flask, 46 g (160 mmol) of 4-bromoiodobenzene, 24 g (140 mmol) of 1-naphthaleneboronic acid, 45 mg (0.2 mmol) of palladium(II) acetate, and 60 mg (0.2 mmol) of tri(o-tolyl)phosphine were put, and 100 mL of toluene, 20 mL of ethanol, and 11 mL of a potassium carbonate aqueous solution (2 mol/L) were added to this mixture. This mixture was deaerated while being stirred under low pressure. After the deaeration, the mixture was stirred under a nitrogen atmosphere at 90° C. for 4 hours to be reacted. After the reaction, 500 mL of toluene was added to this reaction mixture, and this suspension was filtrated through Florisil and then Celite. The obtained filtrate was washed with water, and magnesium sulfate was added thereto to remove moisture. This suspension was filtrated through Florisil and then Celite to obtain filtrate. The obtained filtrate was concentrated and purified by silica gel column chromatography (developing solvent, hexane). The obtained fraction was concentrated to obtain 25 g of an objective colorless transparent liquid at a yield of 62%. A synthetic scheme of Step 2 is shown in (b-7) given below.

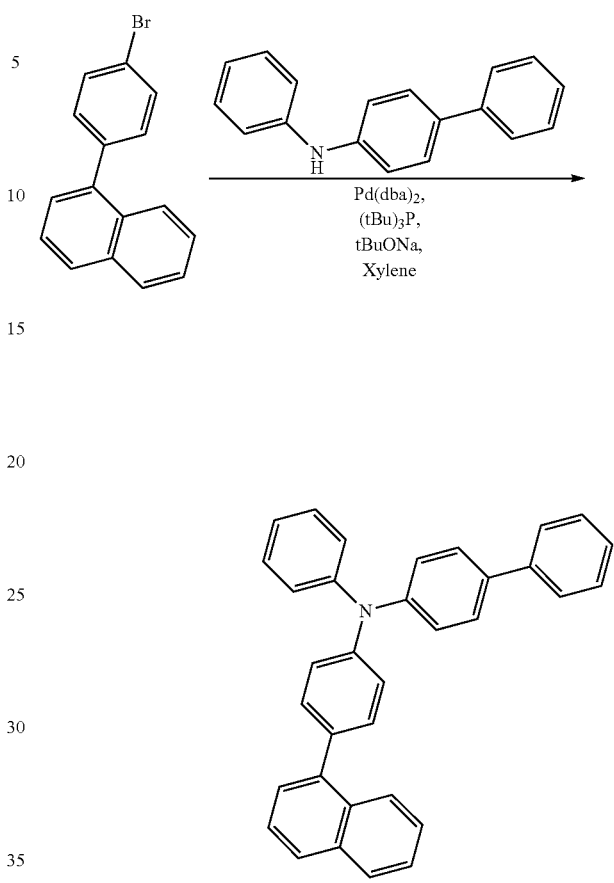

An Rf value of the objective substance by a silica gel thin layer chromatography (TLC) (developing solvent, hexane) was 0.38 and that of 4-bromoiodobenzene was 0.57.

Step 3: Synthesis of 4-(1-naphthyl)-4'-phenyltriphenylamine

In a 300-mL three-neck flask, 5.7 g (20 mmol) of 1-(4-bromophenyl)-naphthalene which was synthesized in Step 2, 4.9 g (20 mmol) of 4-phenyl-diphenylamine which was synthesized in Step 1, 2.5 g (25 mmol) of sodium tert-butoxide, and 11 mg (0.02 mmol) of bis(dibenzylideneacetone)palladium(0) were put, and the atmosphere of the flask was substituted by nitrogen. To this mixture, 50 mL of dehydrated xylene was added. This mixture was deaerated while being stirred under low pressure. After the deaeration, 0.1 mL (0.06 mmol) of tri(tert-butyl)phosphine (a 10 wt % hexane solution) was added thereto. This mixture was stirred under a nitrogen atmosphere at 110° C. for 6.5 hours to be reacted. After the reaction, 150 mL of toluene was added to this reaction mixture, and this suspension was filtrated through Florisil, silica gel, and then Celite. The obtained filtrate was washed with water, and magnesium sulfate was added thereto to remove moisture. This suspension was filtrated through Florisil, silica gel, and then Celite to obtain filtrate. The obtained filtrate was concentrated and purified by silica gel column chromatography (developing solvent, toluene:hexane=1:9). The obtained fraction was concentrated, acetone and hexane were added thereto, ultrasonic waves were applied thereto, and then recrystallization thereof was performed to obtain 7.3 g of an objective white powder at a yield of 98%. A synthetic scheme of Step 3 is shown in (c-7) given below.

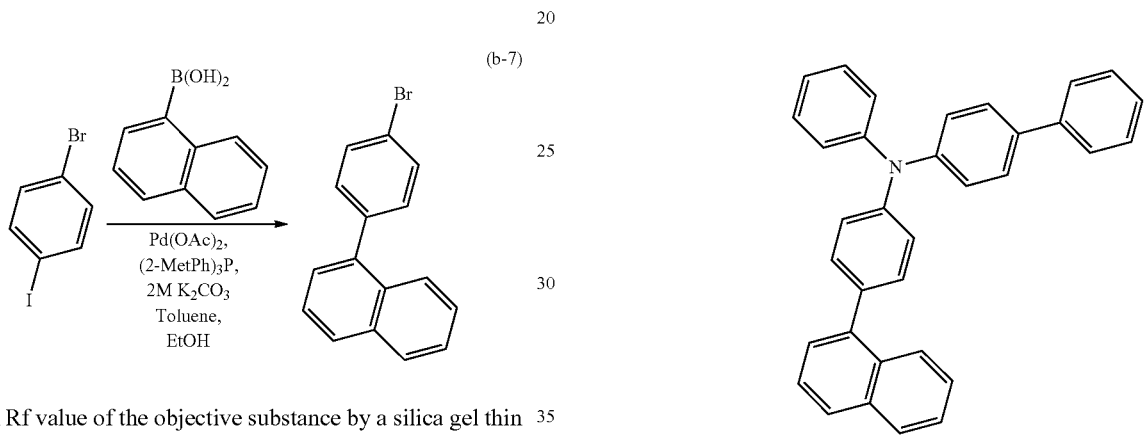

An Rf value of the objective substance by a silica gel thin layer chromatography (TLC) (developing solvent, ethyl acetate:hexane=1:10) was 0.31, that of 1-(4-bromophenyl)-naphthalene was 0.60, and that of 4-phenyl-diphenylamine was 0.16.

The molecular weight of the white powder obtained in Step 3 was measured by a TOF-MS detector (Waters Micromass LCT Premier, manufactured by Waters). A mixture solution containing acetonitrile and 0.1% of a formic acid solution (mixture rate of acetonitrile and the formic acid solution, 80/20 vol/vol) was used as a solvent. Accordingly, a main peak with a molecular weight of 448.21 (mode is ES+) was detected. From the above measurement results, it was understood that αNBA1BP, which is the triarylamine derivative represented by the above structural formula (3), was obtained by this synthetic example.

Example 8

Synthetic Example 8

This example is a synthetic example of 4,4'-di-(1-naphthyl)triphenylamine (abbreviation: αNBB1P), which is the triarylamine derivative described in Embodiment 1 as the structural formula (7), in which a method different from that of Synthetic Example 4 is used. Hereinafter, the structure of αNBB1P is shown.

101

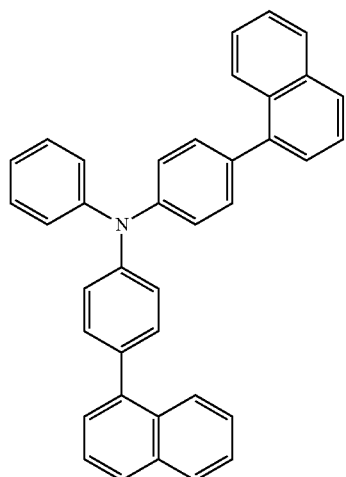

(7)

Step 1: Synthesis of 1-(4-bromophenyl)-naphthalene

In a manner similar to that of Step 2 in Synthetic Example 7, the synthesis was performed.

Step 2: Synthesis of 4,4'-di-(1-naphthyl)triphenylamine (abbreviation: αNBB1P In a 100-mL three-neck flask, 3.4 g (12 mmol) of 1-(4-bromophenyl)-naphthalene which was synthesized in Step 1, 0.5 g (5 mmol) of aniline, 1.5 g (15 mmol) of sodium tert-butoxide, 10 mg (0.05 mmol) of palladium(II) acetate, 10 mg (0.05 mmol) of 1,1-bis(diphenylphosphino)ferrocene (abbreviation: DPPF), and 15 mL of toluene were put. This mixture was deaerated while being stirred under low pressure. After the deaeration, the mixture was stirred under a nitrogen atmosphere at 80° C. for 5 hours to be reacted. After the reaction, 150 mL of toluene was added to this reaction mixture, and this suspension was filtrated through Florisil and then Celite. The obtained filtrate was concentrated and purified by silica gel column chromatography (developing solvent, toluene:hexane=1:4). The obtained fraction was concentrated, methanol was added thereto, ultrasonic waves were applied thereto, and then recrystallization thereof was performed to obtain 1.9 g of an objective white powder at a yield of 77%. A synthetic scheme of Step 2 is shown in (c-8) given below.

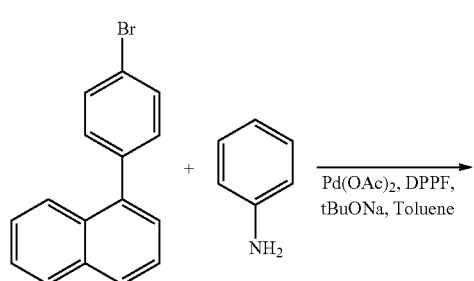

(c-8)

102

-continued

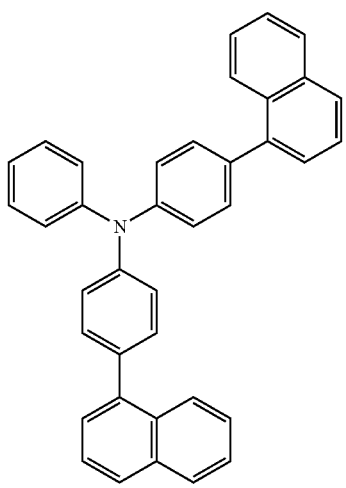

An Rf value of the objective substance by a silica gel thin layer chromatography (TLC) (developing solvent, ethyl acetate:hexane=1:10) was 0.22 and that of 1-bromo-4-(1-naphthyl)benzene was 0.53.

Example 9

In this example, two light-emitting elements (a light-emitting element 2 and a light-emitting element 3) using the triarylamine derivative described in Embodiment 1 as a material that forms a hole transporting layer adjacent to a light-emitting layer emitting blue fluorescence were manufactured, and a performance test for the light-emitting elements was also carried out. Note that in this example, light-emitting elements (a light-emitting element 1 and a light-emitting element 4) without using the above triarylamine derivative were also manufactured for comparison, and a performance test for the light-emitting elements was also carried out.

In addition, a molecular structure of an organic compound (αNBA1BP, description of which is omitted because the structure thereof is shown in Example 1 and Example 2) which is used in this example is shown in structural formulae (i) to (vi) given below. In FIG. 1A, the element structure in which an electron injecting layer is provided between the electron transporting layer 114 and the second electrode 104 was employed.

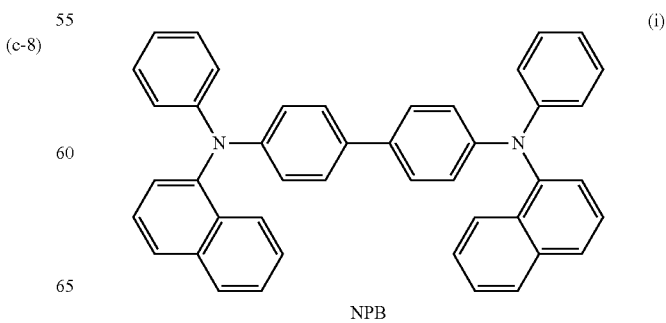

(i)

NPB

-continued (ii)

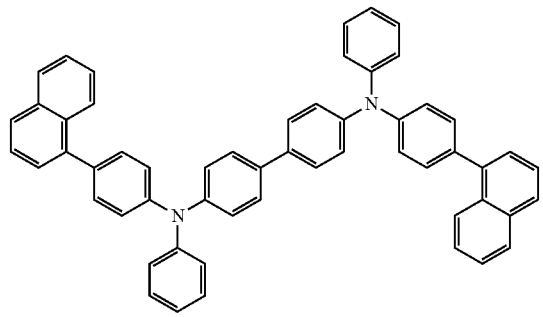

αNBABP (iii)

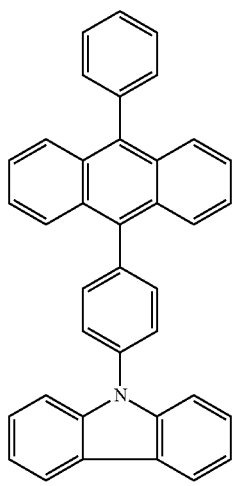

CzPA (iv)

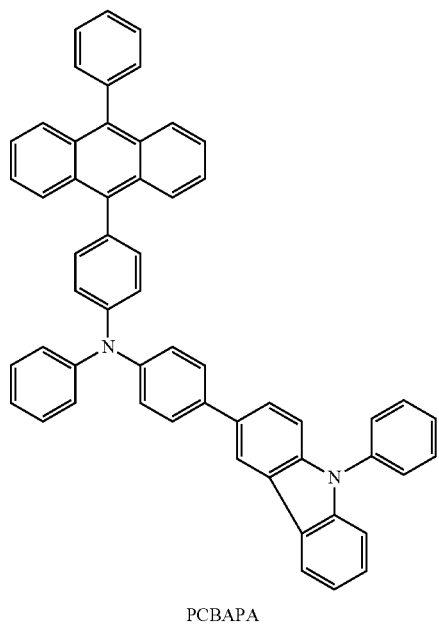

PCBAPA

-continued (v)

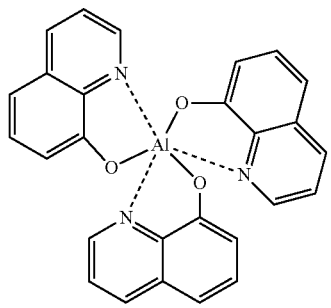

Alq (vi)

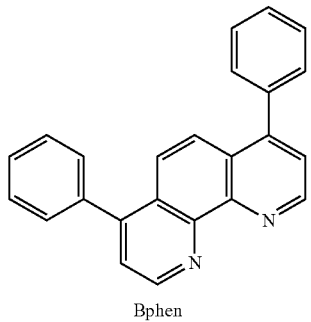

Bphen

<<Manufacture of Light-Emitting Elements 1 to 4>>

First, a glass substrate 101 over which indium tin oxide containing silicon (ITSO) with a thickness of 110 nm had been formed as a first electrode 102 was prepared. The periphery of surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate 101 was fixed to a holder provided in the vacuum evaporation apparatus such that the surface of the substrate 101 provided with ITSO is faced downward.

After the pressure in the vacuum evaporation apparatus was reduced to 104 Pa, 4,4'-bis[N-(1-naphthyl)-N-phenylamino]biphenyl (abbreviation: NPB) represented by the above structure formula (i) and molybdenum(VI) oxide were co-evaporated to have a mass ratio of NPB:molybdenum (VI) oxide=4:1, whereby a hole injecting layer 111 was formed. The thickness of the hole injecting layer 111 was 50 nm. Note that the co-evaporation is an evaporation method in which some different substances are evaporated from some different evaporation sources at the same time.

Subsequently, a hole transporting layer 112 was formed in such a manner that the light-emitting elements 1 to 4 were each evaporated to have a thickness of 10 nm using, for the light-emitting element 1, NPB which is widely used as a material for a hole transporting layer, for the light-emitting element 2, αNBA1BP which is the triarylamine derivative described in Embodiment 1; for the light-emitting element 3, αNBB1BP which is the triarylamine derivative described in Embodiment 1; and for the light-emitting element 4, 4-(1- naphthyl)-4'-phenyltriphenylamine (abbreviation: αNBABP) which is the known substance represented by the above structural formula (ii).

Further, a light-emitting layer 113 was formed over the hole-transporting layer 112 in such a manner that 9-[4-(10-phenyl-9-anthryl)phenyl]-9H-carbazole (abbreviation: CzPA) represented by the above structure formula (iii) and 4-(10-phenyl-9-anthryl)-4'-(9-phenyl-9H-carbazol-3-yl)triphenylamine (abbreviation: PCBAPA) represented by the above structure formula (iv) were co-evaporated to have a mass ratio of CzPA:PCBAPA=1:0.1. The thickness of the light-emitting layer 113 was 30 nm.

Then, an electron transporting layer 114 was formed by evaporating tris(8-quinolinolato)aluminum(III) (abbreviation: Alq) represented by the above structural formula (v) with a thickness of 10 nm and, over Alq, bathophenanthroline (abbreviation: BPhen) represented by the above structural formula (vi) with a thickness of 20 nm. Further, lithium fluoride was evaporated to a thickness of 1 nm over the electron transporting layer 114, whereby an electron injecting layer was formed. Lastly, aluminum was formed with a thickness of 200 nm as a second electrode 104 which serves as a cathode, whereby the light-emitting elements 1 to 4 were completed. Note that in the above evaporation process, evaporation was all performed by a resistance heating method.

<<Operating characteristics of Light-Emitting Elements 1 to 4>>

The light-emitting elements 1 to 4 thus obtained were sealed in a glove box under a nitrogen atmosphere without being exposed to atmospheric air. Then, the operating characteristics of the light-emitting elements were measured. Note that the measurement was carried out at a room temperature (in the atmosphere kept at 25° C.).

Figure 15:
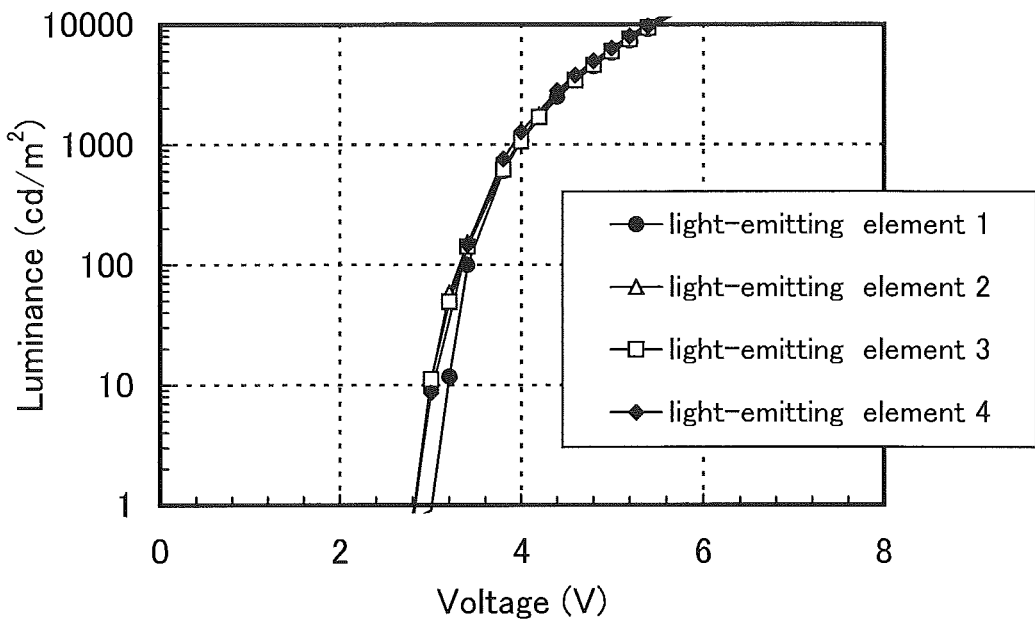
FIG. 15 is a graph of voltage vs. luminance characteristics of the light-emitting elements manufactured in Example 9.
Figure 16:
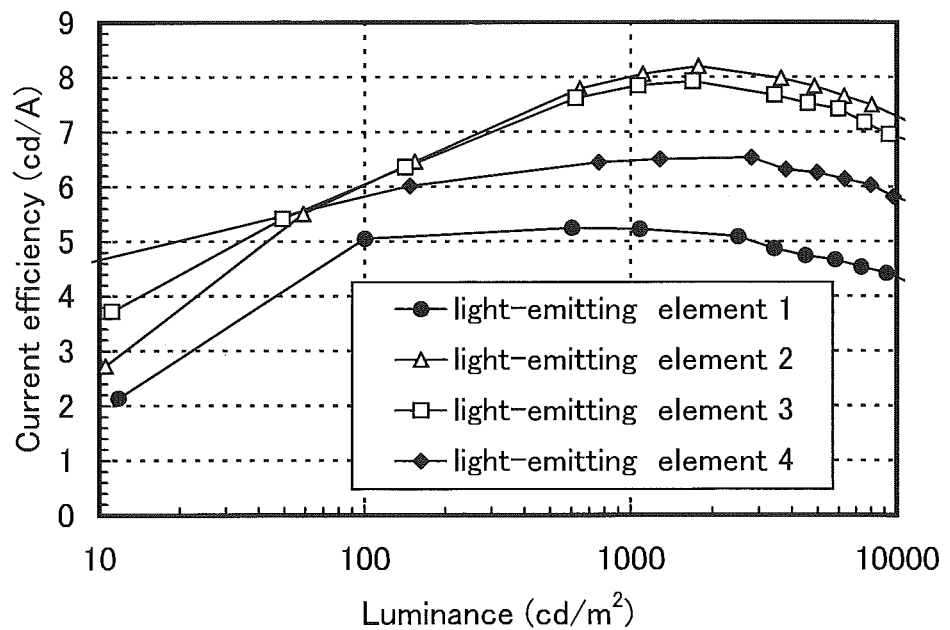
FIG. 16 is a graph of luminance vs. current efficiency characteristics of the light-emitting elements manufactured in Example 9.
Figure 17:
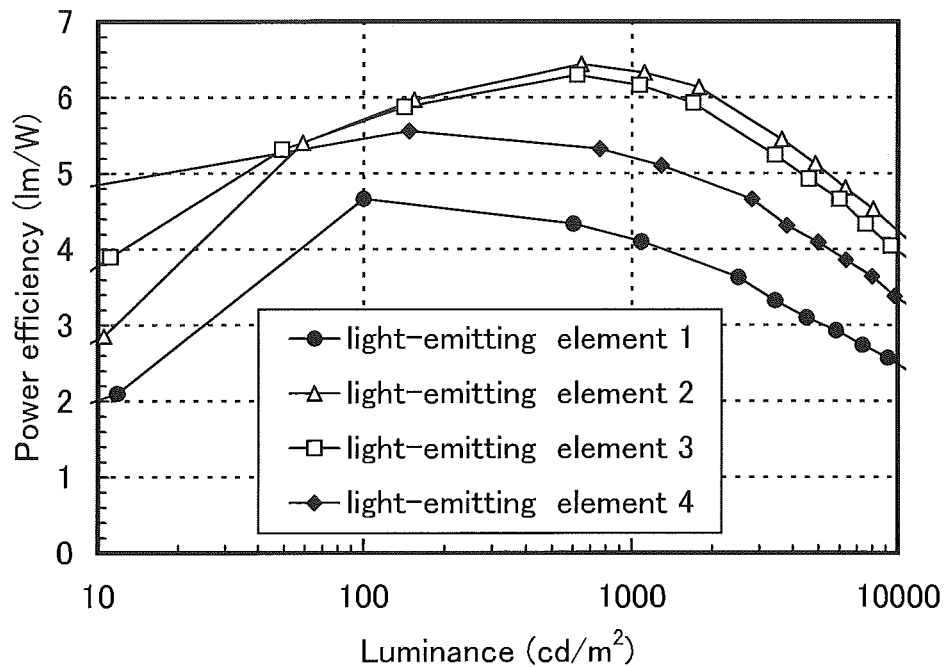
FIG. 17 is a graph of luminance vs. power efficiency characteristics of the light-emitting elements manufactured in Example 9.

Voltage vs. luminance characteristics of each light-emitting element are shown in FIG. 15, luminance vs. current efficiency characteristics of each light-emitting element are shown in FIG. 16, and luminance vs. power efficiency characteristics of each light-emitting element are shown in FIG. 17. In FIG. 15, a longitudinal axis represents a luminance ($cd/m^2$), and a horizontal axis represents a voltage (V). In FIG. 16, a longitudinal axis represents a current efficiency (cd/A), and a horizontal axis represents a luminance ($cd/m^2$). In FIG. 17, a longitudinal axis represents a power efficiency (lm/W), and a horizontal axis represents a luminance ($cd/m^2$).

It is understood from the graphs that the light-emitting element 2 and the light-emitting element 3 using the triarylamine derivative described in Embodiment 1 as a hole transporting layer show luminance vs. current efficiency characteristics which are preferable to those of the light-emitting element 1 and the light-emitting element 4, and have preferable luminous efficiency. In addition, as for the power efficiency (lm/W) of each light-emitting element at a luminance of 1000 $cd/m^2$, the light-emitting element 1 was 4.1, the light-emitting element 2 was 6.3, the light-emitting element 3 was 6.2, and the light-emitting element 4 was 5.3. Accordingly, it was understood that, as compared to the light-emitting element 1 and the light-emitting element 4, the light-emitting element 2 and the light-emitting element 3 can perform driving with low power consumption, which is preferable.

Figure 18:
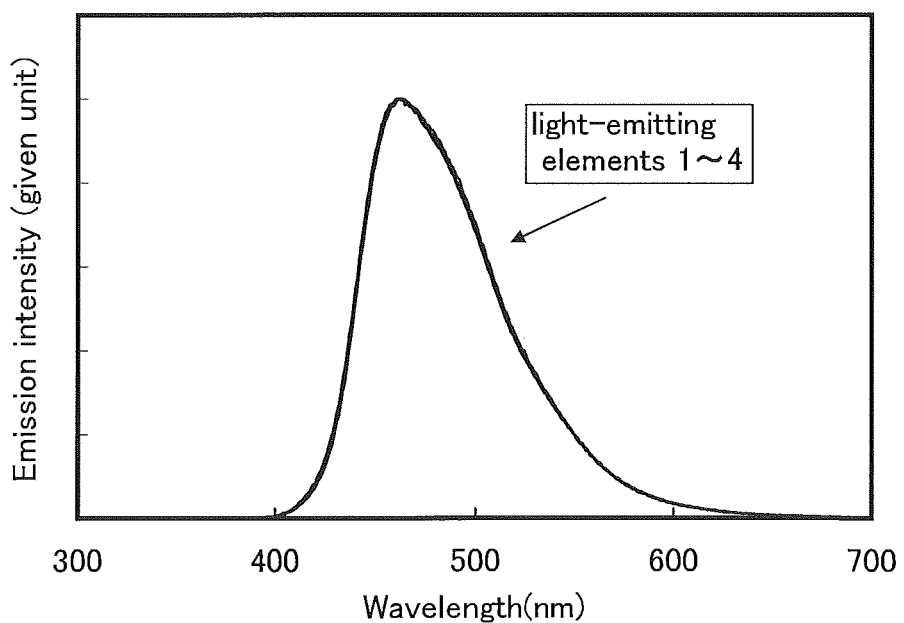
FIG. 18 is a graph of emission spectra of the light-emitting elements manufactured in Example 9.

FIG. 18 shows emission spectra when a current of 1 mA was made to flow in the manufactured light-emitting elements 1 to 4. In FIG. 18, a horizontal axis represents an emission wavelength (nm), and a longitudinal axis represents an emission intensity. FIG. 18 shows a comparative value of each light-emitting element with the same maximum emission intensity. It is understood from FIG. 18 that each of the light-emitting elements 1 to 4 emits preferable blue light which is resulted from PCBAPA which is a light-emitting substance.

Next, when these elements were driven under the condition of fixed current density with an initial luminance set at 1000 $cd/m^2$, each of the light-emitting elements similarly showed preferable characteristics in the luminance half-decay period.

Example 10

In this example, a light-emitting element (a light-emitting element 7) using the triarylamine derivative described in Embodiment 1 as a material that forms a hole transporting layer adjacent to a light-emitting layer emitting green phosphorescence was manufactured, and a performance test for the light-emitting element was also carried out. Note that in this example, light-emitting elements (a light-emitting element 5 and a light-emitting element 6) without using the above triarylamine derivative were also manufactured for comparison, and a performance test for the light-emitting elements was also carried out.

A molecular structure of an organic compound (description is omitted for those already have shown) which is used in this example is shown in structural formulae (vii) and (viii) given below. In FIG. 1A, the element structure in which an electron injecting layer is provided between the electron transporting layer 114 and the second electrode 104 was employed.

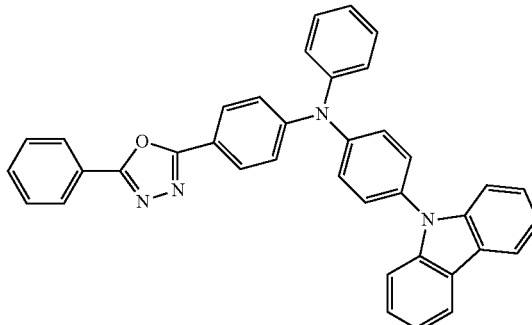

(vii)

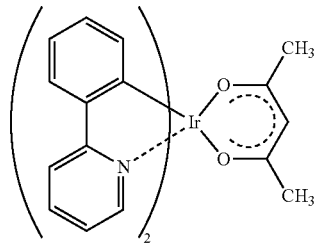

(viii)

<<Manufacture of Light-Emitting Elements 5 to 7>>

First, a glass substrate 101 over which indium tin oxide containing silicon (ITSO) with a thickness of 110 nm had been formed as a first electrode 102 was prepared. The periphery of surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about $10^{-4}$ Pa, vacuum baking at 170° C. for 30 minutes was performed in a heating chamber of the vacuum evaporation apparatus, and then the substrate was cooled down for about 30 minutes.

Next, the substrate 101 was fixed to a holder provided in the vacuum evaporation apparatus such that the surface of the substrate 101 provided with ITSO is faced downward.

After the pressure in the vacuum evaporation apparatus was reduced to 104 Pa, 4,4'-bis[N-(1-naphthyl)-N-phenylamino]biphenyl (abbreviation: NPB) represented by the above structure formula (i) and molybdenum(VI) oxide were co-evaporated to have a mass ratio of NPB:molybdenum (VI) oxide=4:1, whereby a hole injecting layer 111 was formed. The thickness of the hole injecting layer 111 was 40 nm. Note that the co-evaporation is an evaporation method in which some different substances are evaporated from some different evaporation sources at the same time.

Subsequently, a hole transporting layer 112 was formed in such a manner that the light-emitting elements 5 to 7 were each evaporated to have a thickness of 20 nm using, for the light-emitting element 5, NPB which is widely used as a material for a hole transporting layer, for the light-emitting element 6, αNBABP the structure of which is shown in Example 6 as the structural formula (ii); and for the light-emitting element 7, αNBA1BP which is the triarylamine derivative according to one embodiment of the present invention described in Embodiment 1.

Further, a light-emitting layer 113 was formed over the hole-transporting layer 112 in such a manner that 4-(9H-carbazol-9-yl)-4'-(5-phenyl-1,3,4-oxadiazol-2-yl)triphenylamine (abbreviation: YGAO11) represented by the above structure formula (vii) and bis[2-phenylpyridinato-N, $C^{2'}$]iridium(MI) acetylacetonate (abbreviation: Ir(ppy)$_2$acac) represented by the above structure formula (viii) were co-evaporated to have a mass ratio of YGAO11: Ir(ppy)$_2$acac=1:0.05. The thickness of the light-emitting layer 113 was 40 nm.

Then, an electron transporting layer 114 was formed by evaporating bathophenanthroline (abbreviation: BPhen) represented by the above structural formula (vi) with a thickness of 30 nm. Further, lithium fluoride was evaporated to a thickness of 1 nm over the electron transporting layer 114, whereby an electron injecting layer was formed. Lastly, aluminum was formed with a thickness of 200 nm as the second electrode 104 which serves as a cathode, whereby the light-emitting elements 5 to 7 were completed. Note that in the above evaporation process, evaporation was all performed by a resistance heating method.

<<Operating characteristics of Light-Emitting Elements 5 to 7>>

The light-emitting elements 5 to 7 thus obtained were sealed in a glove box under a nitrogen atmosphere without being exposed to atmospheric air. Then, the operating characteristics of the light-emitting elements were measured. Note that the measurement was carried out at a room temperature (in the atmosphere kept at 25° C.).

Figure 19:
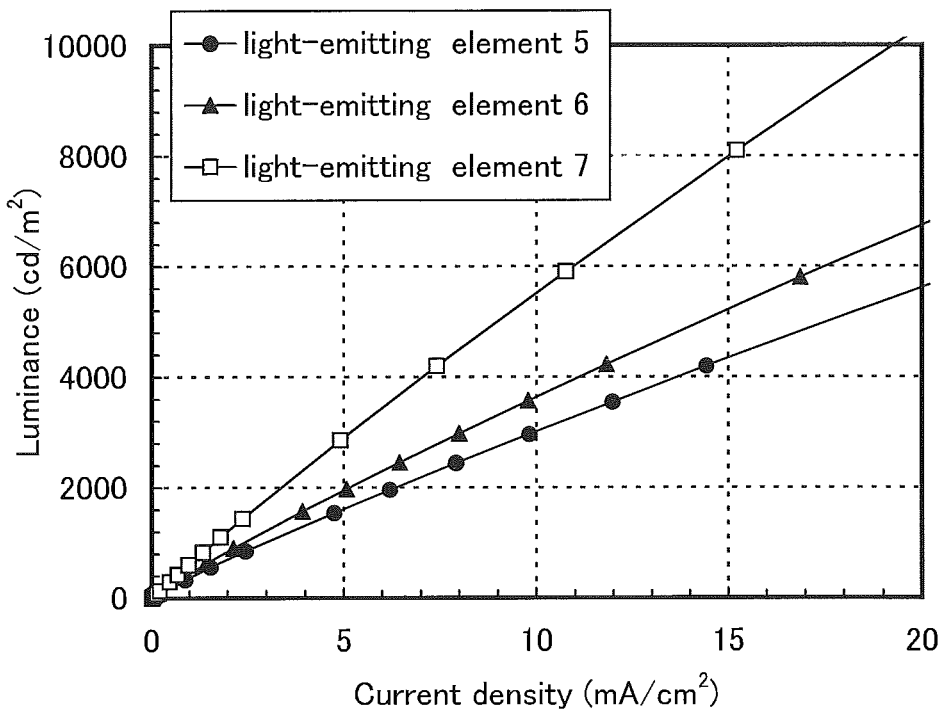
FIG. 19 is a graph of current density vs. luminance characteristics of the light-emitting elements manufactured in Example 10.
Figure 20:
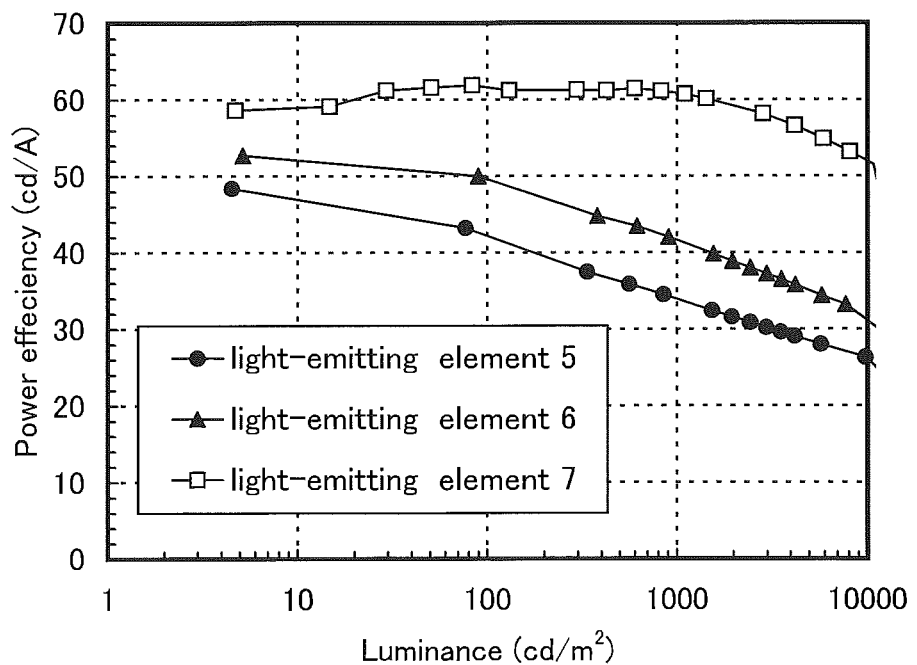
FIG. 20 is a graph of luminance vs. current efficiency characteristics of the light-emitting elements manufactured in Example 10.
Figure 21:
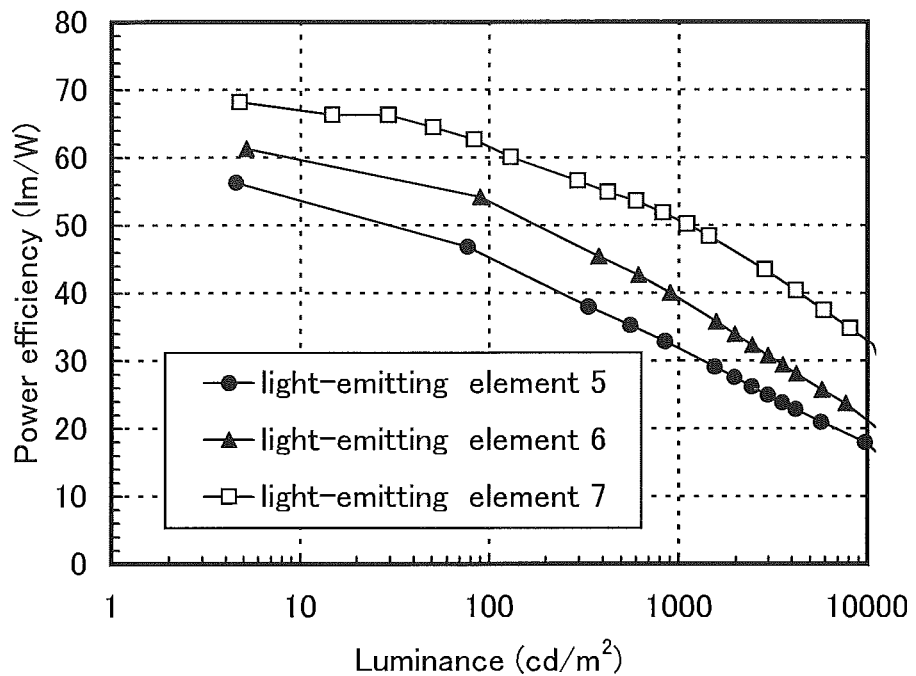
FIG. 21 is a graph of luminance vs. power efficiency characteristics of the light-emitting elements manufactured in Example 10.
Figure 22:
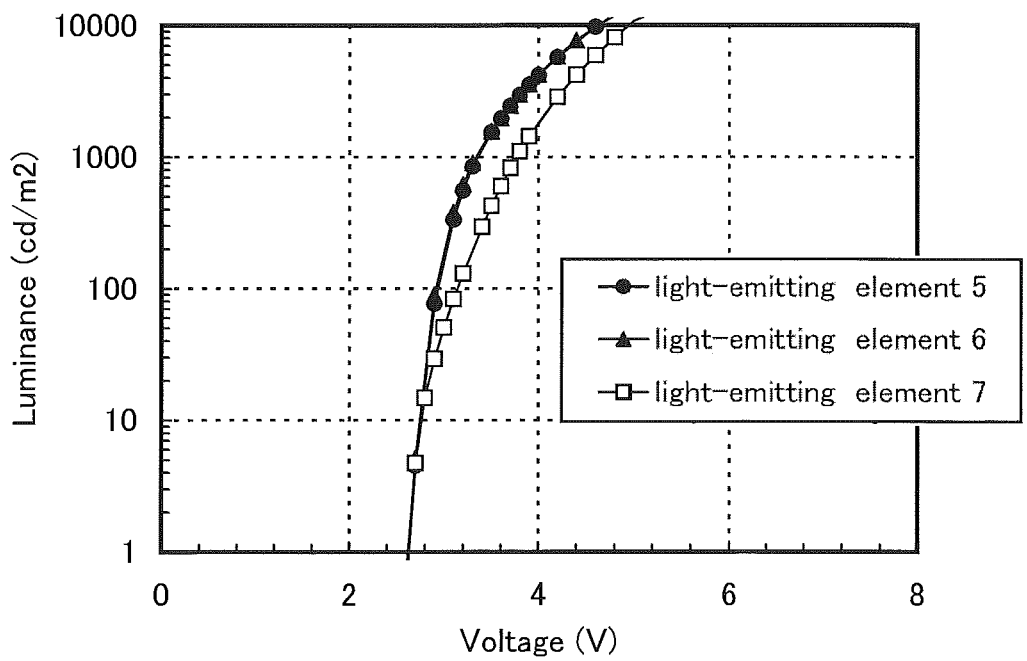
FIG. 22 is a graph of voltage vs. luminance characteristics of the light-emitting elements manufactured in Example 10.

Current density vs. luminance characteristics of each light-emitting element are shown in FIG. 19, luminance vs. current efficiency characteristics of each light-emitting element are shown in FIG. 20, luminance vs. power efficiency characteristics of each light-emitting element are shown in FIG. 21, and voltage vs. luminance characteristics of each light-emitting element are shown in FIG. 22. In FIG. 19, a longitudinal axis represents a luminance (cd/m$^2$), and a horizontal axis represents a current density (mA/cm$^2$). In FIG. 20, a longitudinal axis represents a current efficiency (cd/A), and a horizontal axis represents a luminance (cd/m$^2$). In FIG. 21, a longitudinal axis represents a power efficiency (lm/W), and a horizontal axis represents a luminance (cd/m$^2$). In FIG. 22, a longitudinal axis represents a luminance (cd/m$^2$), and a horizontal axis represents a voltage (V).

It is understood from the graphs that the light-emitting element 7 using the triarylamine derivative described in Embodiment 1 as a hole transporting layer show luminance vs. current efficiency characteristics which are preferable to those of the light-emitting element 5 and the light-emitting element 6, and have preferable luminous efficiency. In addition, as for the power efficiency (lm/W) of each light-emitting element at a luminance of 1000 cd/m$^2$, the light-emitting element 5 was 33, the light-emitting element 6 was 40, and the light-emitting element 7 was 50. Accordingly, it was understood that, as compared to the light-emitting element 5 and the light-emitting element 6, the light-emitting element 7 can perform driving with low power consumption, which is preferable.

In addition, a CIE chromaticity coordinate of each of the light-emitting elements 5 to 7 at a luminance of 1000 cd/m$^2$ was (x=0.35, y=0.62), and green light emission which is derived from Ir(ppy)$_2$acac was exhibited.

From the above results, since the triarylamine derivative described in Embodiment 1 shows high luminous efficiency even when it is used for a hole transporting layer adjacent to a light-emitting layer emitting green phosphoresce, it is understood that the above triarylamine derivative is a substance having high triplet energy.

Example 11

In this example, four light-emitting elements (a light-emitting element 9, a light-emitting element 10, a light-emitting element 11, and a light-emitting element 12) using a composite material in which an acceptor substance is contained in the triarylamine derivative described in Embodiment 1 as a material that forms a hole injecting layer were manufactured, and a performance test for the light-emitting elements were also carried out. Note that in this example, a light-emitting element (a light-emitting element 8) without using the above triarylamine derivative was also manufactured for comparison, and a performance test for the light-emitting element was also carried out.

Note that since the organic compounds used in this example are already all described in this specification, description of a molecular structure thereof is omitted. In FIG. 1A, the element structure in which an electron injecting layer is provided between the electron transporting layer 114 and the second electrode 104 with the light-emitting layer 113 having a two-layer structure was employed.

<<Manufacture of Light-Emitting Elements 8 to 12>>

First, a glass substrate 101 over which indium tin oxide containing silicon (ITSO) with a thickness of 110 am had been formed as a first electrode 102 was prepared. The periphery of surface of the ITSO was covered with a polyimide film so that an area of 2 mm×2 mm of the surface was exposed. The electrode area was 2 mm×2 mm. As a pretreatment for forming the light-emitting element over the substrate, the surface of the substrate was washed with water and baked at 200° C. for one hour, and then a UV ozone treatment was performed for 370 seconds. Then, the substrate was transferred into a vacuum evaporation apparatus whose pressure was reduced to about 104 Pa, vacuum baking at 170° C. for 30 minutes was performed in a heating chamber of the vacuum evaporation apparatus, and then the substrate was cooled down for about 30 minutes.

Next, the substrate 101 was fixed to a holder provided in the vacuum evaporation apparatus such that the surface of the substrate 101 provided with ITSO is faced downward.

After the pressure in the vacuum evaporation apparatus was reduced to 104 Pa, in the light-emitting element 8 which is the comparative element, NPB and molybdenum(VI) oxide were co-evaporated to have a mass ratio of NPB molybdenum(VI) oxide=4:1, whereby a hole injecting layer 111 was formed. In addition, in the light-emitting elements 9 to 12 which are each an example of a light-emitting element according to one embodiment of the present invention, αNBA1BP, which is the triarylamine derivative described in Embodiment 1, is used instead of NPB to be co-evaporated with molybdenum(VI) oxide, whereby the hole injecting layer 111 was formed. Note that the evaporation was performed so that the mass ratio of αNBA1BP and molybdenum(VI) oxide in the light-emitting element 9 was 8:1; the mass ratio in the light-emitting element 10 was 4:1; and the mass ratio in the light-emitting elements 11 and 12 was 2:1. Each of the hole injecting layers had a thickness of 50 nm. Note that the co-evaporation is an evaporation method in which some different substances are evaporated from some different evaporation sources at the same time.

Subsequently, a hole transporting layer 112 was formed in such a manner that the light-emitting elements 8 to 12 are each evaporated to have a thickness of 10 nm using, for the light-emitting elements 8 to 11, NPB which is widely used as a material for a hole transporting layer, and for the light-emitting element 12, αNBA1BP which is the triarylamine derivative described in Embodiment 1.

Further, a light-emitting layer 113 was formed over the hole-transporting layer 112 in such a manner that PCBAPA was evaporated with a thickness of 25 nm and then CzPA and PCBAPA were co-evaporated with a thickness of 30 nm to have a mass ratio of CzPA:PCBAPA=10:1.

Then, an electron-transporting layer 114 was formed by evaporating Alq with a thickness of 10 nm and BPhen over the film of Alq with a thickness of 20 nm. Further, lithium fluoride was evaporated to a thickness of 1 nm over the electron transporting layer 114, whereby an electron injecting layer was formed. Lastly, aluminum was formed with a thickness of 200 nm as the second electrode 104 which serves as a cathode, whereby the light-emitting elements 8 to 12 were completed. Note that in the above evaporation process, evaporation was all performed by a resistance heating method.

<<Operating Characteristics of Light-Emitting Elements 8 to 12>>

The light-emitting elements 8 to 12 thus obtained were sealed in a glove box under a nitrogen atmosphere without being exposed to atmospheric air. Then, the operating characteristics of the light-emitting elements were measured. Note that the measurement was carried out at a room temperature (in the atmosphere kept at 25° C.).

Figure 23:
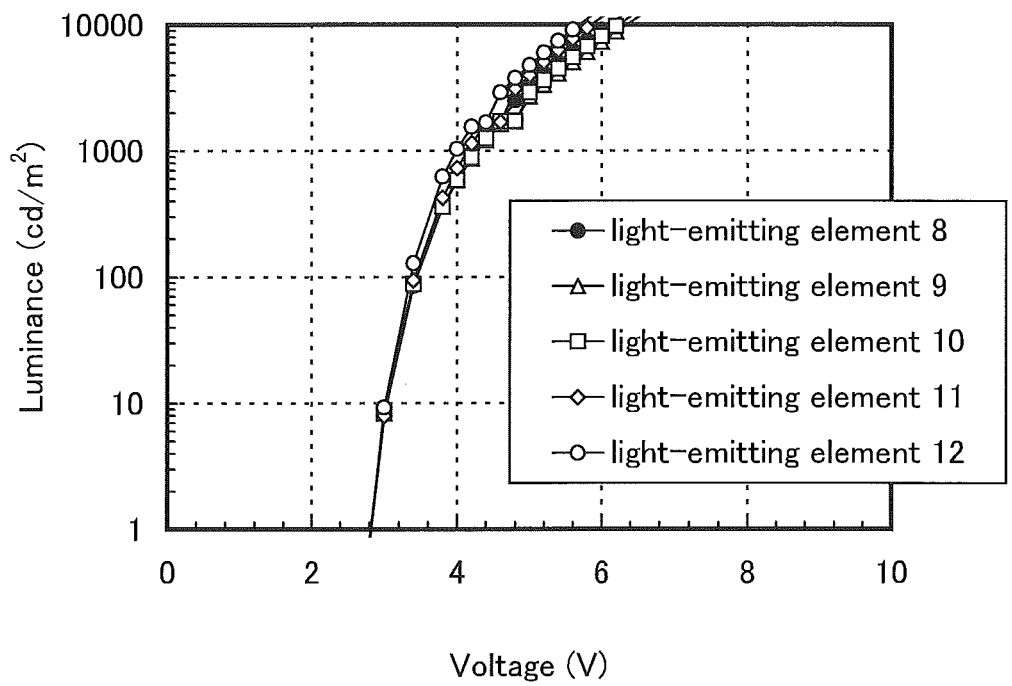
FIG. 23 is a graph of voltage vs. luminance characteristics of the light-emitting elements manufactured in Example 11.
Figure 24:
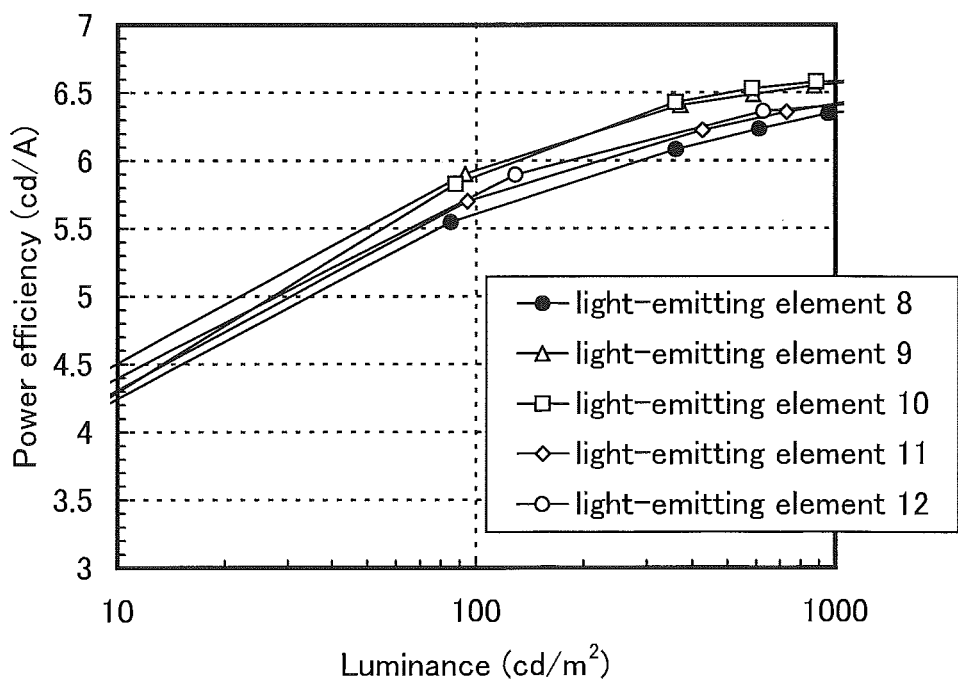
FIG. 24 is a graph of luminance vs. current efficiency characteristics of the light-emitting elements manufactured in Example 11.
Figure 25:
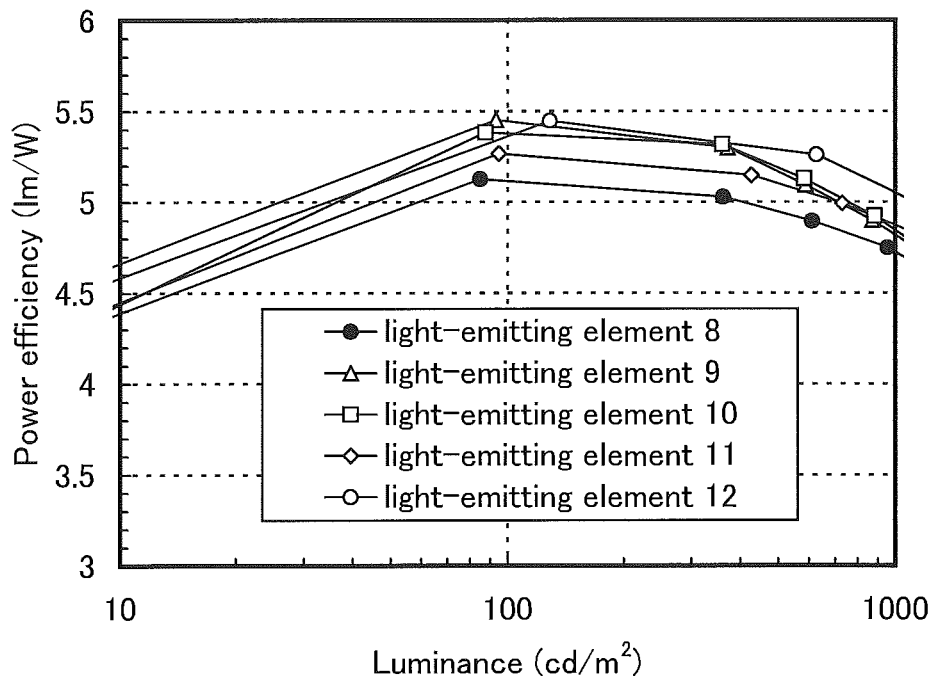
FIG. 25 is a graph of luminance vs. power efficiency characteristics of the light-emitting elements manufactured in Example 11.

Voltage vs. luminance characteristics of each light-emitting element are shown in FIG. 23, luminance vs. current efficiency characteristics of each light-emitting element are shown in FIG. 24, and luminance vs. power efficiency characteristics of each light-emitting element are shown in FIG. 25. In FIG. 23, a longitudinal axis represents a luminance ($cd/m^2$), and a horizontal axis represents a voltage (V). In FIG. 24, a longitudinal axis represents a current efficiency (cd/A), and a horizontal axis represents a luminance ($cd/m^2$). In FIG. 25, a longitudinal axis represents a power efficiency (lm/W), and a horizontal axis represents a luminance ($cd/m^2$).

It was understood from FIG. 24 that the light-emitting elements 9 to 12 using the triarylamine derivative, which is described in Embodiment 1, together with the acceptor substance as a composite material for a hole injecting layer show luminance vs. current efficiency characteristics which are preferable to those of the light-emitting element 8 using NPB instead of the triarylamine derivative, which is described in Embodiment 1, and have preferable luminous efficiency. In addition, it is understood from FIG. 25 that, as for the power efficiency (lm/W) of each light-emitting element at a luminance of 1000 $cd/m^2$, the light-emitting element 8 was 4.7, the light-emitting element 9 was 4.9, the light-emitting element 10 was 4.9, the light-emitting element 11 was 4.8, and the light-emitting element 12 was 5.0. Accordingly, it was understood that, as compared to the light-emitting element 8, the light-emitting elements 9 to 12 can perform driving with low power consumption, which is preferable.

Figure 26:
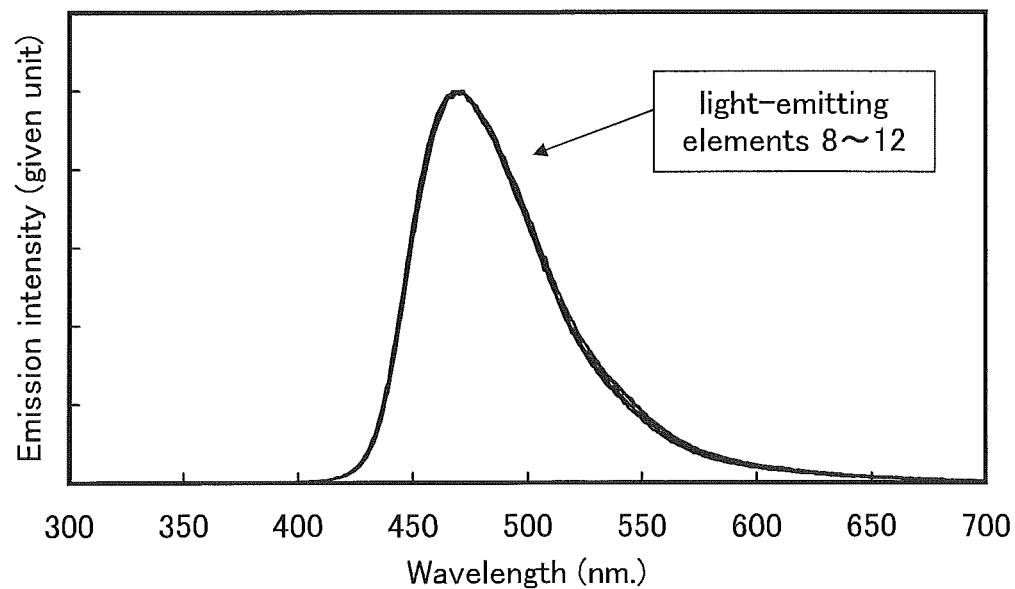
FIG. 26 is a graph of emission spectra of the light-emitting elements manufactured in Example 11.

FIG. 26 shows emission spectra when a current of 1 mA was made to flow in the manufactured light-emitting elements 8 to 12. In FIG. 26, a horizontal axis represents an emission wavelength (nm), and a longitudinal axis represents an emission intensity. FIG. 26 shows a comparative value of each light-emitting element with the same maximum emission intensity. It is understood from FIG. 26 that each of the light-emitting elements 8 to 12 emits preferable blue light which is resulted from PCBAPA which is a light-emitting substance.

Figure 27:
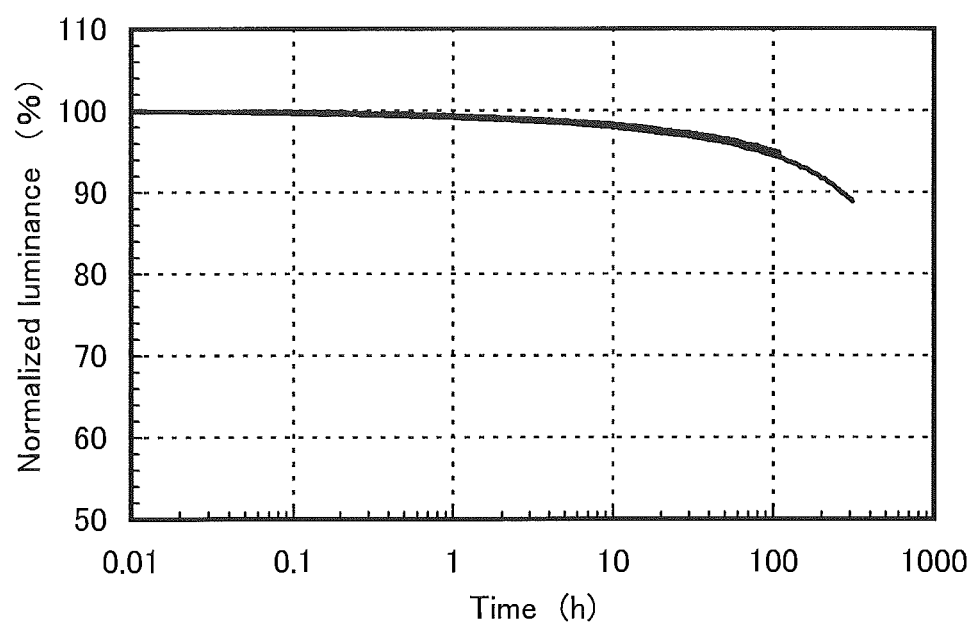
FIG. 27 is a graph of time vs. normalized luminance characteristics of the light-emitting elements manufactured in Example 11.

Next, time vs. normalized luminance characteristics of each element are shown in FIG. 27. A horizontal axis represents a time (h), and a longitudinal axis represents a normalized luminance (%). When these elements were driven under the condition of fixed current density with an initial luminance set at 1000 $cd/m^2$, each of the light-emitting elements similarly showed preferable characteristics in reliability. Note that in FIG. 27, the trajectories of the graph seem one because almost the same trajectories are drawn in each of the light-emitting elements (the light-emitting elements 8 to 12).

It was understood from the light-emitting elements 8 to 12 that the triarylamine derivative, which is described in Embodiment 1, together with an acceptor substance can be preferably used for the hole injecting layer 111. In addition, it was understood from the light-emitting element 12 that the triarylamine derivative described in Embodiment 1 is a preferable material that can be used for both the hole injecting layer 111 and the hole transporting layer 112 at the same time. Accordingly, an element was manufactured easily and it was also possible to improve the use efficiency of the material.

Example 12

When a composite material of a material having a high hole transporting property and an acceptor substance such as molybdenum(VI) oxide is used for a hole injecting layer of a light-emitting element, a material that forms an electrode can be selected regardless of a work function; therefore, the composite material is extremely useful. However, when light emission is taken out from the anode side, light transmitted through the composite material is extracted to the outside through a light-emitting element; therefore, there are some cases where a light-emitting element is affected disadvantageously depending on absorption characteristics of the composite material.

Figure 28:
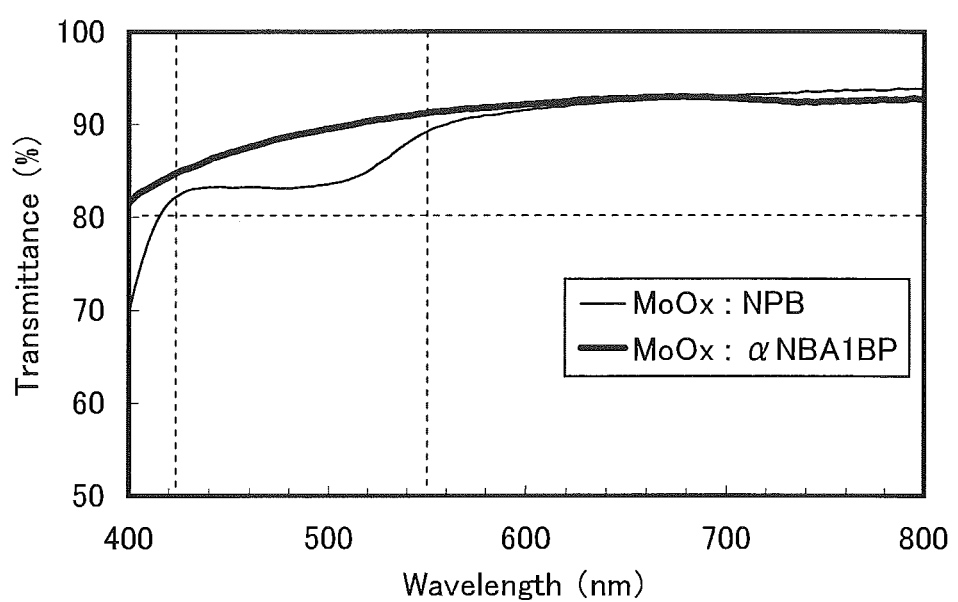
FIG. 28 is a graph of wavelength vs. transmittance characteristics of a composite material.

FIG. 28 shows wavelength vs. transmittance characteristics when NPB and αNBA1BP, which is the triarylamine derivative described in Embodiment 1, are each co-evaporated with molybdenum(VI) oxide. In FIG. 28, a horizontal axis represents a wavelength (nm), and a longitudinal axis represents a transmittance (%). Vacuum evaporation of NPB and αNBA1BP with molybdenum(VI) oxide was performed over a quartz substrate so that the mass ratios of NPB: molybdenum(VI) oxide and αNBA1BP: molybdenum(VI) oxide are each 4:1. The thicknesses were each 50 nm. Each transmission spectrum of the quartz substrate is subtracted from the total spectrum.

It is understood from FIG. 28 that the film of the composite material using NPB has broad absorption in the wavelength range of 420 nm to 550 nm. The absorption in the wavelength range of 420 nm to 550 nm corresponds to regions where blue light to green light are emitted, and when the composite material is used, light emissions from a light-emitting element emitting blue light to green light are absorbed by the composite material. Accordingly, there is a concern that an adverse effect might be caused on chromaticity and luminous efficiency. On the other hand, it is understood that the film of the composite material using αNBA1BP has broad absorption on the longer wavelength side than the wavelength of 700 nm. However, since the absorption region is not a visible region, there are a few influences on a light-emitting element.

In such a manner, since the composite material where αNBA1BP, which is the triarylamine derivative described in Embodiment 1, and molybdenum(VI) oxide are co-evaporated has little absorption to visible light, it was understood that the composite material can be preferably applied to light-emitting element emitting any visible light.

INDUSTRIAL APPLICABILITY

In a triarylamine derivative according to one embodiment of the present invention, energy gap is large or there is an energy difference (hereinafter also referred to as triplet energy) between a ground state and a triplet excited state; therefore, the triarylamine derivative can be very preferably used as a host material or a carrier transporting material (especially as a hole transporting material) of a light-emitting element providing blue fluorescence or a light-emitting element providing green phosphoresce. In addition, the triarylamine derivative according to one embodiment of the present invention can be used as a host material or a carrier transporting material of a light-emitting substance having emission wavelengths in a wide visible region (from blue light to red light), whereby light can be emitted efficiently. Moreover, in the case of forming a light-emitting device including a plurality of red, green, and blue pixels, a host material or a carrier transporting material can have the same kind also in a process of forming a light-emitting element; therefore, the process can be simplified and the use efficiency of the material is also high, which are preferable. Further, the triarylamine derivative according to one embodiment of the present invention can be used as a light-emitting substance and in that case the energy gap is large as described above; therefore, a light-emitting element with sufficiently short wavelengths and high color purity for blue light emission can be obtained. Then, since the triarylamine derivative according to one embodiment of the present invention has excellent characteristics as described above, a light-emitting element having preferable luminous efficiency can be provided, and thus a light-emitting device that consumes less power can be obtained. Besides, since light emission having high color purity, especially preferable blue light emission can also be obtained, a light-emitting device having excellent color reproducibility and high display quality can be obtained. Further, a lighting apparatus that consumes less power can also be obtained and in that case the lighting apparatus can be thin with a large area.

The present application is based on Japanese Patent Application serial No. 2008-129991, 2008-300827, and 2009-022314 filed with Japan Patent Office on May 16, 2008, Nov. 26, 2008, and Feb. 3, 2009, respectively, the entire contents of which are hereby incorporated by reference.

The invention claimed is:

1. A light-emitting device comprising:

a first electrode;

a second electrode;

a light-emitting layer comprising a light-emitting material between the first electrode and the second electrode;

a first layer comprising a first compound between the first electrode and the light-emitting layer; and a second layer comprising a second compound between the second electrode and the light-emitting layer, wherein the second compound comprises at least one of a metal complex, an oxadiazole skeleton, a triazole skeleton, bathophenanthroline, and bathocuproine, wherein the first compound is represented by a general formula (G1),

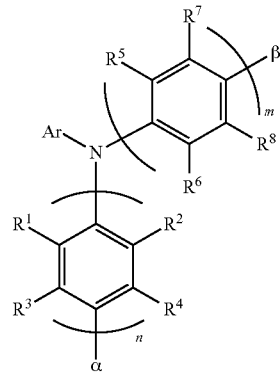

(G1)

wherein Ar represents any of substituents represented by structural formulae (Ar-1) to (Ar-4),

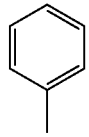

(Ar-1)

-continued

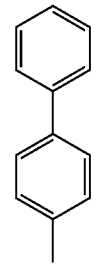
(Ar-2)

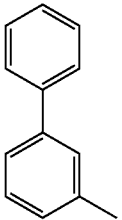
(Ar-3)

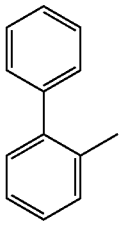
(Ar-4)

wherein α represents a first naphthyl group, wherein when the first naphthyl group has a substituent, the substituent is an alkyl group having 1 to 6 carbon atoms or a phenyl group, wherein β represents hydrogen or a second naphthyl group, wherein when the second naphthyl group has a substituent, the substituent is an alkyl group having 1 to 6 carbon atoms or a phenyl group, wherein n and m each independently represent 1 or 2, and wherein $R^1$ to $R^8$ each independently represent any of hydrogen, an alkyl group having 1 to 6 carbon atoms, and a phenyl group.

2. The light-emitting device according to claim 1, wherein the first naphthyl group is represented by structural formulae (α-1) or (α-2),

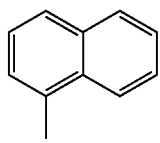
(α-1)

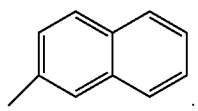
(α-2)

3. The light-emitting device according to claim 1, wherein the second naphthyl group is represented by structural formulae (β-2) or (β-3),

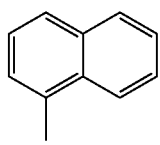
(β-2)

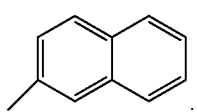
(β-3)

4. The light-emitting device according to claim 1, wherein each of n and m in the general formula (G1) represents 1.

5. The light-emitting device according to claim 1, wherein the light-emitting material is a fluorescent light-emitting material.

6. The light-emitting device according to claim 1, wherein the light-emitting material is a phosphorescent light-emitting material.

7. A light-emitting device comprising:

a first electrode;

a second electrode; and a composite material between the first electrode and the second electrode, wherein the composite material comprises a first organic compound and a second organic compound, wherein the second organic compound comprises at least one of a cyano group and a fluoro group, wherein the first organic compound is represented by a general formula (G1):

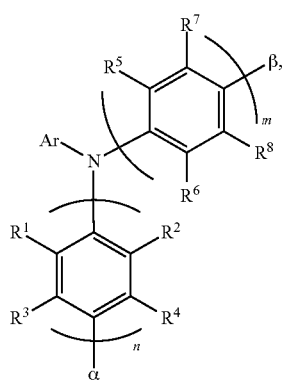
(G1)

wherein Ar represents any of substituents represented by structural formulae (Ar-1) to (Ar-4):

(Ar-1)

(Ar-2)

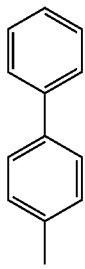

(Ar-3)

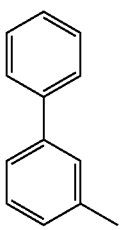

(Ar-4)

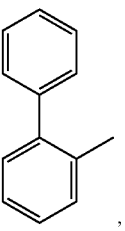

wherein α represents a first naphthyl group, wherein when the first naphthyl group has a substituent, the substituent is a phenyl group, wherein β represents hydrogen or a second naphthyl group, wherein when the second naphthyl group has a substituent, the substituent is a phenyl group, wherein n and m each independently represent 1 or 2, and wherein $R^1$ to $R^8$ each independently represent hydrogen or a phenyl group.

8. A light-emitting device comprising:

a first electrode;

a second electrode;

a light-emitting layer comprising a light-emitting material between the first electrode and the second electrode; and a layer between the first electrode and the light-emitting layer, wherein the layer comprises a first organic compound and a second organic compound, wherein the second organic compound comprises at least one of a cyano group and a fluoro group, wherein the first organic compound is represented by a general formula (G1):

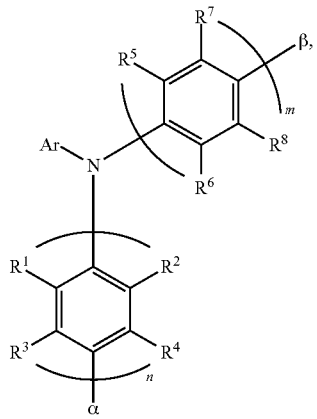

(G1)

wherein Ar represents any of substituents represented by structural formulae (Ar-1) to (Ar-4):

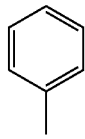

(Ar-1)

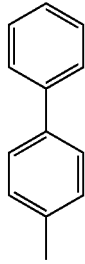

(Ar-2)

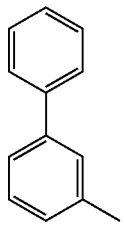

(Ar-3)

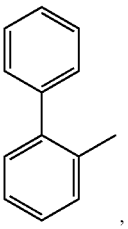

(Ar-4)

wherein α represents a first naphthyl group, wherein when the first naphthyl group has a substituent, the substituent is a phenyl group, wherein β represents hydrogen or a second naphthyl group, wherein when the second naphthyl group has a substituent, the substituent is a phenyl group, wherein n and m each independently represent 1 or 2, and wherein R¹ to R⁸ each independently represent hydrogen or a phenyl group.

9. The light-emitting device according to claim 7, wherein the first naphthyl group is represented by structural formulae (α-1) or (α-2):

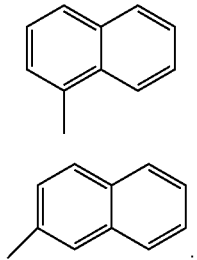
(α-1)

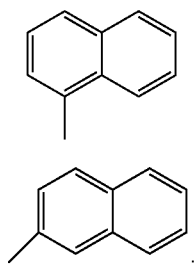
(α-2)

10. The light-emitting device according to claim 7, wherein the second naphthyl group is represented by structural formulae (β-2) or (β-3):

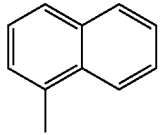
(β-2)

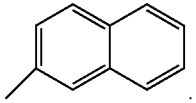
(β-3)

11. The light-emitting device according to claim 7, wherein each of n and m in the general formula (G1) represents 1.

12. The light-emitting device according to claim 7, wherein β represents hydrogen.

13. The light-emitting device according to claim 7, wherein R³ represents the phenyl group.

14. The light-emitting device according to claim 8, wherein R³ the first naphthyl group is represented by structural formulae (α-1) or (α-2):

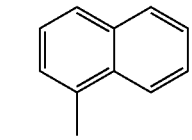
(α-1)

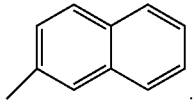
(α-2)

15. The light-emitting device according to claim 8, wherein the second naphthyl group is represented by structural formulae (β-2) or (β-3):

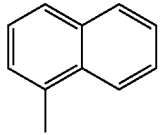
(β-2)

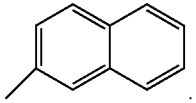
(β-3)

16. The light-emitting device according to claim 8, wherein each of n and m in the general formula (G1) represents 1.

17. The light-emitting device according to claim 8, wherein β represents hydrogen.

18. The light-emitting device according to claim 8, wherein R³ represents the phenyl group.

19. The light-emitting device according to claim 8, wherein the light-emitting material is a fluorescent light-emitting material.

20. The light-emitting device according to claim 8, wherein the light-emitting material is a phosphorescent light-emitting material.

* * * * *